US012365880B2

(12) United States Patent
Kawaoka et al.

(10) Patent No.: US 12,365,880 B2
(45) Date of Patent: Jul. 22, 2025

(54) RECOMBINANT INFLUENZA VIRUSES WITH STABILIZED NA

(71) Applicants: The University of Tokyo, Tokyo (JP); Wisconsin Alumni Research Foundation (WARF), Madison, WI (US)

(72) Inventors: Yoshihiro Kawaoka, Middleton, WI (US); Yuri Furusawa, Tokyo (JP); Seiya Yamayoshi, Kanagawa (JP)

(73) Assignees: The University of Tokyo, Tokyo (JP); Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 18/365,082

(22) Filed: Aug. 3, 2023

(65) Prior Publication Data

US 2024/0010995 A1    Jan. 11, 2024

Related U.S. Application Data

(62) Division of application No. 17/155,625, filed on Jan. 22, 2021, now Pat. No. 11,739,303.

(60) Provisional application No. 62/965,225, filed on Jan. 24, 2020.

(51) Int. Cl.
*C12N 7/00* (2006.01)
*A61K 39/145* (2006.01)
*A61K 39/00* (2006.01)

(52) U.S. Cl.
CPC ............ *C12N 7/00* (2013.01); *A61K 39/145* (2013.01); *A61K 2039/5252* (2013.01); *A61K 2039/552* (2013.01); *C12N 2760/16121* (2013.01); *C12N 2760/16134* (2013.01); *C12N 2760/16151* (2013.01); *C12N 2760/16163* (2013.01)

(58) Field of Classification Search
CPC ............ A61K 2039/5252; A61K 39/12; A61K 39/145; A61P 31/16; C12N 2760/16121
See application file for complete search history.

(56) References Cited

U.S. PATENT DOCUMENTS

| | | | |
|---|---|---|---|
| 4,071,618 A | 1/1978 | Konobe et al. |
| 4,659,569 A | 4/1987 | Mitsuhashi et al. |
| 5,166,057 A | 11/1992 | Palese et al. |
| 5,578,473 A | 11/1996 | Palese et al. |
| 5,716,821 A | 2/1998 | Wertz et al. |
| 5,750,394 A | 5/1998 | Palese et al. |
| 5,786,199 A | 7/1998 | Palese |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,948,410 A | 9/1999 | Van Scharrenburg et al. |
| 5,994,526 A | 11/1999 | Meulewaeter et al. |
| 6,001,634 A | 12/1999 | Palese et al. |
| 6,033,886 A | 3/2000 | Conzelmann |
| 6,037,348 A | 3/2000 | Colacino et al. |
| 6,146,642 A | 11/2000 | Garcia-Sastre et al. |
| 6,169,175 B1 | 1/2001 | Frace et al. |
| 6,194,546 B1 | 2/2001 | Newton et al. |
| 6,270,958 B1 | 8/2001 | Olivo et al. |
| 6,271,011 B1 | 8/2001 | Lee et al. |
| 6,358,733 B1 | 3/2002 | Motwani et al. |
| 6,455,298 B1 | 9/2002 | Groner et al. |
| 6,544,785 B1 | 4/2003 | Palese et al. |
| 6,656,720 B2 | 12/2003 | Groner et al. |
| 6,825,036 B2 | 11/2004 | Makizumi et al. |
| 6,843,996 B1 | 1/2005 | Parkin et al. |
| 6,872,395 B2 | 3/2005 | Kawaoka |
| 6,890,710 B1 | 5/2005 | Palese et al. |
| 6,951,752 B2 | 10/2005 | Reiter et al. |
| 6,951,754 B2 | 10/2005 | Hoffmann |
| 6,974,695 B2 | 12/2005 | Vogels et al. |
| 7,037,707 B2 | 5/2006 | Webster et al. |
| 7,176,021 B2 | 2/2007 | Kawaoka |
| 7,211,378 B2 | 5/2007 | Kawaoka et al. |
| 7,226,774 B2 | 6/2007 | Kawaoka |
| 7,312,064 B2 | 12/2007 | Hoffmann |
| 7,335,356 B2 | 2/2008 | Hart et al. |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,601,356 B2 | 10/2009 | Jin et al. |
| 7,670,837 B2 | 3/2010 | Schwartz |
| 7,682,618 B2 | 3/2010 | Bavari et al. |
| 7,723,094 B2 | 5/2010 | Kawaoka et al. |
| 7,833,788 B2 | 11/2010 | Pau et al. |
| 7,883,844 B2 | 2/2011 | Nouchi et al. |

(Continued)

FOREIGN PATENT DOCUMENTS

| | | |
|---|---|---|
| AU | 2012204138 B2 | 5/2014 |
| AU | 2014202470 A1 | 11/2016 |

(Continued)

OTHER PUBLICATIONS

"Israel Application Serial No. 163,546, First Examination Report mailed Jul. 28, 2008", (English Translation), 2 pgs.

(Continued)

*Primary Examiner* — Bao Q Li
(74) *Attorney, Agent, or Firm* — Schwegman Lundberg & Woessner, P.A.

(57) ABSTRACT

Modified influenza virus neuraminidases are described herein that have stabilized NA tetramers which may improve vaccine production efficiency, thus improving the yield of vaccine viruses.

17 Claims, 22 Drawing Sheets

Specification includes a Sequence Listing.

(56) References Cited

U.S. PATENT DOCUMENTS

| | | |
|---|---|---|
| 7,955,833 B2 | 6/2011 | Reiter et al. |
| 7,959,930 B2 | 6/2011 | De Wit et al. |
| 7,968,101 B2 | 6/2011 | Kawaoka et al. |
| 7,972,843 B2 | 7/2011 | Hoffmann |
| 7,993,924 B2 | 8/2011 | Billeter et al. |
| 8,012,736 B2 | 9/2011 | Hoffman et al. |
| 8,043,856 B2 | 10/2011 | Kawaoka et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,298,805 B2 | 10/2012 | Kawaoka |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,465,960 B2 | 6/2013 | Kawaoka et al. |
| 8,475,806 B2 | 7/2013 | Kawaoka |
| 8,507,247 B2 | 8/2013 | Kawaoka et al. |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 8,597,661 B2 | 12/2013 | Kawaoka et al. |
| 8,679,819 B2 | 3/2014 | Kawaoka |
| 8,877,209 B2 | 11/2014 | Kawaoka et al. |
| 8,900,595 B2 | 12/2014 | Kawaoka et al. |
| 9,101,653 B2 | 8/2015 | Kawaoka et al. |
| 9,109,013 B2 | 8/2015 | Kawaoka et al. |
| 9,222,118 B2 | 12/2015 | Kawaoka et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,890,363 B2 | 2/2018 | Kawaoka |
| 9,926,535 B2 | 3/2018 | Kawaoka et al. |
| 9,950,057 B2 | 4/2018 | Kawaoka et al. |
| 10,053,671 B2 | 8/2018 | Kawaoka et al. |
| 10,059,925 B2 | 8/2018 | Kawaoka et al. |
| 10,119,124 B2 | 11/2018 | Watanabe et al. |
| 10,130,697 B2 | 11/2018 | Watanabe |
| 10,172,934 B2 | 1/2019 | Kawaoka et al. |
| 10,246,686 B2 | 4/2019 | Kawaoka et al. |
| 10,358,630 B2 | 7/2019 | Kawaoka et al. |
| 10,494,613 B2 | 12/2019 | Kawaoka et al. |
| 10,513,692 B2 | 12/2019 | Kawaoka et al. |
| 10,633,422 B2 | 4/2020 | Kawaoka et al. |
| 10,808,229 B2 | 10/2020 | Kawaoka et al. |
| 11,007,262 B2 | 5/2021 | Watanabe et al. |
| 11,046,934 B2 | 6/2021 | Kawaoka et al. |
| 11,180,737 B2 | 11/2021 | Kawaoka et al. |
| 11,197,925 B2 | 12/2021 | Kawaoka et al. |
| 11,197,926 B2 | 12/2021 | Kawaoka et al. |
| 11,241,492 B2 | 2/2022 | Kawaoka et al. |
| 11,384,339 B2 | 7/2022 | Kawaoka et al. |
| 11,389,523 B2 | 7/2022 | Kawaoka et al. |
| 11,390,649 B2 | 7/2022 | Kawaoka et al. |
| 11,739,303 B2 | 8/2023 | Kawaoka et al. |
| 11,802,273 B2 | 10/2023 | Kawaoka et al. |
| 11,807,872 B2 | 11/2023 | Kawaoka et al. |
| 11,851,648 B2 | 12/2023 | Kawaoka et al. |
| 12,076,387 B2 | 9/2024 | Watanabe et al. |
| 12,122,807 B2 | 10/2024 | Kawaoka et al. |
| 12,144,857 B2 | 11/2024 | Kawaoka et al. |
| 12,251,436 B2 | 3/2025 | Kawaoka et al. |
| 12,258,557 B2 | 3/2025 | Kawaoka et al. |
| 12,290,562 B2 | 5/2025 | Kawaoka et al. |
| 2002/0010143 A1 | 1/2002 | Barbosa et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2003/0215794 A1 | 11/2003 | Kawaoka et al. |
| 2004/0002061 A1 | 1/2004 | Kawaoka |
| 2004/0029251 A1 | 2/2004 | Hoffman et al. |
| 2004/0057967 A1 | 3/2004 | Bavari et al. |
| 2004/0063141 A1 | 4/2004 | Lok |
| 2004/0077086 A1 | 4/2004 | Reiter et al. |
| 2004/0132164 A1 | 7/2004 | Doyle et al. |
| 2004/0142322 A1 | 7/2004 | Malcolm et al. |
| 2004/0219170 A1 | 11/2004 | Kawaoka |
| 2004/0241139 A1 | 12/2004 | Hobom et al. |
| 2004/0242518 A1 | 12/2004 | Chen et al. |
| 2005/0003349 A1 | 1/2005 | Kawaoka |
| 2005/0037487 A1 | 2/2005 | Kawaoka et al. |
| 2005/0095583 A1 | 5/2005 | Pekosz et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266023 A1 | 12/2005 | Bavari et al. |
| 2005/0266026 A1 | 12/2005 | Hoffmann et al. |
| 2006/0057116 A1 | 3/2006 | Kawaoka et al. |
| 2006/0088909 A1 | 4/2006 | Compans |
| 2006/0099609 A1 | 5/2006 | Bavari et al. |
| 2006/0134138 A1 | 6/2006 | Kawaoka et al. |
| 2006/0166321 A1 | 7/2006 | Kawaoka et al. |
| 2006/0188977 A1 | 8/2006 | Schwartz et al. |
| 2006/0216702 A1 | 9/2006 | Compans et al. |
| 2006/0240515 A1 | 10/2006 | Dimitrov et al. |
| 2006/0246092 A1 | 11/2006 | Neirynck et al. |
| 2007/0141699 A1 | 6/2007 | Kawaoka |
| 2007/0231348 A1 | 10/2007 | Kawaoka et al. |
| 2008/0009031 A1 | 1/2008 | Kawaoka |
| 2008/0187557 A1 | 8/2008 | Sambhara |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0292658 A1 | 11/2008 | De Wit et al. |
| 2008/0293040 A1 | 11/2008 | Kawaoka et al. |
| 2008/0311148 A1 | 12/2008 | Hoffmann |
| 2008/0311149 A1 | 12/2008 | Hoffmann |
| 2009/0017444 A1 | 1/2009 | Kawaoka et al. |
| 2009/0047728 A1 | 2/2009 | Kawaoka et al. |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2009/0311669 A1 | 12/2009 | Kawaoka |
| 2009/0324640 A1 | 12/2009 | Kawaoka et al. |
| 2010/0021499 A1 | 1/2010 | Bilsel et al. |
| 2010/0080825 A1 | 4/2010 | Kawaoka et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2010/0267116 A1 | 10/2010 | Kawaoka et al. |
| 2011/0020374 A1 | 1/2011 | Frazer |
| 2011/0027314 A1 | 2/2011 | Broeker |
| 2011/0045022 A1 | 2/2011 | Tsai |
| 2011/0081373 A1 | 4/2011 | Kawaoka et al. |
| 2011/0110978 A1 | 5/2011 | Kawaoka et al. |
| 2011/0159031 A1 | 6/2011 | Falkner et al. |
| 2011/0236417 A1 | 9/2011 | Watanabe et al. |
| 2011/0263554 A1 | 10/2011 | Kawaoka et al. |
| 2011/0300604 A1 | 12/2011 | Kawaoka et al. |
| 2012/0020997 A1 | 1/2012 | Hoffman et al. |
| 2012/0034600 A1 | 2/2012 | Gregersen |
| 2012/0058124 A1 | 3/2012 | Kurosawa et al. |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2012/0251568 A1 | 10/2012 | Garcia-sastre et al. |
| 2013/0095135 A1 | 4/2013 | Collignon et al. |
| 2013/0183741 A1 | 7/2013 | Park et al. |
| 2013/0230552 A1 | 9/2013 | Kawaoka et al. |
| 2013/0243744 A1 | 9/2013 | Betenbaugh |

(56) References Cited

U.S. PATENT DOCUMENTS

| | | |
|---|---|---|
| 2013/0315929 A1 | 11/2013 | Bock |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0166967 A1 | 6/2015 | Kawaoka et al. |
| 2015/0307851 A1 | 10/2015 | Kawaoka et al. |
| 2015/0368621 A1 | 12/2015 | Kawaoka et al. |
| 2016/0024193 A1 | 1/2016 | Ayalon et al. |
| 2016/0024479 A1 | 1/2016 | Kawaoka et al. |
| 2016/0115518 A1 | 4/2016 | Kawaoka et al. |
| 2016/0208223 A1 | 7/2016 | Kawaoka et al. |
| 2016/0215040 A1 | 7/2016 | Kyratsous et al. |
| 2016/0355790 A1 | 12/2016 | Kawaoka et al. |
| 2017/0058265 A1 | 3/2017 | Kawaoka et al. |
| 2017/0067029 A1 | 3/2017 | Kawaoka et al. |
| 2017/0096645 A1 | 4/2017 | Watanabe et al. |
| 2017/0097334 A1 | 4/2017 | Kawaoka et al. |
| 2017/0121391 A1 | 5/2017 | Kawaoka et al. |
| 2017/0258888 A1 | 9/2017 | Kawaoka |
| 2017/0298120 A1 | 10/2017 | Sasisekharan |
| 2017/0354730 A1 | 12/2017 | Kawaoka et al. |
| 2018/0245054 A1 | 8/2018 | Kawaoka et al. |
| 2018/0273588 A1 | 9/2018 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2019/0117759 A1 | 4/2019 | Wantanabe et al. |
| 2019/0167781 A1 | 6/2019 | Kawaoka et al. |
| 2020/0188506 A1 | 6/2020 | Kawaoka et al. |
| 2020/0237899 A1 | 7/2020 | Kawaoka et al. |
| 2020/0263142 A1 | 8/2020 | Kawaoka et al. |
| 2020/0263143 A1 | 8/2020 | Kawaoka et al. |
| 2020/0291384 A1 | 9/2020 | Kawaoka et al. |
| 2021/0061862 A1 | 3/2021 | Kawaoka et al. |
| 2021/0102178 A1 | 4/2021 | Kawaoka et al. |
| 2021/0121545 A1 | 4/2021 | Knoll et al. |
| 2021/0228708 A1 | 7/2021 | Smith et al. |
| 2021/0246432 A1 | 8/2021 | Kawaoka et al. |
| 2021/0252130 A1 | 8/2021 | Watanabe et al. |
| 2021/0290754 A1 | 9/2021 | Kawaoka et al. |
| 2021/0299249 A1 | 9/2021 | Kawaoka et al. |
| 2022/0025339 A1 | 1/2022 | Kawaoka et al. |
| 2022/0202926 A1 | 6/2022 | Kawaoka et al. |
| 2022/0202927 A1 | 6/2022 | Kawaoka et al. |
| 2022/0241396 A1 | 8/2022 | Kawaoka et al. |
| 2023/0190913 A1 | 6/2023 | Kawaoka et al. |
| 2023/0192775 A1 | 6/2023 | Kawaoka et al. |
| 2023/0321217 A1 | 10/2023 | Kawaoka et al. |
| 2023/0346911 A1 | 11/2023 | Kawaoka et al. |
| 2023/0348864 A1 | 11/2023 | Kawaoka et al. |
| 2024/0076632 A1 | 3/2024 | Kawaoka et al. |
| 2024/0238403 A1 | 7/2024 | Kawaoka et al. |
| 2024/0318167 A1 | 9/2024 | Kawaoka et al. |
| 2025/0034214 A1 | 1/2025 | Kawaoka et al. |

FOREIGN PATENT DOCUMENTS

| | | |
|---|---|---|
| AU | 2014290203 B2 | 12/2020 |
| AU | 2017221444 B2 | 11/2021 |
| AU | 2021201844 | 2/2023 |
| BR | PI0410702 B1 | 4/2022 |
| CA | 2379012 A1 | 1/2001 |
| CA | 2816242 C | 1/2019 |
| CA | 3014435 | 4/2023 |
| CA | 2525953 | 10/2023 |
| CN | 1826407 A | 8/2006 |
| CN | 101472941 A | 7/2009 |
| CN | 101613678 | 12/2009 |
| CN | 1826407 B | 9/2013 |
| CN | 105296356 | 2/2016 |
| CN | 106661569 | 5/2017 |
| CN | 103540614 B | 2/2018 |
| CN | 109477074 A | 3/2019 |
| CN | 113874496 | 12/2021 |
| CN | 113874496 A | 12/2021 |
| CN | 114929269 | 8/2022 |
| CN | 114929269 A | 8/2022 |
| CN | 109477074 B | 1/2023 |
| EP | 0687471 | 12/1995 |
| EP | 0700991 | 3/1996 |
| EP | 0702085 A1 | 3/1996 |
| EP | 0704533 A1 | 4/1996 |
| EP | 1201760 A1 | 5/2002 |
| EP | 2010557 B1 | 2/2014 |
| EP | 1572910 B1 | 12/2015 |
| EP | 1631663 B1 | 8/2016 |
| EP | 2747778 B1 | 12/2017 |
| EP | 3009507 B1 | 6/2020 |
| EP | 2493912 B1 | 7/2020 |
| EP | 3022296 B1 | 12/2022 |
| IL | 171831 A | 5/2015 |
| JP | 07-203958 | 8/1995 |
| JP | H08510749 A | 11/1996 |
| JP | H10500113 A | 1/1998 |
| JP | 2002536992 A | 11/2002 |
| JP | 2003528570 A | 9/2003 |
| JP | 2004500842 A | 1/2004 |
| JP | 2004531232 A | 10/2004 |
| JP | 2005523698 A | 8/2005 |
| JP | 2005245302 A | 9/2005 |
| JP | 2005535288 A | 11/2005 |
| JP | 2006525815 A | 11/2006 |
| JP | 2007518395 A | 7/2007 |
| JP | 2007525175 A | 9/2007 |
| JP | 2007259758 | 10/2007 |
| JP | 2007529997 A | 11/2007 |
| JP | 2008500041 | 1/2008 |
| JP | 2008512443 | 4/2008 |
| JP | 2008520248 A | 6/2008 |
| JP | 2009511084 A | 3/2009 |
| JP | 2009514850 A | 4/2009 |
| JP | 2009523252 A | 6/2009 |
| JP | 2009532352 A | 9/2009 |
| JP | 2009539965 A | 11/2009 |
| JP | 2010530248 A | 9/2010 |
| JP | 2011530295 A | 12/2011 |
| JP | 4927290 | 5/2012 |
| JP | 4927290 B2 | 5/2012 |
| JP | 2013507990 A | 3/2013 |
| JP | 2013511280 A | 4/2013 |
| JP | 2013518059 | 5/2013 |
| JP | 2014039551 A | 3/2014 |
| JP | 2014131516 A | 7/2014 |
| JP | 2015501141 | 1/2015 |
| JP | 2016500007 A | 1/2016 |
| JP | 2016521553 A | 7/2016 |
| JP | 2016144463 A | 8/2016 |
| JP | 2016524915 A | 8/2016 |
| JP | 2016169225 A | 9/2016 |
| JP | 2017506903 | 3/2017 |
| JP | 2017527557 A | 9/2017 |
| JP | 2017197555 A | 11/2017 |
| JP | 2018064493 A | 4/2018 |
| JP | 6352974 B2 | 6/2018 |
| JP | 6375329 B2 | 7/2018 |
| JP | 2019510481 A | 4/2019 |
| JP | 2020010711 A | 1/2020 |
| JP | 2020114250 A | 7/2020 |
| JP | 2021500891 A | 1/2021 |
| JP | 2021036878 A | 3/2021 |
| JP | 2021184761 A | 12/2021 |
| JP | 2021533157 A | 12/2021 |
| JP | 2021536228 A | 12/2021 |
| JP | 2022066209 A | 4/2022 |
| JP | 2022522112 A | 4/2022 |
| JP | 2022527235 A | 6/2022 |
| JP | 2022172369 A | 11/2022 |
| JP | 2022551805 A | 12/2022 |
| JP | 2023011603 A | 1/2023 |
| JP | 7244455 | 3/2023 |
| JP | 2023511444 | 3/2023 |
| JP | 7297832 | 6/2023 |
| JP | 2023109845 | 8/2023 |
| JP | 2024028825 | 3/2024 |

(56) References Cited

FOREIGN PATENT DOCUMENTS

| | | |
|---|---|---|
| JP | 2024091645 | 7/2024 |
| JP | 7642346 | 2/2025 |
| JP | 7655849 | 3/2025 |
| JP | 7662157 | 4/2025 |
| JP | 2025061501 | 4/2025 |
| KR | 101113432 B1 | 2/2012 |
| MX | 285206 | 3/2011 |
| NO | 341506 | 11/2017 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9848834 A1 | 11/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-2000060050 A2 | 10/2000 |
| WO | WO-0060050 A3 | 1/2001 |
| WO | WO-2001004333 A1 | 1/2001 |
| WO | WO-2001025462 A1 | 4/2001 |
| WO | WO-0179273 A2 | 10/2001 |
| WO | WO-2001079273 A2 | 10/2001 |
| WO | WO-0183794 A2 | 11/2001 |
| WO | WO-2001083794 A2 | 11/2001 |
| WO | WO-0210143 A1 | 1/2002 |
| WO | WO-02064757 A2 | 8/2002 |
| WO | WO-02074795 A2 | 9/2002 |
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |
| WO | WO-03091401 A2 | 11/2003 |
| WO | WO-2003091401 A2 | 11/2003 |
| WO | 04094466 | 11/2004 |
| WO | WO-2004094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | WO-2005062820 A2 | 7/2005 |
| WO | WO-2006051069 A2 | 5/2006 |
| WO | WO-2007044024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008156681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO-09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | WO-2009152181 A1 | 12/2009 |
| WO | WO-2009128867 A3 | 3/2010 |
| WO | WO-2010053573 A2 | 5/2010 |
| WO | WO-2010053573 A3 | 7/2010 |
| WO | WO-2011014645 A1 | 2/2011 |
| WO | 2011063308 | 5/2011 |
| WO | WO-2011056591 A1 | 5/2011 |
| WO | WO-2011087839 A1 | 7/2011 |
| WO | WO-2011126370 A1 | 10/2011 |
| WO | WO-2011130627 A2 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | WO-2015134488 A1 | 9/2015 |
| WO | WO-2015142671 A2 | 9/2015 |
| WO | WO-2015196150 A2 | 12/2015 |
| WO | WO-2015196150 A3 | 12/2015 |
| WO | 2016144933 | 9/2016 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | WO-2019084310 A1 | 5/2019 |
| WO | 2019241579 | 12/2019 |
| WO | WO-2020033527 A2 | 2/2020 |
| WO | WO-2020041311 A1 | 2/2020 |
| WO | 2020061443 | 3/2020 |
| WO | WO-2020/033527 A3 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | 2021150874 | 7/2021 |
| WO | 2021195410 | 9/2021 |
| WO | WO-2021195410 A1 | 9/2021 |
| WO | 2021242597 | 12/2021 |
| WO | WO-2021242597 A1 | 12/2021 |
| WO | 2022245888 | 11/2022 |
| WO | 2023125889 | 7/2023 |
| WO | 2023164556 | 8/2023 |
| WO | 2024015510 | 1/2024 |

OTHER PUBLICATIONS

"U.S. Appl. No. 10/827,995, Notice of Allowance mailed Jul. 2, 2008", 9 pgs.

"International Application Serial No. PCT US2003 004233, International Search Report mailed Dec. 16, 2005", 5 pgs.

"Eurasian Application Serial No. 200501890, Response filed Dec. 17, 2008 to Office Action", (w English Translation of Claims), 13 pgs.

"U.S. Appl. No. 11/043,768, Response filed Jun. 23, 2009 to Non Final Office Action mailed Feb. 23, 2009", 9 pgs.

"U.S. Appl. No. 10/855,875, Response filed Dec. 7, 2009 to Non-Final Office Action mailed Aug. 7, 2009", 15 pgs.

"Identification by siRNA of host proteins involved in Ebolavirus replication", Index of GLRCE: documents from 2007Great Lakes Regional Center of Excellence Index, Retrieved from the Internet: URL:http: www.rcebiodefense.org glrce docs 2007 Kawaokja.pdf [retrieved on Jan. 14, 2010], (2007), 8 pgs.

"Israeli Application Serial No. 238584, Office Action mailed Jul. 24, 2017", (Translation), 2 pgs.

"International Application Serial No. PCT US2019 037084, Invitation to Pay Add'l Fees and Partial Search Report mailed Sep. 24, 2019", 10 pgs.

"International Application Serial No. PCT US2019 037084, International Search Report mailed Nov. 14, 2019", 10 pgs.

"International Application Serial No. PCT US2019 037084, Written Opinion mailed Nov. 14, 2019", 10 pgs.

"International Application Serial No. PCT US2019 037084, International Preliminary Report on Patentability mailed Dec. 24, 2020", 12 pgs.

"Japanese Application Serial No. 2022-544779, Voluntary Amendment filed Sep. 9, 2022", w English Claims, 8 pgs.

"Japanese Application Serial No. 2021-546853, Notification of Reasons for Refusal mailed Apr. 18, 2023", w English Translation, 11 pgs.

(56) References Cited

OTHER PUBLICATIONS

"U.S. Appl. No. 17/004,583, Notice of Allowance mailed May 15, 2023", 7 pgs.
"U.S. Appl. No. 17/352,845, Response filed May 16, 2023 to Non Final Office Action mailed Dec. 16, 2022", 8 pgs.
"U.S. Appl. No. 17/212,836, Response filed May 16, 2023 to Non Final Office Action mailed Feb. 16, 2023", 7 pgs.
"European Application Serial No. 18800815.5, Communication Pursuant to Article 94(3) EPC mailed May 9, 2023", 6 pgs.
"U.S. Appl. No. 16/785,449, Response filed May 22, 2023 to Final Office Action mailed Mar. 22, 2023", 9 pgs.
"U.S. Appl. No. 17/546,967, Restriction Requirement mailed May 23, 2023", 10 pgs.
"Japanese Application Serial No. 2022-016436, Notification of Reasons for Refusal mailed Apr. 11, 2023", w English translation, 13 pgs.
"Japanese Application Serial No. 2021-542525, Response filed May 18, 2023 Notification of Reasons for Refusal mailed Dec. 13, 2022", w English Claims, 58 pgs.
"U.S. Appl. No. 17/229,001, Non Final Office Action mailed Jun. 6, 2023", 15 pgs.
"U.S. Appl. No. 17/352,845, Notice of Allowance mailed Jun. 7, 2023", 5 pgs.
"Japanese Application Serial No. 2022-513269, Notification of Reasons for Refusal mailed Jun. 6, 2023", w English Translation, 15 pgs.
Author Unknown, "New Approaches to Influenza Vaccine", Medscape—Infections in Medicine, http: www.medscape.com viewarticle 417404_3, (Observed Feb. 26, 2003), 4 pgs.
Bullido, Rosario, "Influenza A Virus Nep NS2 Protein Downregulates RNA Synthesis of Model Template RNAs", Journal of Virology vol. 75 No. 10, (May 2001), 6 pgs.
Martorelli Di, Genova B., "Intestinal delta-6-desaturase activity determines host range for Toxoplasma sexual reproduction", PLOS Biology, vol. 17, No. 8, E3000364, (Aug. 20, 2019), XP055619380, (Aug. 20, 2019), 1-19.
Matrosovich, "Early Alteration of the Receptor-Binding Properties of H1, H2, and H3 Avian Influenza Virus Hemagglutinins after Their Introduction to Mammals", J. Virology, 74(18) 8502-8512, (Sep. 2000), 11 pgs.
Pittman, Kelly J., "Z-DNA Binding Protein Mediates Host Control of Toxoplasma gondii Infection", Infection and Immunity, 84(10), (Oct. 2016), 3063-3070.
Powell, Robin H., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Schares, G., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.
Stroud, Chad K., "Disruption of FADS2 gene in mice impairs male reproduction and causes dermal and intestinal ulceration", Journal of Lipid Research, vol. 50, (2009), 1870-1880.
Vaishnava, Shipra, "The Antibacterial Lectin Regllly Promotes the Spatial Segregation of Microbiota and Host in the Intestine", Science, 334 255-258, (2011), 4 pgs.
Waap, Helga, "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
"U.S. Appl. No. 18/173,535, Preliminary Amendment filed Jun. 26, 2023", 16 pgs.
"Japanese Application Serial No. 2021-546853, Response Filed Jul. 13, 2023 to Notification of Reasons for Refusal mailed Apr. 18, 2023", W English Claims, 12 pgs.
"Japanese Application Serial No. 2021-546853, Notification of Reasons for Refusal mailed Aug. 29, 2023", w English Translation, 6 pgs.
"Japanese Application Serial No. 2021-536228, Notification of Reasons for Rejection mailed Aug. 22, 2023", W English Translation, 13 pgs.
Matrosovich, Mikhail, "Overexpression of the a-2,6-Sialyltransferase in MDCK Cells Increases Influenza Virus Sensitivity to Neuraminidase Inhibitors", Journal of Virology, Aug. 2003, p. 8418-8425, (2003), 9 pgs.
"Japanese Application Serial No. 2022-513269, Response filed Dec. 6, 2023 to Notification of Reasons for Refusal mailed Jun. 6, 2023", w english claims, 34 pgs.
"U.S. Appl. No. 17/835,830, Restriction Requirement mailed Dec. 26, 2023", 8 pgs.
"Japanese Application Serial No. 2021-542525, Response filed Dec. 1, 2023 to Examiners Decision of Final Refusal mailed Aug. 1, 2023", w english claim, 7 pgs.
"Japanese Application Serial No. 2022-016436, Notification of Reasons for Refusal mailed Dec. 5, 2023", w English Translation, 10 pgs.
"Japanese Application Serial No. 2022-016436, Response filed Oct. 11, 2023 to Notification of Reasons for Refusal mailed Apr. 11, 2023", w English claims, 15 pgs.
"European Application Serial No. 16778485.9, Response filed Dec. 15, 2023 to Communication Pursuant to Article 94(3) EPC mailed Jun. 9, 2023", 54 pgs.
"U.S. Appl. No. 17/229,001, Response filed Feb. 14, 2024 to Non Final Office Action mailed Oct. 19, 2023", 12 pgs.
"U.S. Appl. No. 17/266,049, Response filed Feb. 15, 2024 to Final Office Action mailed Aug. 15, 2023", 11 pgs.
"U.S. Appl. No. 17/813,200, Response filed Feb. 23, 2024 to Non Final Office Action mailed Oct. 23, 2023", 12 pgs.
"Japanese Application Serial No. 2022-544779, Response filed Jan. 10, 2024 to Notification of Reasons for Refusal mailed Aug. 22, 2023", w English claims, 12 pgs.
"Japanese Application Serial No. 2023-204069, Voluntary Amendment filed Dec. 28, 2023", w English claim, 8 pgs.
"U.S. Appl. No. 17/835,830, Response filed Feb. 29, 2024 to Restriction Requirement mailed Dec. 26, 2023", 6 pgs.
"U.S. Appl. No. 17/546,967, Non Final Office Action mailed Mar. 8, 2024", 9 pgs.
"U.S. Appl. No. 16/785,449, Advisory Action mailed Jun. 7, 2023", 17 pgs.
"U.S. Appl. No. 17/266,049, Response filed Jun. 14, 2023 to Non Final Office Action mailed Mar. 14, 2023", 10 pgs.
"European Application Serial No. 16778485.9, Communication Pursuant to Article 94(3) EPC mailed Jun. 9, 2023", 4 pgs.
"U.S. Appl. No. 17/212,836, Final Office Action mailed Jun. 22, 2023", 15 pgs.
"U.S. Appl. No. 16/785,449, Response filed Jul. 13, 2023 to Advisory Action mailed Jun. 7, 2023", 12 pgs.
"U.S. Appl. No. 17/004,583, Notice of Allowability mailed Aug. 1, 2023", 2 pgs.
"U.S. Appl. No. 16/785,449, Notice of Allowance mailed Aug. 7, 2023", 14 pgs.
"U.S. Appl. No. 17/266,049, Final Office Action mailed Aug. 15, 2023", 12 pgs.
"U.S. Appl. No. 17/212,836, Response filed Aug. 22, 2023 to Final Office Action mailed Jun. 22, 2023", 7 pgs.
"U.S. Appl. No. 17/229,001, Response filed Aug. 28, 2023 to Non Final Office Action mailed Jun. 6, 2023", 13 pgs.
"U.S. Appl. No. 17/212,836, Advisory Action mailed Aug. 29, 2023", 3 pgs.
"Japanese Application Serial No. 2021-542525, Examiners Decision of Final Refusal mailed Aug. 1, 2023", w English Translation, 7 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice of Allowability mailed Sep. 11, 2023", 10 pgs.
"Japanese Application Serial No. 2022-144599, Notification of Reasons for Refusal mailed Aug. 22, 2023", w english translation, 19 pgs.

(56) References Cited

OTHER PUBLICATIONS

Abdoli, Mohsen, "Intranasal administration of cold-adapted live-attenuated SARS-CoV-2 candidate vaccine confers protection against SARS-CoV-2", Virus Research 319 198857, (2022), 10 pgs.

Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.

Lu, Shan, "The SARS-CoV-2 nucleocapsid phosphoprotein forms mutually exclusive condensates with RNA and the membrane-associated M protein", nature communications 12:502, (2021), 15 pgs.

Plescia, Caroline B, "SARS-CoV-2 viral budding and entry can be modeled using BSL-2 level virus-like particles", JBC Research Article, (Nov. 19, 2020), 10 pgs.

Seo, Sang Heui, "Cold-Adapted Live Attenuated SARS-COV-2 Vaccine Completely Protects Human ACE2 Transgenic Mice from SARS-Cov-2 Infection", Vaccines 2020 8, 584, (Oct. 3, 2020), 17 pgs.

Swann, Heather, "Minimal system for assembly of SARS CoV 2 virus like particles", Scientific Reports 10:21877 nature portfolio, (2020), 1-5.

Zhang, Zhikuan, "Structure of SARS-CoV-2 membrane protein essential for virus assembly", nature communications 13:4399, (Aug. 5, 2022), 12 pgs.

"Japanese Application Serial No. 2022-513269, Notification of Reasons for Refusal mailed Feb. 20, 2024", w English translation, 5 pgs.

"U.S. Appl. No. 17/546,835, Restriction Requirement mailed Mar. 20, 2024", 9 pgs.

"European Application Serial No. 17709236.8, Communication Pursuant to Article 94(3) EPC mailed Mar. 14, 2024", 6 pgs.

"Japanese Application Serial No. 2021-536228, Response filed Feb. 22, 2024 to Notification of Reasons for Rejection mailed Aug. 22, 2023", w English claims, 30 pgs.

"Japanese Application Serial No. 2022-144599, Response filed Feb. 22, 2024 to Notification of Reasons for Refusal mailed Aug. 22, 2023", w English claims, 8 pgs.

"Japanese Application Serial No. 2021-546853, Response filed Feb. 29, 2024 to Notification of Reasons for Refusal mailed Aug. 29, 2023", w English claims, 15 pgs.

"Japanese Application Serial No. 2020-182549, Notification of Reasons for Refusal mailed Feb. 20, 2024", w English Translation, 8 pgs.

"U.S. Appl. No. 17/266,049, Non Final Office Action mailed Apr. 12, 2024", 12 pgs.

"U.S. Appl. No. 17/229,001, Notice of Allowance mailed Apr. 24, 2024", 6 pgs.

"Japanese Application Serial No. 2019-171818, Response Filed Mar. 26, 2024 to Notification of Reasons for Rejection mailed Sep. 26, 2023", w English Claims, 21 pgs.

"Japanese Application Serial No. 2022-161803, Response Filed Mar. 12, 2024 to Notification of Reasons for Refusal mailed Sep. 12, 2023", w English Claims, 15 pgs.

"Extending the Stalk Enhances Immunogenicity of the Influenza Virus Neuraminidase", J Virol, vol. 93, No. 18, Article No. e00840-19, (Aug. 29, 2019), 1-12.

"Japanese Application Serial No. 2022-144599, Notification of Reasons for Rejection mailed May 14, 2024", W English Translation, 8 pgs.

"Japanese Application Serial No. 2021-546853, Examiners Decision of Final Refusal mailed May 7, 2024", w English translation, 5 pgs.

"U.S. Appl. No. 17/835,830, Non Final Office Action mailed Jun. 6, 2024", 6 pgs.

"U.S. Appl. No. 17/813,200, Notice of Allowance mailed Jun. 6, 2024", 6 pgs.

"European Application Serial No. 19778696.5, Communication Pursuant to Article 94(3) EPC mailed Jun. 3, 2024", 6 pgs.

"U.S. Appl. No. 17/546,835, Response filed Jun. 6, 2024 to Restriction Requirement mailed Mar. 20, 2024", 9 pgs.

"Japanese Application Serial No. 2022-544779, Examiners Decision of Final Refusal mailed Apr. 23, 2024", w English translation, 5 pgs.

"U.S. Appl. No. 18/525,460, Preliminary Amendment filed Jun. 7, 2024", 6 pgs.

"Japanese Application Serial No. 2024-050083, Voluntary Amendment Filed Apr. 25, 2024", w English Claims, 22 pgs.

"Chinese Application Serial No. 202080025289.6, Office Action mailed May 15, 2024", w English Translation, 18 pgs.

"U.S. Appl. No. 17/813,178, Response filed Jun. 10, 2024 to Non Final Office Action mailed Dec. 13, 2023", 14 pgs.

"U.S. Appl. No. 17/212,836, Non Final Office Action mailed Jun. 13, 2024", 14 pgs.

"U.S. Appl. No. 17/546,967, Response filed Jun. 24, 2024 to Non Final Office Action mailed Mar. 8, 2024", 9 pgs.

"Japanese Application Serial No. 2019-171818, Notification of Reasons for Rejection mailed May 14, 2024", w English Translation, 7 pgs.

"Japanese Application Serial No. 2021-509824, Notification of Reasons for Rejection mailed Jun. 4, 2024", W English Translation, 18 pgs.

"Japanese Application Serial No. 2023-204069, Voluntary Amendment filed Jun. 11, 2024", w English Claims, 9 pgs.

"U.S. Appl. No. 17/813,178, Notice of Allowance mailed Jul. 10, 2024", 5 pgs.

"Japanese Application Serial No. 2022-016436, Response filed Jun. 4, 2024 to Notification of Reasons for Refusal mailed Dec. 5, 2023", w English claims, 12 pgs.

"U.S. Appl. No. 17/229,001, Corrected Notice of Allowability mailed Jul. 22, 2024", 2 pgs.

"International Application Serial No. PCT US2024 020952, International Search Report mailed Jul. 30, 2024", 3 pgs.

"International Application Serial No. PCT US2024 020952, Written Opinion mailed Jul. 30, 2024", 5 pgs.

"Japanese Application Serial No. 2022-161803, Notification of Reasons for Refusal mailed Jun. 4, 2024", w English Translation, 13 pgs.

"U.S. Appl. No. 17/813,178, Corrected Notice of Allowability mailed Jul. 31, 2024", 2 pgs.

"U.S. Appl. No. 17/813,200, Corrected Notice of Allowability mailed Jul. 31, 2024", 2 pgs.

"European Application Serial No. 20714015.3, Communication Pursuant to Article 94(3) EPC mailed Aug. 5, 2024", 4 pgs.

"U.S. Appl. No. 17/835,830, Response filed Aug. 12, 2024 to Non Final Office Action mailed Jun. 6, 2024", 5 pgs.

"U.S. Appl. No. 17/813,200, Corrected Notice of Allowability mailed Aug. 23, 2024", 2 pgs.

"Japanese Application Serial No. 2022-144599, Response filed Aug. 14, 2024 to Notification of Reasons for Rejection mailed May 14, 2024", w English claims, 9 pgs.

"International Application Serial No. PCT US2023 063136, International Preliminary Report on Patentability mailed Sep. 6, 2024", 9 pgs.

"Japanese Application Serial No. 2022-544779, Response filed Aug. 22, 2024 to Examiners Decision of Final Refusal mailed Apr. 23, 2024", w English claims, 20 pgs.

Aria, Yasuha, "PB2 mutations arising during H9N2 influenza evolution in the Middle East confer enhanced replication and growth in mammals", PLOS Pathogens 15(7): e1007919. https: doi.org 10.1371 journal.ppat. 1007919, (Jul. 2, 2019), 25 pages.
Da Silva, V. Diogo, "Assembly of Subtype 1 Influenza Neuraminidase is Driven by Both the Transmembrane and Head Domains", J Biol Chem, vol. 288, No. 1 pp. 644-653, (Jan. 4, 2023), 10 pages.
Fan, Haitian, "Structures of influenza A virus RNA polymerase offer insight into viral genome replication", Nature 573, 287-290 (2019). https: doi.org 10.1038 s41586-019-1530-7, (Sep. 4, 2019), 35 pages.
Giles, Brendan Michael, "Development of a broadly reactive vaccine for highly pathogenic H5N1 influenza", [Online]. Retrieved from the Internet: URL: http: search.proquest.com docview 928138363, (Jan. 11, 2011), 24 pgs.

(56) References Cited

OTHER PUBLICATIONS

Kamiki, Haruhiko, "Novel Biological System with Terminal Sialic Acid Knockout Cells", J Virol 96:e00416-22.https: doi.org 10.1128 jvi.00416-22, (Jul. 18, 2022), 15 pages.

Klimov, A.I., "Correlation of amino acid residues in the M1 and M2 proteins of influenza virus with high yielding properties", Virus Research, vol. 19, Issue 1, 1991, pp. 105-114, ISSN 0168-1702,https: doi.org 10.1016 0168-1702(91)90098-G.(https: www.sciencedirect.com science article pii 016817029190098G), (Mar. 1991), 10 pages.

Ma, Wenjun, "The NS Segment of an H5N1 Highly Pathogenic Avian Influenza Virus (HPAIV) Is Sufficient to Alter Replication Efficiency, Cell Tropism, and Host Range of an H7N1 HPAIV", J Virol. Feb. 2010;84(4):2122-33. doi: 10.1128 JVI.01668-09. Epub Dec. 9, 2009. PMID: 20007264; PMCID: PMC2812369., (Feb. 2010), 12 pages.

Mahesutihan, Madina, "CypA Regulates AIP4-Mediated M1 Ubiquitination of Influenza A Virus", Virologica Sinica 33 (2018): 440-448., (Oct. 16, 2018), 9 pages.

"U.S. Appl. No. 17/352,845, Supplemental Notice of Allowability mailed Sep. 28, 2023", 2 pgs.

"Japanese Application Serial No. 2022-161803, Notification of Reasons for Refusal mailed Sep. 12, 2023", w English Translation, 4 pgs.

"Japanese Application Serial No. 2022-544779, Notification of Reasons for Refusal mailed Aug. 22, 2023", w English Translation, 10 pgs.

"U.S. Appl. No. 17/229,001, Non Final Office Action mailed Oct. 19, 2023", 15 pgs.

"U.S. Appl. No. 17/813,200, Non Final Office Action mailed Oct. 23, 2023", 11 pgs.

"International Application Serial No. PCT US2023 027622, International Search Report mailed Nov. 7, 2023", 5 pgs.

"International Application Serial No. PCT US2023 027622, Written Opinion mailed Nov. 7, 2023", 6 pgs.

"U.S. Appl. No. 16/785,449, Corrected Notice of Allowability mailed Nov. 8, 2023", 10 pgs.

"U.S. Appl. No. 16/785,449, Corrected Notice of Allowability mailed Nov. 17, 2023", 10 pgs.

"Japanese Application Serial No. 2019-171818, Notification of Reasons for Rejection mailed Sep. 26, 2023", w English Translation, 12 pgs.

"U.S. Appl. No. 17/546,967, Response filed Nov. 22, 2023 to Restriction Requirement mailed May 23, 2023", 9 pgs.

"U.S. Appl. No. 17/813,178, Non Final Office Action mailed Dec. 6, 2023", 13 pgs.

Burke, "A Recommended numbering Scheme for Influenza A HA Subtypes", PLOS One. 9, (2014), 6 pgs.

Li, "Selection of antigenically advanced variants of seasonal influenza viruses", Nature Microbiology 1 (6):Supplementary Infiormation, (2016), 10 pgs.

Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906 pdf jvi.02216-21.pdf, (Mar. 23, 2022), 13 pgs.

Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.

Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.

"", Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

"", Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

"", Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.

"", Result 17, NCBI Blast nucleotide search of SEQ ID No. 2, database "nr", (Jul. 18, 2006), 3 pgs.

"", Result 7, NCBI Blast nucleotide search of SEQ ID: 1, database "nr", (Jul. 18, 2006), 3 pgs.

"", FLUMISTTM Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action mailed Jun. 28, 2007", 16 pgs.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"Final O.A Jun. 28, 2007", 5 pgs.

"Application Serial No. 04809419.7, Office Action Mailed Sep. 9, 2009", 3 pgs.

"U.S. Appl. No. 09/834,095, Advisory Action mailed Jan. 8, 2004", 3 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

"U.S. Appl. No. 09/834,095, Response filed Feb. 4, 2003 to Office Action mailed Nov. 4, 2002", 14 pgs.

"U.S. Appl. No. 09/834,095, Response filed Jun. 12, 2003 to Restriction Requirement mailed Apr. 22, 2003", 2 pgs.

"U.S. Appl. No. 09/834,095, Response filed Jun. 18, 2004 to Office Action mailed Apr. 20, 2004", 11 pgs.

"U.S. Appl. No. 09/834,095, Response filed Aug. 1, 2002 to Restriction Requirement mailed Jul. 1, 2002", 3 pgs.

"U.S. Appl. No. 09/834,095, Response filed Nov. 26, 2003 to Final Office Action mailed Aug. 26, 2003", 10 pgs.

"U.S. Appl. No. 09/834,095, Restriction Requirement mailed Apr. 22, 2003", 5 pgs.

"U.S. Appl. No. 09/834,095, Restriction Requirement mailed Jul. 1, 2002", 9 pgs.

"U.S. Appl. No. 09/834,095, Supplemental Amendment filed Aug. 4, 2004", 7 pgs.

"U.S. Appl. No. 10/081,170, Advisory Action mailed Sep. 27, 2004", 3 pgs.

"U.S. Appl. No. 10/081,170, Final Office Action mailed Apr. 12, 2006", 7 pgs.

"U.S. Appl. No. 10/081,170, Final Office Action mailed Jul. 13, 2004", 8 pgs.

"U.S. Appl. No. 10/081,170, Non Final Office Action mailed Jan. 15, 2004", 9 pgs.

"U.S. Appl. No. 10/081,170, Non Final Office Action mailed Feb. 8, 2005", 9 pgs.

"U.S. Appl. No. 10/081,170, Non Final Office Action mailed Aug. 24, 2005", 9 pgs.

"U.S. Appl. No. 10/081,170, Notice of Allowance mailed Sep. 18, 2006", 8 pgs.

"U.S. Appl. No. 10/081,170, Preliminary Amendment filed May 20, 2003", 2 pgs.

"U.S. Appl. No. 10/081,170, Preliminary Amendment filed Jun. 6, 2002", 1 pg.

(56) References Cited

OTHER PUBLICATIONS

"U.S. Appl. No. 10/081,170, Response filed Jan. 24, 2006 to Non Final Office Action mailed Aug. 24, 2005", 11 pgs.
"U.S. Appl. No. 10/081,170, Response filed Apr. 12, 2004 to Non Final Office Action mailed Jan. 15, 2004", 12 pgs.
"U.S. Appl. No. 10/081,170, Response filed Jun. 8, 2005 to Non Final Office Action mailed Feb. 8, 2005", 11 pgs.
"U.S. Appl. No. 10/081,170, Response filed Aug. 17, 2006 to Final Office Action mailed Apr. 12, 2006", 9 pgs.
"U.S. Appl. No. 10/081,170, Response filed Sep. 13, 2004 to Final Office Action mailed Jul. 13, 2004", 10 pgs.
"U.S. Appl. No. 10/081,170, Response filed Oct. 10, 2003 to Restriction Requirement mailed Sep. 10, 2003", 3 pgs.
"U.S. Appl. No. 10/081,170, Restriction Requirement mailed Sep. 10, 2003", 4 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jul. 23, 2003", 4 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment mailed Jun. 5, 2008", 6 pgs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Aug. 2, 2006", 34 pgs.
"U.S. Appl. No. 10/855,875, Final Office Action mailed Dec. 10, 2010", 15 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.
"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.

(56) References Cited

OTHER PUBLICATIONS

"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Sep. 13, 2007 to Restriction Requirement mailed Mar. 13, 2007", 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Non Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179. Response filed Feb. 20, 2013 to Non Final Office Action mailed Nov. 29, 2012", 10 pgs.
"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.

(56) References Cited

OTHER PUBLICATIONS

"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Final Office Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.

"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010", 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.
"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.
"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.

(56) References Cited

OTHER PUBLICATIONS

"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non Final Office Action mailed Jun. 12, 2014", 16 pgs.
"U.S. Appl. No. 12/214,414, Response filed Dec. 21, 2011 to Advisory Action mailed Oct. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/470,287 , Response filed Jan. 23, 2012 to Non Final Office Action mailed Jul. 22, 2011", 13 pgs.
"U.S. Appl. No. 12/470,287 , Response filed May 31, 2012 to Final Office Action mailed Apr. 3, 2012", 14 pgs.
"U.S. Appl. No. 12/470,287, Corrected Notice of Allowability mailed Sep. 11, 2012", 2 pgs.
"U.S. Appl. No. 12/470,287, Final Office Action mailed Apr. 3, 2012", 7 pgs.
"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.

(56) References Cited

OTHER PUBLICATIONS

"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 11", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 15", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action mailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.
"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.

(56) References Cited

OTHER PUBLICATIONS

"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556. PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.
"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020", 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.

(56) References Cited

OTHER PUBLICATIONS

"U.S. Appl. No. 15/247,006 Response filed Jun. 4, 2019 to Final Office Action mailed Feb. 4, 2019", 7 pgs.
"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.

"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.
"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.

(56) References Cited

OTHER PUBLICATIONS

"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.

(56) References Cited

OTHER PUBLICATIONS

"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.
"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/266,049, Non Final Office Action mailed Mar. 14, 2023", 12 pgs.
"U.S. Appl. No. 17/352,845, Non Final Office Action mailed Dec. 16, 2022", 15 pgs.
"U.S. Appl. No. 17/578,939, Non Final Office Action mailed Apr. 21, 2023", 5 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 17/813,200, Preliminary Amendment filed Mar. 7, 23", 10 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2004274860, Office Action mailed May 21, 2008", 2 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Response filed Feb. 3, 2023 to First Examination Report filed Sep. 29, 2022", Claims not amended in response filed, 4 pgs.
"Australian Application Serial No. 2021201844, Voluntary Amendment filed Dec. 6, 2021", 17 pgs.
"Australian Application Serial No. 2021204721, First Examination Report mailed Mar. 16, 2023", 6 pgs.
"Australian Application Serial No. 2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf. html, (Observed Feb. 22, 2003), 2 pgs.
"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazil Application Serial No. PI0307679-2, Office Action mailed May 16, 2017", 2 pgs.

(56) References Cited

OTHER PUBLICATIONS

"Brazil Application Serial No. PI0307679-2, Response filed Jul. 13, 2017 to Office Action mailed May 16, 2017", 9 pgs.

"Brazilian Application Serial No. PI 0307679-2, Office Action published in Patent Gazette No. 1871 of Nov. 14, 2006", 2 pgs.

"Brazilian Application Serial No. PI 0307679-2, Petition filed Jan. 10, 2007 in response to publication dated Nov. 14, 2006", 6 pgs.

"Brazilian Application Serial No. PI 0410702-0, Office Action mailed Nov. 1, 2019", (w/ English Translation), 6 pgs.

"Brazilian Application Serial No. PI 0410702-0, Response filed Feb. 6, 2020 to Office Action mailed Nov. 1, 2019", (w/ English Translation of Claims), 92 pgs.

"Brazilian Application Serial No. PI0307679-2, Final Office Action mailed Jul. 7, 2020", w/o English Translation, 6 pgs.

"Brazilian Application Serial No. PI0307679-2, Office Action mailed May 13, 2019", (w/ English Translation), 17 pgs.

"Brazilian Application Serial No. PI0307679-2, Office Action mailed Oct. 3, 2019", (w/ English Translation), 6 pgs.

"Brazilian Application Serial No. PI0307679-2, Office Action mailed Dec. 20, 2016", 2 pgs.

"Brazilian Application Serial No. PI0307679-2, Response filed Feb. 1, 2017 to Office Action mailed Dec. 20, 2016", 6 pgs.

"Brazilian Application Serial No. PI0307679-2, Response filed Aug. 16, 2019 to Office Action mailed May 13, 2019", (w/ English Translation of Claims), 29 pgs.

"Brazilian Application Serial No. PI0307679-2, Response filed Dec. 11, 2019 to Office Action mailed Oct. 3, 2019", w/ English Claims, 59 pgs.

"Brazilian Application Serial No. PI0410702-0, Office Action mailed Feb. 23, 2012", w/ English Translation, 4 pgs.

"Brazilian Application Serial No. PI0410702-0, Office Action mailed Apr. 1, 2020", (w/ English Summary), 6 pgs.

"Brazilian Application Serial No. PI0410702-0, Response filed May 7, 2012 to Office Action mailed Feb. 23, 2012", w/ English Claims, 11 pgs.

"Brazilian Application Serial No. PI0410702-0, Response filed Aug. 28, 2020 to Office Action mailed Apr. 1, 2020", (w/ English Translation of Claims), 86 pgs.

"Canadian Application Serial No. 11/509,249, Response filed May 16, 2011 to Office Acttion mailed Nov. 18, 2010", 15 pgs.

"Canadian Application Serial No. 2,406,180, Office Action mailed Sep. 9, 2008", 5 pgs.

"Canadian Application Serial No. 2,406,180, Office Action mailed Nov. 10, 2011", 3 pgs.

"Canadian Application Serial No. 2,406,180, Office Action mailed Nov. 23, 2009", 3 pgs.

"Canadian Application Serial No. 2,406,180, Office Action mailed Dec. 10, 2010", 2 Pgs.

"Canadian Application Serial No. 2,406,180, Response filed Jan. 26, 2009 to Official Action mailed Sep. 9, 2008", 22 pgs.

"Canadian Application Serial No. 2,406,180, Response filed May 7, 2012 to Office Action mailed Nov. 10, 2011", 11 pgs.

"Canadian Application Serial No. 2,406, 180, Response filed May 21, 2010 to Office action mailed Nov. 23, 2009", 13 pgs.

"Canadian Application Serial No. 2,406,180, Response filed Jun. 14, 2011 to Office Action mailed Dec. 10, 2010", 10 pgs.

"Canadian Application Serial No. 2,406,180, Response mailed Jun. 10, 2011 to Office Action mailed Dec. 10, 2010", 10 pgs.

"Canadian Application Serial No. 2,492,097, Office Action mailed Jan. 10, 2012", 4 pgs.

"Canadian Application Serial No. 2,492,097, Office Action mailed Apr. 24, 2008", 3 pgs.

"Canadian Application Serial No. 2,492,097, Office Action mailed Jul. 31, 2009", 3 pgs.

"Canadian Application Serial No. 2,492,097, Response filed Jan. 29, 2010 to Office Action mailed Jul. 31, 2009", 13 pgs.

"Canadian Application Serial No. 2,492,097, Response filed May 2, 2012 to Office Action mailed Jan. 10, 2012", 12 pgs.

"Canadian Application Serial No. 2,492,097, Response filed Oct. 23, 2008 to Office Action mailed Apr. 24, 2008", 14 pgs.

"Canadian Application Serial No. 2,522,081, Amendment After Allowance filed Aug. 10, 2012", 3 pgs.

"Canadian Application Serial No. 2,522,081, Office Action filed Nov. 18, 2011", 11 pgs.

"Canadian Application Serial No. 2,522,081, Office Action mailed Jun. 6, 2011", 2 pgs.

"Canadian Application Serial No. 2,522,081, Office Action mailed Aug. 30, 2010", 2 pgs.

"Canadian Application Serial No. 2,522,081, Office Action mailed Oct. 8, 2009", 6 pgs.

"Canadian Application Serial No. 2,522,081, Response filed Feb. 28, 2011 to Office Action mailed Aug. 30, 2010", 10 pgs.

"Canadian Application Serial No. 2,522,081, Response filed Apr. 8, 2010 to Office Action dated Oct. 8, 2009", 30 pgs.

"Canadian Application Serial No. 2,522,081, Response filed Nov. 18, 2011 to Office Action mailed Jun. 6, 2011", 11 pgs.

"Canadian Application Serial No. 2,525,953, Amendment and Response filed Feb. 1, 2017 to Office Action mailed Aug. 1, 2016", 28 pgs.

"Canadian Application Serial No. 2,525,953, Non Final Office Action mailed Mar. 30, 2022", 4 pgs.

"Canadian Application Serial No. 2,525,953, Office Action mailed Jan. 21, 2016", 6 pgs.

"Canadian Application Serial No. 2,525,953, Office Action mailed Jan. 29, 2020", 4 pgs.

"Canadian Application Serial No. 2,525,953, Office Action mailed Apr. 28, 2021", 7 pgs.

"Canadian Application Serial No. 2,525,953, Office Action mailed Jul. 31, 2012", 4 pgs.

"Canadian Application Serial No. 2,525,953, Office Action mailed Aug. 1, 2016", 6 pgs.

"Canadian Application Serial No. 2,525,953, Office Action mailed Aug. 16, 2013", 3 pgs.

"Canadian Application Serial No. 2,525,953, Office Action mailed Oct. 3, 2017", 4 pgs.

"Canadian Application Serial No. 2,525,953, Office Action mailed Nov. 2, 2018", 6 pgs.

"Canadian Application Serial No. 2,525,953, Office Action mailed Nov. 6, 2014", 3 pgs.

"Canadian Application Serial No. 2,525,953, Office Action mailed Jun. 22, 2011", 4 pgs.

"Canadian Application Serial No. 2,525,953, Office Action received Jun. 22, 2011", 4 pgs.

"Canadian Application Serial No. 2,525,953, Response filed Jan. 31, 2013 to Office Action mailed Jul. 31, 2012", 11 pgs.

"Canadian Application Serial No. 2,525,953, Response filed Feb. 1, 2017 to Office Action mailed Aug. 1, 2016", 28 pgs.

"Canadian Application Serial No. 2,525,953, Response filed Feb. 14, 2014 to Office Action mailed Aug. 16, 2013", 16 pgs.

"Canadian Application Serial No. 2,525,953, Response filed Apr. 3, 2018 to Office Action mailed Oct. 3, 2017", 46 pgs.

"Canadian Application Serial No. 2,525,953, Response filed May 1, 2015 to Office Action mailed Nov. 6, 2014", 23 pgs.

"Canadian Application Serial No. 2,525,953, Response filed May 2, 2019 to Office Action mailed Nov. 2, 2018", 31 pgs.

"Canadian Application Serial No. 2,525,953, Response filed May 25, 2020 to Office Action mailed Jan. 29, 2020", 35 pgs.

"Canadian Application Serial No. 2,525,953, Response filed Jul. 11, 2016 to Office Action mailed Jan. 21, 2016", 21 pgs.

"Canadian Application Serial No. 2,525,953, Response filed Aug. 26, 2021 to Office Action mailed Apr. 28, 2021", 16 pgs.

"Canadian Application Serial No. 2,525,953, Response filed Dec. 22, 2011 to Office Action mailed Jun. 22, 2011", 17 pgs.

"Canadian Application Serial No. 2,647,985 , Response filed Sep. 30, 2013 to Office Action mailed May 15, 2013", 20 pgs.

"Canadian Application Serial No. 2,647,985, Office Action mailed May 15, 2013", 3 pgs.

"Canadian Application Serial No. 2,816,242, Office Action mailed Jun. 16, 2014", 3 pgs.

"Canadian Application Serial No. 2,816,242, Office Action mailed Jul. 12, 2017", 4 pgs.

"Canadian Application Serial No. 2,816,242, Office Action mailed Sep. 16, 2016", 4 pgs.

(56) References Cited

OTHER PUBLICATIONS

"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Offiice Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.
"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.
"Chinese Application Serial No. 201310400039.8, Office Action Response mailed Jun. 16, 2017", W / English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.

(56) References Cited

OTHER PUBLICATIONS

"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims, 11 pgs.
"Chinese Application Serial No. 201310400039.8, Response filed Aug. 7, 2017 to Office Action Response mailed Jun. 16, 2017", W/ English Claims, 10 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims), 17 pgs.
"Chinese Application Serial No. 201780024821.0, Response filed Aug. 30, 2022 to Office Action mailed Jun. 15, 2022", w/ English Claims, 18 pgs.
"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Chinese Application Serial No. 200480021259.9, Office Action mailed May 8, 2009", (w/ English Translation), 6 pgs.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application No. 200501890, Notice of Allowance mailed Jun. 23, 2009", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action mailed Sep. 4, 2008", (w/ English Translation of Claims), 14 pgs.
"Eurasian Application Serial No. 200701097, Office Action mailed Sep. 4, 2008", OAR-MISC, 2 pgs.
"Eurasion Application Serial No. 200701097, Office Action mailed Jun. 16, 2009", 3 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161(1) and 162 EPC mailed Oct. 19, 2018", 9 pgs.
"European Application Serial No. 21705801.5, Response to Communication pursuant to Rules 161 and 162 filed Mar. 28, 2023", 13 pgs.
"European Application Serial No. 03716017.3, Office Action mailed Aug. 23, 2012", 4 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action mailed Oct. 1, 2009", 11 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 4, 11 to Office Action mailed Jul. 27, 10", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 2022, 09", 17 pgs.
"European Application Serial No. 04750333.9, Summons to Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.

(56) References Cited

OTHER PUBLICATIONS

"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 04809419.7, Communication mailed Apr. 3, 2007", 3 pgs.
"European Application Serial No. 04809419.7, Response filed Oct. 19, 2007 to Communication mailed Apr. 3, 2007", 20 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Response filed Sep. 8, 2016 to Office Action mailed May 2, 2016", 69 pgs.
"European Application Serial No. 10777154.5, Summons to Attend Oral Proceedings mailed Jan. 7, 2019", 5 pgs.
"European Application Serial No. 12761841.1, Communication pursuant to Article 94(3) EPC mailed Dec. 23, 2016", 6 pgs.

"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Office Action mailed Feb. 23, 2016", 2 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 14745060.5, Response filed Dec. 22, 2016 to Communication pursuant to Rules 161(1) and 162 EPC mailed Feb. 23, 2016", 6 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 2018 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.

(56) References Cited

OTHER PUBLICATIONS

"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Evaluation of Medicines for human Use", EMEA/CPMP/BWP/2289/01, London the European Agency for the Evaluation of Medicinal Products, Committee for Proprietary Medicinal Products (CPMP), (Feb. 20, 2003), 14.
"Fluzone Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1))], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.

"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Indian Application Serial No. 2388/KOLNP/2005, First Examination Report mailed Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) rna", Database EM_VI E.B.I. Hinxton U.K., (Jun. 13, 1985), 10 pgs.
"Influenza virus A/CHR/ 157/83 genomic RNA for haemagglutinin", (2012), 2 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Response filed Sep. 9, 2002 to Written Opinion mailed Aug. 7, 2002", 12 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.

(56) References Cited

OTHER PUBLICATIONS

"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.

(56) References Cited

OTHER PUBLICATIONS

"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report on Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 171372, Office Action mailed Feb. 21, 2010", w/English Translation, 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 2012", w/English Claims, 54 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct. 18, 2015", w/English Claims, 4 pgs.
"Israeli Application Serial No. 211324, Response filed Mar. 31, 2015 to Office Action mailed Sep. 8, 2014", w/English Translation, 21 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Apr. 14, 2016", (English Translation), 3 pgs.
"Israeli Application Serial No. 238584, Office Action mailed Aug. 23, 2018", (w/ English Translation), 6 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims), 10 pgs.
"Israeli Application Serial No. 171372, Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2022-144599, Voluntary Amendment filed Nov. 9, 2022", w/ English Claims, 14 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.

(56) References Cited

OTHER PUBLICATIONS

"Japanese Application Serial No. 2003-568038, Office Action mailed Jul. 21, 2005", w/out English Translation, 3 pgs.

"Japanese Application Serial No. 2003-568038, Request for Examination filed Aug. 19, 2005 in Response to Official Action mailed Jul. 21, 2005", (w/ Partial English Translation of Specification), 8 pgs.

"Japanese Application Serial No. 2003-568038, Response filed Sep. 14, 2009 to Office Action mailed May 15, 2009", (w/ English Translation of Amended Claims), 10 pgs.

"Japanese Application Serial No. 2003-568038, Response filed Dec. 10, 2008 to Office Action mailed Jul. 10, 2008", (w/ English Translation of Amended Claims), 15 pgs.

"Japanese Application Serial No. 2006-513125, Office Action mailed Mar. 9, 2010", (English Translation), 11 pgs.

"Japanese Application Serial No. 2006-513125, Response filed Aug. 30, 2010 to Office Action mailed Mar. 9, 2010", (w/ English Translation of Amended Claims), 60 pgs.

"Japanese Application Serial No. 2006-533439, Decision of Final Rejection mailed Aug. 14, 2012", (w/ English Translation), 5 pgs.

"Japanese Application Serial No. 2006-533439, Office Action mailed Mar. 9, 2010", (w/ English Translations), 20 pgs.

"Japanese Application Serial No. 2006-533439, Office Action mailed Mar. 27, 2012", w/ English Translation, 8 pgs.

"Japanese Application Serial No. 2006-533439, Response filed May 21, 2012 to Office Action mailed Mar. 27, 2012", (w/ English Translation of Amended Claims), 19 pgs.

"Japanese Application Serial No. 2006-533439, Response filed Aug. 3, 2011 to Office Action mailed Feb. 15, 2011", (w/ English Translation of Amended Claims), 18 pgs.

"Japanese Application Serial No. 2006-533439, Office Action mailed Feb. 15, 2011", (w/ English Translation), 13 pgs.

"Japanese Application Serial No. 2006-533439; Office Action Response filed Jul. 9, 2010", (w/ English Translation of Claims), 25 pgs.

"Japanese Application Serial No. 2008-315106, Office Action mailed Jun. 24, 2009", (w/ English Translation), 10 pgs.

"Japanese Application Serial No. 2008-315106, Response filed Oct. 15, 2009 to Office Action mailed Jun. 24, 2009", w/English Translation, 103 pgs.

"Japanese Application Serial No. 2008-315106, Response filed Oct. 15, 2009 to Office Action mailed Jun. 24, 2009", (w/ English Translation of Amended Claims), 103 pgs.

"Japanese Application Serial No. 2008-315106, Response filed Dec. 3, 2009 to Office Action mailed Jun. 24, 2009", (w/ English Translation of Claims), 9 pgs.

"Japanese Application Serial No. 2009-238781, Office Action mailed Oct. 11, 2011", (w/ English Translation), 3 pgs.

"Japanese Application Serial No. 2009-502945, Examiners Decision of Final Refusal mailed Nov. 12, 2013", (w/ English Translation), 8 pgs.

"Japanese Application Serial No. 2009-502945, Office Action mailed Oct. 23, 2012", (w/ English Translation), 16 pgs.

"Japanese Application Serial No. 2009-502945, Response filed Apr. 10, 2013 to Office Action mailed Oct. 23, 2012", (w/ English Translation of Claims), 18 pgs.

"Japanese Application Serial No. 2011-111048, Office Action mailed Jun. 25, 2013", (w/ English Translation), 7 pgs.

"Japanese Application Serial No. 2011-111048, Office Action mailed Sep. 18, 2012", (w/ English Translation), 10 pga.

"Japanese Application Serial No. 2011-111048, Response filed Sep. 25, 2012 to Office Action mailed Jun. 25, 2013", (w/ English Translation of Amended Claims), 18 pgs.

"Japanese Application Serial No. 2011-111048. Response filed Mar. 15, 2013", (w/ Translation of Amended Claims), 14 pgs.

"Japanese Application Serial No. 2012-273898, Office Action mailed Jun. 10, 2014", (w/ English Translation), 7 pgs.

"Japanese Application Serial No. 2012-273898, Response filed Sep. 4, 2014 to Office Action mailed Jun. 10, 2014", W/ English Claims, 9 pgs.

"Japanese Application Serial No. 2012-536963, Amendment and Argument filed Jun. 26, 2015 to Office Action mailed Jan. 6, 2015", (w/ English Translation of Amended Claims), 12 pgs.

"Japanese Application Serial No. 2012-536963, Examiners Decision of Final Refusal mailed Nov. 17, 2015", (w/ English Translation), 8 pgs.

"Japanese Application Serial No. 2012-536963, Office Action mailed Jan. 6, 2015", (w/ English Translation), 14 pgs.

"Japanese Application Serial No. 2012-536963, Voluntary Amendment filed Jun. 27, 2012", (w/ English Translation of Amended Claims), 17 pgs.

"Japanese Application Serial No. 2013-198377, Office Action mailed Jan. 6, 2015", (w/ English Translation), 9 pgs.

"Japanese Application Serial No. 2014-049025 Response filed Sep. 4, 2015 to Office Action mailed Jun. 16, 2015", (w/ Amended Claims), 12 pgs.

"Japanese Application Serial No. 2014-049025, Examiners Decision of Final Refusal mailed Feb. 2, 2016", W/ English Translation, 5 pgs.

"Japanese Application Serial No. 2014-049025, Office Action mailed Jun. 16, 2015", (w/ English Translation), 6 pgs.

"Japanese Application Serial No. 2014-527339, Examiners Decision of Final Refusal mailed Feb. 7, 2017", (w/ English Translation), 5 pgs.

"Japanese Application Serial No. 2014-527339, Office Action mailed May 31, 2016", (w/ English Translation), 10 pgs.

"Japanese Application Serial No. 2014-527339, Response filed Sep. 16, 2016 to Office Action mailed May 31, 2016", (w/ English Translation of Amended Claims), 33 pgs.

"Japanese Application Serial No. 2016-053990, Office Action mailed Jun. 6, 2017", (w/ English Translation), 4 pgs.

"Japanese Application Serial No. 2016-053990, Response filed Dec. 6, 2017 to Office Action mailed Jun. 6, 2017", (w/ English Translation of Amended Claims), 14 pgs.

"Japanese Application Serial No. 2016-110879, Office Action mailed May 30, 2017", (w/ English Translation), 7 pgs.

"Japanese Application Serial No. 2016-110879, Response filed Nov. 30, 2017 to Office Action mailed May 30, 2017", (w/ English Translation of Claims), 25 pgs.

"Japanese Application Serial No. 2016-527046, Examiners Decision of Final Refusal mailed May 21, 2019", (w/ English Translation), 20 pgs.

"Japanese Application Serial No. 2016-527046, Reasons for Rejection mailed Aug. 14, 2018", (w/ English Translation), 14 pgs.

"Japanese Application Serial No. 2016-527046, Response Filed Dec. 4, 2018 to Reasons for Rejection mailed Aug. 14, 2018", (w/ English Translation of Amended Claims), 18 pgs.

"Japanese Application Serial No. 2017-111526, Office Action mailed May 14, 2019", (w/ English Translation), 6 pgs.

"Japanese Application Serial No. 2017-111526, Office Action mailed Jun. 26, 2018", (w/ English Translation), 5 pgs.

"Japanese Application Serial No. 2017-111526, Response Filed Dec. 21, 2018 to Office Action mailed Jun. 26, 2018", (w/ English Translation of Amended Claims), 7 pgs.

"Japanese Application Serial No. 2018-510751, Examiners Decision of Final Refusal mailed Dec. 17, 2019", w/ English Translation, 10 pgs.

"Japanese Application Serial No. 2018-510751, Notification of Reasons for Refusal mailed Mar. 13, 2019", (w/ English Translation), 14 pgs.

"Japanese Application Serial No. 2018-510751, Response filed Apr. 17, 2020 to Examiners Decision of Final Refusal mailed Dec. 17, 2019", w/ English Claims, 7 pgs.

"Japanese Application Serial No. 2018-510751, Response filed Aug. 9, 2019 to Notification of Reasons for Refusal mailed Mar. 13, 2019", (w/ English Translation of Claims), 24 pgs.

"Japanese Application Serial No. 2018-543688, Notification of Reasons for Rejection mailed Oct. 29, 2019", w/ English Translation, 14 pgs.

"Japanese Application Serial No. 2018-543688, Office Action mailed Jun. 30, 2020", w/ English translation, 11 pgs.

(56) References Cited

OTHER PUBLICATIONS

"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Preliminary Examination Report mailed Jan. 17, 2023", w/ English Translation, 3 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs.
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-146743, Response filed Feb. 17, 2023 to Notification of Reasons for Rejection mailed Aug. 17, 2022", w/ English Claims, 34 pgs.
"Japanese Application Serial No. 2021-506434, Examiners Decision of Final Refusal mailed Jan. 10, 2023", w/ English Translation, 10 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Japanese Application Serial No. 2006-513125, Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Actiion mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.

(56) References Cited

OTHER PUBLICATIONS

"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 2 pgs.
"New Zealand Application Serial No. 555245, Subsequent Examiner Report mailed Jul. 3, 2009", 1 pg.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 20056074, Office Action Response mailed Apr. 1817", W/ English Claims, 27 Pgs.
"Norway Application Serial No. 20056074, Response filed Jul. 25, 2017 to Office Action mailed Apr. 25, 2017", (w/ English Translation of Amended Claims), 111 pgs.
"Norweigan Application Serial No. 20056074, Office Action mailed Apr. 25, 2017", (Translation), 3 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase acidic [influenza A virus (A/swine/Shizuoka/120/97(H3N2))]", GenBank AAO15329.1, (2003), 1 pg.
"Polymerase PA [Influenza A virus (A/swine/Yangzhou/1/2008(H9N2))]", GenBank: ADK98493.1, [Online]. Retrieved from the Internet: <URL: https://www.ncbi.nlm.nih.gov/protein/ADK98493.1/>, 2 pgs.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.
"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.

(56) References Cited

OTHER PUBLICATIONS

"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nlm, [Online]. Retrieved from the Internet: <URL: https://www.ncbi.nlm.nih.gov/gene/47853> Sep. 14, 2022, (Aug. 17, 2022), 14 pgs.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.
Abram, M. E, et al., "Nature, position, and frequency of mutations made in a single cycle of HIV-1 replication", J Virol., 84(19), (Oct., 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", Embo J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Bancroft, C. T, et al., "Evidence for segment-nonspecific packaging of the influenza a virus genome", J Virol., 76(14), (Jul., 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", Embo J., 16(9), (May 1, 1997), 2376-83.
Betakova, T., et al., "The NB protein is an integral component of the membrane of influenza B virus.", J Gen Virol., 77 ( Pt 11), (Nov., 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb., 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20):e01100-18, (Oct. 2018), 1-13.
Brooke, C B, "Biological activities of 'noninfectious' influenza A virus particles", Future Virol 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Brown, Ta, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.

(56) References Cited

OTHER PUBLICATIONS

Buchholz, U. J., et al., "Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter", Journal of Virology, 73(1), (1999), 251-259.

Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.

Bukreyev, A., et al., "Recovery of infectious respiratory syncytial virus expressing an additional, foreign gene", Journal of Virology, 70(10), (Oct., 1996), 6634-6641.

Bullido, R., et al., "Influenza A Virus NEP (NS2 protein) Downregulates RNA Synthesis of Model Template RNAs", Journal of Virology, 75(10), (May 2001), 4912-4917.

Bullido, R., et al., "Influenza A virus NEP(NS2 protein) downregulates RNA synthesis of model template RNAs", Journal of Virology, vol. 75 4912-4917, (May 2001), 6 pgs.

Burmeister, W. P., et al., "The 2.2 A resolution crystal structure of influenza B neuraminidase and its complex with sialic acid", The EMBO Journal, 11(1), (1992), 49-56.

Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.

Cao, S., et al., "Characterization of the Nucleocytoplasmic Shuttle of the Matrix Protein of Influenza B Virus", Journal of Virology., 88(13), (Jul. 2014), 7464-7473.

Cardona, C. J., "Avian Influenza", http://www.vetmed.ucdavis.edu/vetex/INF-PO_AvianInfluenzaFS.html, ((Observed Feb. 22, 2003), 3 pgs.

Castrucci, M. R, et al., "Attenuation of Influenza A Virus by Insertion of a Foreign Epitope into the Neuraminidase", Journal of Virology, 66(8), (1992), 4647-4653.

Castrucci, M. R., et al., "Biologic Importance of Neuraminidase Stalk Length in Influenza A Virus", Journal of Virology, 67(2), (1993), 759-764.

Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.

Castrucci, Maria R., et al., "Reverse genetics system for generation of an influenza A virus mutant containing a deletion of the carboxyl-terminal residue of M2 protein.", J Virol., 69(5), (May 1995), 2725-8.

Catchpole, A P, et al., "Alternative base pairs attenuate influenza A virus when introduced into the duplex region of the conserved viral RNA promoter of either the NS or the PA gene", Journal of General Virology, 84, (2003), 507-515.

Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.

Chang, M. W., et al., "Analysis of HIV Wild-Type and Mutant Structures via in Silico Docking against Diverse Ligand Libraries", J. Chem. Inf. Model., 47(3), (2007), 1258-1262.

Chen, H, et al., "Generation and evaluation of a high-growth reassortant H9N2 influenza A virus as a pandemic vaccine candidate", Vaccine, 21(17-18), (May 16, 2003), 1974-9.

Chen, Z., et al., "Influenza A Virus NS1 Protein Targets Poly(A)-Binding Protein II of the Cellular 3'-End Processing Machinery", The EMBO Journal, 18(8), (1999), 2273-2283.

Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.

Chiba, Shiho, et al., "Multivalent nanoparticle-based vaccines protect hamsters against SARS-CoV-2 after a single immunization", Communications Biology, 4: 597, (2021), 1-9.

Cho, Alice, et al., "Implications of Broadly Neutralizing Antibodies in the Development of a Universal Influenza Vaccine", Current Opinion in Virology, vol. 17 110-115, (Apr. 1, 2016), 6 pgs.

Chothia, Cyrus, et al., "Canonical Structures for the Hypervariable Regions of Immunoglobulins.", J Mol Biol., 196(4), (1987), 901-917.

Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.

Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.

Claas, E C. J., et al., "Human Influenza A H5N1 Virus Related to a Highly Pathogenic Avian Influenza Virus", The Lancet, 351, (1998), 472-477.

Clarke, D. K., et al., "Rescue of Mumps Virus From cDNA", Journal of Virology, 74(10), (2000), 4831-4838.

Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).

Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.

Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K.-K., "Genetic manipulation of non-segmented negative-strand RNA viruses", Journal of General Virology, 77(Pt. 3), (Mar., 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.

Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.

Cunningham, Brian C, et al., "High-Resolution Epitope Mapping of hGH-Receptor Interactions by Alanine-Scanning Mutagenesis", Science 244:4908, (1989), 6 pgs.

Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.

Daddario-Dicaprio, K. M, et al., "Cross-protection against Marburg virus strains by using a live, attenuated recombinant vaccine", J Virol., 80(19), (Oct., 2006), 9659-66.

(56) References Cited

OTHER PUBLICATIONS

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogs of genome RNA of human parainfluenza virus type 3", Virology, 196(1), (Sep. 1993), 344-348.

De, B. P., et al., "Reverse Genetics of Negative Strand RNA Viruses", Indian Journal of Biochemistry & Biophysics, 31, (1994), 367-375.

De Filette, Marina, et al., "An influenza A vaccine based on tetrameric ectodomain of matrix protein 2", J Biol Chem. 2008 ; 283 (17):, (Feb. 5, 2008), 11382-7.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

Del Guidice, G., et al., "What are the limits of adjuvanticity?", (Abstract), Vaccine, 20(Suppl 1), S38-S41, (2001), 1 pg.

Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.

Desselberger, Ulrich, et al., "The 3' and 5'-terminal sequences of influenza A, B and C virus RNA segments are highly conserved and show partial inverted complementarity", Gene, 8 (3), (Feb. 1980), 315-328.

Dimmock, Nigel J, et al., "In vivo antiviral activity: defective interfering virus protects better against virulent Influenza A virus than avirulent virus", Journal of General Virology 87, (Jan. 8, 2006), 1259-1265.

Dimock, K., et al., "Rescue of Synthetic Analogs of Genomic RNA and Replicative-Intermediate RNA of Human Parainfluenza Virus Type 3", Journal of Virology, 67(5), (1993), 2772-2778.

Dollenmaier, G., et al., "Membrane-Associated Respiratory Syncytial Virus F Protein Expressed From a Human Rhinovirus Type 14 Vector Is Immunogenic", Virology, 281(2), (Mar. 15, 2001), 216-230.

Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.

Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.

Du, Q., "Ribozyme Enzymology", http://academic.brooklyn.cuny.edu/chem/zhuang/QD/toppage1.htm, (Observed Feb. 25, 2003), 8 pgs.

Duff, K. C., et al., "The secondary structure of influenza A M2 transmembrane domain", FEBS Letters, 311 (3), (Oct. 1992), pp. 256-258.

Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.

Duhaut, S., et al., "Approximately 150 Nucleotides from the 5' End of an Influenza a segment 1 Defective Virion RNA are needed for Genome Stability during passage of Defective Virus in Infected Cells", Virology, 275(2) 278-285 Academic Press, Orlando, US, (Sep. 30, 2000), 8 pgs.

Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.

Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.

Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.

Dumoulin, Mireille, et al., "Single-domain antibody fragments with high conformational stability", Protein Science, 11, (2002), 500-515.

Dunham, Eleca J., et al., "Different Evolutionary Trajectories of European Avian-Like and Classical Swine H1N1 Influenza A Viruses", Journal of Virology, 83(11), (Jun. 2009), 5485-5494.

Dunn, E. F., et al., "Transcription of a recombinant bunyavirus RNA template by transiently expressed bunyavirus proteins", Virology, 211(1), (1995), 133-143.

Durbin, A. P, et al., "Human Parainfluenza Virus Type 3 (PIV3) Expressing the Hemagglutinin Protein of Measles Virus Provides a Potential Method for Immunization Against Measles Virus and PIV3 in Early Infancy", Journal of Virology, 74(15), (Aug. 2000), 6821-6831.

Durbin, A. P., et al., "Recovery of infectious human parainfluenza virus type 3 from cDNA", Virology, 235(2), (Sep. 1, 1997), 323-332.

Dyall, J., et al., ""Identification of inhibitors of Ebola virus with a subgenomic replication system "", Antiviral Research, 70(1), 19th International Conference on Antiviral Research, San Juan, PR (May 7-11, 20006), (May 2006), p. A39.

Elhefnawi, M, et al., "Identification of novel conserved functional motifs across most Influenza A viral strains", Virology Journal, 8:44, (2011), 10 pages.

Elliott, R. M., "Emerging Viruses: The Bunyaviridae", Molecular Medicine, 3(9), (1997), 572-577.

Elliott, R. M., et al., "Rescue of Infectious Bunyavirus Entirely From Cloned cDNA", 10th International Conference on Negative Strand Virus, (Abstract No. 96), (1997), 1 pg.

Elliott, R. M., et al., "Some Highlights of Virus Research in 1990", Journal of General Virology, 72(Part 8), (1991), 1761-1779.

Emerson, S. U., et al., "Both NS and L Proteins are Required for in Vitro RNA Synthesis by Vesicular Stomatitis Virus", Journal of Virology, 15(6), (1975), 1348-1356.

Enami, K., et al., "Influenza virus NS1 protein stimulates translation of the M1 protein", Journal of Virology, 68 1432-1437, (1994), 6 pgs.

Enami, M., "An Influenza Virus Containing Nine Different RNA Segments", Virology, 185(1), (1991), 291-298.

Enami, M., et al., "High-Efficiency Formation of Influenza Virus Transfectants", Journal of Virology, 65(5), (1991), 2711-2713.

Enami, M., et al., "Introduction of Site-Specific Mutations Into the Genome of Influenza Virus", Proc. Natl. Acad. Sci. USA, 87, (1990), 3802-3805.

Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.

Enterlein, S., et al., "Untersuchungen zur Replikation und Transkription von Marburgund Ebolavirus", [Online]. 2005, Philipps-Universitat Marburg , Xp002563470, Retrieved from the Internet: <URL:http://deposit.ddb.de/cgi-bin/dokserv?>idn=977005607&dok_var=d1&dok_ext=pdf&filenAme=977005607 .pdf>[retrieved on Jan. 15, 2010], (2005), p. 70-p. 84.

Essere, Boris, et al., "Critical role of segment-specific packaging signals in genetic reassortment of influenza A viruses", Proc. Natl. Acad. Sci. USA, 110(40), (2013), E3840-E3848.

Fahey, J. L., et al., "Status of Immune-Based Therapies in HIV Infection and Aids", Clinincal and Experimental Immunology, 88(1), (1992), 1-5.

Fan, J, et al., "Preclinical study of influenza virus A M2 peptide conjugate vaccines in mice, ferrets, and rhesus monkeys", Vaccine, 22, (2004), 2993-3003.

(56) References Cited

OTHER PUBLICATIONS

Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. Vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.

Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday. com, (Feb. 20, 2003), 3 pgs.
Genbank, "", ABD36884.1, (2007), 2 pgs.
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov. 1999), 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is the Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Goto, Hideo, et al., "The Genome-Packaging Signal of the Influenza A Virus Genome Comprises a Genome Incorporation Signal and a Genome-Bundling Signal", Journal of Virology; vol. 87 Number 21, (Nov. 2013), 11316-11322.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec., 1992), 541-549.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus

(56) References Cited

OTHER PUBLICATIONS in vitro", Antiviral Research, Elsevier BV, NL, vol. 63, No. 3, XP004580000 ISSN: 0166-3542, (Sep. 1, 2004), 209-215.

Hagen, M., et al., "Recombinant Influenza Virus Polymerase: Requirement of both 5' and 3' Viral Ends for Endonuclease Activity", Journal of Virology, 68(3), (1994), 1509-1515.

Hai, Rong, et al., "Influenza B Virus NS1-Truncated Mutants: Live-Attenuated Vaccine Approach", Journal of Virology, 82(21), (2008), 10580-10590.

Halfmann, P., et al., "Generation of biologically contained Ebola viruses", Proceedings of the National Academy of the National Academy of Sciences of the United States of America 1129-1133, vol. 105, No. 4, XP002563467 ISSN: 1091-6490 the whole document, (Jan. 29, 2008), 6 pgs.

Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.

Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.

Halstead, Scott B,, et al., "Dengue Antibody-Dependent Enhancement: Knowns and Unknowns", Microbiology Spectrum, 2(6), (2014), 1-18.

Harding, Alfred T, et al., "Rationally Designed Influenza Virus Vaccines That are Antigenically Stable during Growth in Egg", MBIO, vol. 8, No. 3, e00669-17, (Jul. 5, 2017), 1-16.

Harmsen, M. M., et al., "Properties, production, and applications of camelid single-domain antibody fragments", Appl Microbiol Biotechnol, 77, (2007), 13-22.

Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.

Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.

Harvey, K. F, et al., "All three WW domains of murine Nedd4 are involved in the regulation of epithelial sodium channels by intracellular Na+.", J Biol Chem., 274(18), (Apr. 30, 1999), 12525-30.

Hatada, E., et al., "Binding of Influenza A Virus NS1 Protein to dsRNA in vitro", Journal of General Virology, 73, (1992), 3325-3329.

Hatakeyama, S., et al., "Dissection and identification of regions required to form pseudoparticles by the interaction between the nucleocapsid (N) and membrane (M) proteins of SARS coronavirus", Virology, 380(1), (2008), 99-108.

Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.

Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.

Hatta, M., et al., "The NB protein of influenza B virus is not necessary for virus replication in vitro", Journal of Virology, 77(10), (May 2003), 6050-6054.

Hay, A. J., et al., "The role of the M2 protein in influenza A virus infection", Proceedings of the International Conference on Options for the Control of Influenza, Courchevel, (1992), 281-288.

He, B., et al., "Recovery of infectious SV5 from cloned DNA and expression of a foreign gene", Virology, 237(2), (1997), 249-260.

He, X., et al., "Generation of SARS-CoV-2 reporter replicon for high-throughput antiviral screening and testing", Proc. Natl. Acad. Sci. USA, 118(15): e2025866118, (2021), 8 pgs.

Helenius, A., "Unpacking the Incoming Influenza Virus", Cell, 69, (May 1992), pp. 577-578.

Hevey, Michael, et al., "Marburg virus vaccines based upon alphavirus replicons protect guinea pigs and nonhuman primates", Virology, 251(1), (Nov. 10, 1998), 28-37.

Hickman, Danielle, et al., "An avian live attenuated master backbone for potential use in epidemic and pandemic influenza vaccines", Journal of General Virology, 89(Part 11), (2008), 2682-2690.

Hiromoto, Y., et al., "Phylogenetic Analysis of the Three Polymerase Genes (PB1, PB2 and PA) of Influenza B Virus", Journal of General Virology, 81, (Apr., 2000), 929-937.

Hiti, A. L., et al., "P03470—Neuraminidase", Entrez Protein Database, http://www.ncbi.nlm.nih.gov/entrez/viewer.fcgi?db=protein&val=84028231, (1982), 730-734.

Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).

Ho, Y., et al., "Assembly of human severe acute respiratory syndrome coronavirus-like particles", Biochem Biophys Res Commun, 318(4), (2004), 833-838.

Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.

Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.

Hoffman, E., et al., "Ambisense Approach for the Generation of Influenza A Virus: vRNA and mRNA Synthesis from One Template", Virology 267(2) 310-317, (Feb. 15, 2006), 8 pgs.

Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.

Hoffman, M. A., et al., "An Infectious Clone of Human Parainfluenza Virus Type 3", Journal of Virology, 71(6), (1997), 4272-4277.

Hoffmann, E., et al., "A DNA transfection system for generation of influenza A virus from eight plasmids", Proc Natl Acad Sci U S A., 97(11), (May 23, 2000), 6108-13.

Hoffmann, E., et al., "Ambisense Approach for the Generation of Influenza A Virus: vRNA and mRNA Synthesis from One Template", Virology, 267, (2000), 310-317.

Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.

Hoffmann, E., et al., "Rescue of Influenza B Virus from Eight Plasmids", Proceedings of the National Academy of Sciences of USA, National Academy of Science, 99(17), (Aug. 20, 2002), 11411-11416.

Hoffmann, Erich, et al., "A Dna transfection system for generation of influenza A virus from eight plasmids", Proceedings of the National Academy of Sciences, vol. 97, No. 11, (2000), 6108- 6113.

Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.

Holsinger, L. J., et al., "Influenza A Virus M2 Ion Channel Protein: a Structure-Function Analysis", Journal of Virology, 68 (3), (1994), pp. 1551-1563.

Honda, A., et al., "RNA Polymerase of Influenza Virus: Role of NP in RNA Chain Elongation", The Journal of Biochemistry, 104(6), (1988), 1021-1026.

Honda, Ayae, et al., "Differential Roles of Viral RNA and cRNA in Functional Modulation of the Influenza Virus RNA Polymerase", The Journal of Biological Chemistry, 276(33), (2001), 31179-31185.

(56) References Cited

OTHER PUBLICATIONS

Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huang, Y., et al., "Generation of Synthetic Severe Acute Respiratory Syndrome Coronavirus Pseudoparticles: Implications for Assembly and Vaccine Production", J. Virol,, 78(22) 12557-12565, (Nov. 2004), 9 pgs.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 'abstract, (Feb. 1999), 240-247.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Huisman, W., et al., "Vaccine-induced enhancement of viral infections", Vaccine, 27(4), (2009), 505-512.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. (103), (2004), 205-211.
Hutchinson, Edward C., et al., "Genome packaging in influenza A virus", Journal of General Virology, 91(Pt 2), (2010), 313-328.
Hwang, Jung-Shan, et al., "Expression of Functional Influenza Virus RNA Polymerase in the Methylotrophic Yeast Pichia pastoris", Journal of Virology, 74(9), (2000), 4074-4084.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.

Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun., 2006), 5233-40.
Jackson, et al., "Characterization of recombinant influenza B viruses with key neuraminidase inhibitor resistance mutations,", Journal of Antimicrobial Chemotherapy, vol. (55), (2005), 162-169.
Jackson, D., et al., "A reverse genetics approach for recovery of recombinant influenza B viruses entirely from cDNA.", J Virol., 76(22), (Nov., 2002), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Ju, X., et al., "A novel cell culture system modeling the SARS-CoV-2 life cycle", PloS Pathogens, 17(3): e1009439, (2021), 23 pgs.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Identification by siRNA of host proteins involved in Ebolavirus replication", Great Lakes Regional Center of Excellence for Biodefense and Emergin Infectious Deseases Research, [Online];

(56) References Cited

OTHER PUBLICATIONS

Retrieved from the Internet: URL:http://www.rcebiodefense.org/glrce/docs/2007/Kawaoka.pdf> [retrieved on Jan. 13, 2010] p. 10, under item C,-& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007/> [retrieved on Jan. 14, 2010] -& Kawaoka Y.;, (2007), pp. 1-19.
Kawaoka, Y., "Mutant Cells With Altered Sialic Acid", U.S. Appl. No. 11/644,179 filed Dec. 22, 2006, 51 pgs.
Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/glrce/annualmeeting/2007Agenda.pdf>, (Nov. 29, 2007), 4 pgs.
Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kilbourne, E. D, et al., "Related studies of a recombinant influenza-virus vaccine. I. Derivation and characterization of virus and vaccine", J Infect Dis., 124(5), (Nov., 1971), 449-62.
Kim, H., et al., "Cold adaptation generates mutations associated with the growth of influenza B vaccine viruses", Vaccine, 33(43), (2015), 5786-5793.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kimura, N., et al., "An in Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an Influenza A Virus Vector Expressing Biologically Active Human Interleukin-2 from the NS Gene Segment", Journal of Virology, 79(16), (Aug. 2005), 10672-10677.
Kobayashi, H., et al., "A replication-incompetent influenza virus bearing the HN glycoprotein of human parainfluenza virus as a bivalent vaccine", Vaccine, 31(52), (2013), 6239-6246.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Kon, Theone C, et al., "Influenza Vaccine Manufacturing: Effect of Inactivation, Splitting and Site of Manufacturing. Comparison of Influenza Vaccine Production Processes", PLoS ONE, 11(3), e0150700, (Mar. 9, 2016), 19 pgs.
Konarska, M. M., et al., "Structure of RNAs Replicated by the DNA-Dependent T7 RNA Polymerase", Cell, 63(2), (1990), 609-618.
Konduru, K., et al., "Ebola virus glycoprotein Fc fusion protein confers protection against lethal challenge in vaccinated mice", Vaccine, 29(16), (Apr. 5, 2011), 2968-77.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kopecky, S. A, et al., "Matrix protein and another viral component contribute to induction of apoptosis in cells infected with vesicular stomatitis virus", J Virol., 75(24), (Dec., 2001), Abstract Only.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.
Kovesdi, et al., "Adenoviral vectors for gene transfer", Current Opinion in Biotechnology, vol. 8, (1997), 583-589.
Kovesdi, I., et al., "Adenoviral Vectors for Gene Transfer", Current Opinion in Biotechnology, 8(5), (Oct. 1997), 583-589.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990), 9 pgs.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.
Kunik, Vered, et al., "Paratome: an online tool for systematic identification of antigen-binding regions in antibodies based on sequence or structure", Nucleic Acids Research, vol. 40, Issue W1, (2012), W521-W524.
Kunkel, T. A., "Rapid and Efficient Site-Specific Mutagenesis Without Phenotypic Selection", Proc. Natl. Acad. Sci. USA, 82, (1985), 488-492.
Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Lawson, N. D., "Recombinant Vesicular Stomatitis Viruses From DNA", Proc. Natl. Acad. Sci. USA, 92(10), (1995), 4477-4481.
Laxman, B., "Noninvasive Real-Time Imaging of Apoptosis", PNAS, 99(26), (2002), 16551-16555.
Lazarovits, Janette, et al., "Endocytosis of Chimeric Influenza Virus Hemagulutinin Proteins That Lack a Cytoplasmic Recognition Feature for Coated Pits", The Journal of Cell Biology, vol. 134, No. 2, (1996), 339-348.

(56) References Cited

OTHER PUBLICATIONS

Le, T., "CaSpeR5, a family of Drosophila transgenesis and shuttle vectors with improved multiple cloning sites", Biotechniques, 42(2), (Feb., 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.
Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.
Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.
Leal, et al., "New challenges in therapeutic vaccines against HIV infection", Expert Review of Vaccines, vol. 16, No. 6, (2017), 587-600.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, D.-H., et al., "H9N2 avian influenza virus-like particle vaccine provides protective immunity and a strategy for the differentiation of infected from vaccinated animals", Vaccine, vol. 29, (2011), 4003-4007.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.
Li, Junwei, et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza A Virus Transfectants with Chimeric Hemagglutinins Containing Epitopes from Different Subtypes", Journal of Virology, 66(1), (1992), 399-404.
Li, S., et al., "Recombinant Influenza A Virus Vaccines for the Pathogenic Human A/Hong Kong/97 (H5N1) Viruses", J Infect Dis., 179(5), (1999), 1132-1138.
Li, Shengqiang, et al., "Influenza A Virus Transfectants with Chimeric Hemagglutinins containing Epitopes from different subtypes", Journal of Virology 399-404, (1992), 6 pgs.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant of Influenza Virus and its Rescue by Cloned Neuraminidase Genes", Virology, 194(1), (1993), 403-407.
Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.
Liu, Z, et al., "Fine mapping of the antigen-antibody interaction of scFv215 A recombinant antibody inhibiting RNA polymerase II from Drosophila melanogaster", J. Mol. Recog. 12:103-111, (1999), 9 pgs.
Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.
Longnecker, R., et al., "WW- and SH3-domain interactions with Epstein-Barr virus LMP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.

(56) References Cited

OTHER PUBLICATIONS

Mansky, L. M, "Retrovirus mutation rates and their role in genetic variation", J Gen Virol., 79 (Pt 6), (Jun., 1998), 1337-45.

Manz, Benjamin, et al., "Disruption of the Viral Polymerase Complex Assembly as a Novel Approach to Attenuate Influenza A Virus", The Journal of Biological Chemistry, 286(10), (2011), 8414-8424.

Mark, A, et al., "Effect of Mutations and Deletions in a Bicistronic mRNA on the Synthesis of Influenza B Virus N

(56) References Cited

OTHER PUBLICATIONS polymerase gene rapidly loses temperature sensitivity following replication in hamsters", Vaccine, 15(12-13) 1372-8, (1997), 7 pgs.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Muyldermans, S, "Nanobodies: Natural single-domain antibodies", Ann. Rev. Biochem. 82, (2013), 1 pg.

Naim, H. Y., et al., "Basis for Selective Incorporation of Glycoproteins into the Influenza Virus Envelope", Journal of Virology, 67(8), (1993), 4831-4841.

Naito, S., et al., "Function and Structure of RNA Polymerase From Vesicular Stomatitis Virus", The Journal of Biological Chemistry, 251(14), (1976), 4307-4314.

Nara, et al., "How Can Vaccines Against Influenza and Other Viral Diseases Be Made More Effective?", PLoS Biology, 8 (12), (2010), e1000571.

Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.

Neirynck, S., "A universal influenza A vaccine based on the extracellular domain of the M2 protein", Nature Medicine, 5 (10), (Oct. 1999), pp. 1157-1163.

Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.

Neumann, G., et al., "A Decade After the Generation of a Negative-Sense RNA Virus From Cloned cDNA-What Have We Learned?", Journal of General Virology, 83(11), (Nov. 2002), 2635-2662.

Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.

Neumann, G., et al., "An improved reverse genetics system for influenza A virus generation and its implications for vaccine production", Proc. Natl. Acad. Sci. USA. 102(46), (2005), 16825-16829.

Neumann, G., et al., "Emergence and pandemic potential of swine-origin HIN1 influenza virus", Nature (London), 459(7249), (Jun. 2009), 931-939.

Neumann, G., et al., "Generation of influenza A virus from cloned cDNAs—historical perspective and outlook for the new millenium.", Rev Med Virol., 12(1), XP002314285, (Jan.-Feb. 2002), 13-30.

Neumann, G., et al., "Generation of influenza A viruses entirely from cloned cDNAs", Proc. Natl. Acad. Sci. USA., 96(16), (1999), 9345-9350.

Neumann, G., et al., "Genetic Engineering of Influenza and Other Negative-Strand RNA Viruses Containing Segmented Genomes", Advances in Virus Research, 53, (1999), 265-300.

Neumann, G., et al., "Influenza A virus NS2 protein mediates vRNP nuclear export through NES-independent interaction with hCRM1", The EMBO Journal, 19 (24), (2000), 6751-6758.

Neumann, G., et al., "Mutational analysis of influenza virus promoter elements in vivo", Journal of General Virology, 76 1709-1717, (1995), 9 pgs.

Neumann, G., et al., "Nuclear Import and Export of Influenza Virus Nucleoprotein", Journal of Virology, 71(12), (1997), 9690-9700.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan., 2000), 547-551.

Neumann, G., et al., "Reverse genetics of influenza virus.", Virology, 287(2), (Sep. 1, 2001), 243-50.

Neumann, G., et al., "Reverse Genetics of Influenza Viruses—Applications in Research and Vaccine Design", Monographs in Virology, 27, (2008), 118-133.

Neumann, G., et al., "RNA Polymerase I-Mediated Expression of Influenza Viral RNA Molecules", Virology, 202(1), (1994), 477-479.

Neumann, G., et al., "Synthesis of Influenza Virus: New impetus from an old enzyme, RNA polymerase 1", Virus Research 82(1-2), (Jan. 30, 2002), 153-158.

Neumann, Gabriele, "Minireview Reverse Genetics of Influenza Virus", Virology, vol. 287, (2001), 243-250.

Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.

Niwa, H., et al., "Efficient Selection for High-Expression Transfectants With a Novel Eukaryotic Factor", Gene, 108(2), (1991), 193-199.

Noda, Takeshi, et al., "Three-dimensional analysis of ribonucleoprotein complexes in influenza A virus", Nature Communications, 3, (2012), 1-6.

Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.

Odagiri, Takato, et al., "Segment-Specific Noncoding Sequences of the In?uenza Virus Genome RNA are Involved in the Speci?c Competition between Defective Interfering RNA and Its Progenitor RNA Segment at the Virion Assembly Step", Journal of Virology, 71(3), (1997), 2138-2145.

Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.

Onishi, M., et al., "Applications of retrovirus-mediated expression cloning", Experimental Hematology, 24(2), (1996), 324-329.

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Ozaki, "Generation of High-Yielding Influenza A Viruses in African Green Monkey Kidney (Vero) Cells by Reverse Genetics", J Virol 78(4), (2004), 1851-1857.

Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.

Ozawa, M., et al., "An adenovirus vector-mediated reverse genetics system for Influenza A virus generation", Journal of Virology, The American society for Microbiology, US vol. 81 (17), XP002471230, ISSN: 0022-538X, (Jun. 27, 2007), 9556-9559.

Ozawa, M., et al., "Replication-incompetent influenza A viruses that stably express a foreign gene", Journal of General Virology, 92(Part 12)., (2011), 2879-2888.

Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.

Palese, P., et al., "47. Orthomyxoviridae: The Viruses and Their Replication", In: Fields Virology (5th Edition), (2007), 90 pgs.

Palese, P., "Negative-Strand RNA Viruses: Genetic Engineering and Applications", Proc. Natl. Acad. Sci. USA, 93(21), (1996), 11354-11358.

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

(56) References Cited

OTHER PUBLICATIONS

Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363 617-619, (2004), 3 pgs.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes In the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>,(Sep. 2, 2015), 50 pgs.
Pinto, L. H., et al., "Influenza Virus M2 Protein Has Ion Channel Activity", Cell, 69, (May 1992), pp. 517-528.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", PLOS ONE, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicholson, K. G., et al., Editors, (Blackwell Scientific Publication), (1998), 3-18.
Preston, Andrew, "Choosing a Cloning Vector", Methods in Molecular Biology, vol. 235, E. coli Plasmid Vectors 19-27, Edited by: N. Casali and A. Preston, (2003), 9 pgs.

Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the Feb.-2001, Mar.-2003, and Apr.-2003 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "Minireview—Recovery of Negative-Strand RNA Viruses From Plasmid DNAs: A Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.

(56) References Cited

OTHER PUBLICATIONS

Satterlee, B., "Production of H5N1 avian influenza virus vaccine by plasmid-based reverse genetics technology", Basic Biotechnology eJournal, vol. 4, pp. 93-98, (2008), 93-98 Pgs.

Saunders, Kevin O., et al., "Neutralizing antibody vaccine for pandemic and pre-emergent coronaviruses", Nature, 594, (2021), 553-559 (27 pgs.).

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Schlesinger, S., "Rna Viruses as Vectors for the Expression of Heterologous Proteins", Molecular Biotechnology, 3(2), (1995), 155-165.

Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.

Schnell, M. J., "Infectious Rabies Viruses From Cloned cDNA", The EMBO Journal, 13(18), (1994), 4195-4203.

Schnell, Matthias J, et al., "Requirement for a non-specific glycoprotein cytoplasmic domain sequence to drive efficient budding of vesicular stomatitis virus", EMBO Journal, 17 (5), (1998), 1289-1296.

Schotsaert, M, et al., "Universal M2 ectodomain-based influenza A vaccines: preclinical and clinical developments", Expert Rev Vaccines. Apr. 2009;8(4):, 499-508.

Schultz-Cherry, S., et al., "Influenza Virus NS1 Protein Induces Apoptosis in Cultured Cells", Journal of Virology, 75(17), (2001), 7875-7881.

Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.

Sheridan, Cormac, et al., "Innovators target vaccines for variants and shortages in global South", Nature Biotechnology, 39(4), (Apr. 2021), 393-396.

Shi, Pei-Yong, "Infectious cDNA Clone of the Epidemic West Nile Virus from New York City", Journal of Virology 5847-5856, (Jun. 2002), 10 pgs.

Shimojima, M., et al., "Tyro3 family-mediated cell entry of Ebola and Marburg viruses", J Virol., 80(20), (Oct., 2006), 10109-16.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Shortridge, K. F., et al., "Characterization of Avian H5N1 Influenza Viruses From Poultry in Hong Kong", Virology, 252 331-342, (1998), 12 pgs.

Sidhu, M. S., et al., "Rescue of Synthetic Measles Virus Minireplicons: Measles Genomic Termini Direct Efficient Expression and Propagation of a Reporter Gene", Virology, 208, (1995), 800-807.

Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.

Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22) 11318-11330, (2008), 13 pgs.

Skehel, J. J., et al., "On the Mechanism of Inhibition of Influenza Virus Replication by Amantadine Hydrochloride", The Journal of General Virology, 38 (1), (1977), pp. 97-110.

Smatti, Maria K., et al., "Viral-Induced Enhanced Disease Illness", Front Microbiol, vol. 9: Article 2991, (Dec. 2018), 1-19.

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

Smura, T, "Surface glycoprotein [Severe acute respiratory syndrome coronavirus 2]", Gen Bank Accessions QH062107, (Feb. 11, 2020), 2 pgs.

Stray, S. J., et al., "Influenza virus infection of desialylated cells", Glycobiology, 10(7), (2000), 649-658.

Strobel, I., et al., "Efficient Expression of the Tumor-Associated Antigen MAGE-3 in Human Dendritic Cells, Using an Avian Influenza Virus Vector", Human Gene Therapy, 11(16), (2000), 2207-2218.

Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.

Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.

Subbarao, K., et al., "Characterization of an Avian Influenza A (H5N1) Virus Isolated From a Child With a Fatal Respiratory Illness", Science, 279, (1998), 393-396.

Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.

Sugawara, K., et al., "Development of Vero Cell-Derived Inactivated Japanese Encephalities Vaccine", Biologicals, 30 303-314, (2002), 12 pgs.

Sugrue, R. J., et al., "Specific structural alteration of the influenza haemagglutinin by amantadine", The EMBO Journal, 9 (11), (1990), pp. 3469-3476.

Sugrue, R. J., et al., "Structural Characteristics of the M2 Protein of Influenza A Viruses: Evidence That It Forms a Tetrameric Channel", Virology, 180, (1991), pp. 617-624.

Suguitan, A. L, et al., "Live, Attenuated Influenza A H5N1 Candidate Vaccines Provide Broad Cross-Protection in Mice and Ferrets", PLoS Med., 3(9), (2006), 1541-1555.

Sun, Weina, et al., "Development of Influenza B Universal Vaccine Candidates Usingthe "Mosaic" Hemagglutinin Approach", American Society for Microbiology, Journal of Virology, Vaccines and Antiviral Agents, vol. 93, Issue 12, (Jun. 2019), 17 pgs.

Sunstrom, N. A., et al., "Ion Channels formed by NB, an influenza B virus Protein", J. of Membrane Biology, vol. 150, XP002196654, (Dec. 1996), 127-132.

Sweet, T. M., et al., "Creation of amantadine resistant clones of influenza type A virus using a new transfection procedure.", J Virol Methods., 69(1-2), (Dec., 1997), 103-11.

Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.

Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.

Takada, A., et al., "Downregulation of beta1 integrins by Ebola virus glycoprotein: implication for virus entry", Virology, 278(1), (Dec., 2000), Abstract Only.

Takada, Ayato, et al., "A system for functional analysis of Ebola? virus?glycoprotein", Proc. Natl. Acad. Sci. USA, 94(26), (1997), 14764-14769.

Takada, Ayato, et al., "Antibody-dependent enhancement of viral infection: molecular mechanisms and in vivo implications", Rev Med Virol, 13(6), (2003), 387-398.

Takada, Ayato, et al., "Epitopes Required for Antibody-Dependent Enhancement of Ebola Virus Infection", J Infect Dis, 196 (Suppl 2), (2007), S347-S356.

Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.

Takada, Ayato, et al., "Infectivity-Enhancing Antibodies to Ebola Virus Glycoprotein", Journal of Virology, 75(5), (2001), 2324-2330.

Takada, Ayato, et al., "Protective efficacy of neutralizing antibodies against Ebola virus infection", Vaccine, 25(6), (2007), 993-999.

Takada, Ayato, et al., "The pathogenesis of Ebola hemorrhagic fever", Trends in Microbiology, 9(10), (2001), 506-511.

(56) References Cited

OTHER PUBLICATIONS

Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.

Takeda, M., et al., "Influenza a virus M2 ion channel activity is essential for efficient replication in tissue culture.", J Virol., 76(3), (Feb., 2002), 1391-9.

Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.

Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.

Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.

Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.

Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb., 1984), 457-62.

Taylor, J., et al., "Newcastle Disease Virus Fusion Protein Expressed in a Fowlpox Virus Recombinant Confers Protection in Chickens", Journal of Virology, 64(4), (1990), 1441-1450.

Terry, G., et al., "The Contruction of Defective Interfering Rubella Virus Particles", Archives of Virology, 145(3), (2000), 625-633.

Tetsutani, K., et al., "Adjuvants in Influenza Vaccines", Vaccine 2012, vol. 30, (2012), 4 pgs.

Thao, Tran Thi Nhu, et al., "Rapid reconstruction of SARS-CoV-2 using a synthetic genomics platform", Nature, vol. 582 561-565, (2020), 24 pgs.

Theriault, S., "The role of reverse genetics systems in determining filovirus pathogenicity", Archives of Virology, Supplementum. 157-177, (2005), 22 pgs.

Thompson, Christine M, et al., "Critical assessment of influenza VLP production in Sf9 and HEK293 expression systems", BMC Biotechnology, 15(1), (May 16, 2015), 12 pgs.

Thompson, W. W., et al., "Mortality Associated With Influenza and Respiratory Syncytial Virus in the United States", JAMA, 289(2) 179-186, (2003), 8 pgs.

Tobler, K, et al., "Effect of cytoplasmic tail truncations on the activity of the M(2) ion channel of influenza A virus", J Virol., 73(12), (Dec. 1999), 9695-9701.

Towner, J S, et al., "Generation of eGFP express ing recombinant Zaire ebolavirus for analysis of early pathogenesis events and high-throughput antiviral drug screening", Virology, Academic Press , Orlando, US , vol. 332, No. 1 20-27, XP004715289 ISSN: 0042-6822 the whole document, (Feb. 5, 2005), 8 pgs.

Treanor, J. J, et al., "The B allele of the NS gene of avian influenza viruses, but not the A allele, attenuates a human influenza a virus for squirrel monkeys", Virology, 171(1), (1989), 1-9.

Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.

Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.

Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.

Varner, Chad, "Developing Synthetic Multivalent Cellular Effectors", Thesis, School of Chemical and Biomolecular Engineering, Georgia Institute of Technology, (Aug. 2017), 88 pgs.

Verma, I. M, et al., "Gene Therapy—Promises, Problems and Prospects", Nature, 389, (1997), 239-242.

Via, L. E, et al., "Isolation of restriction fragments from large plasmids recovered from bacteria with multiple plasmids", Biotechniques, 11(4), (Oct., 1991), Abstract Only.

Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.

Victor, Sylvia, et al., "A Replication-Incompetent PB2-Knockout Influenza A Virus Vaccine Vector", Journal of Virology, vol. 86, No. 8, (Apr. 2012), 4123-4128.

Vincke, C, et al., "Introduction to heavy chain antibodies and derived nanobodies", Meth. Mol. Biol. 911, (2012), 13 pgs.

Voeten, J. T, et al., "Characterization of high-growth reassortant influenza A viruses generated in MDCK cells cultured in serum-free medium", Vaccine, vol. 17, (1999), 1942-1950.

Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.

Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.

Wagner, R., et al., "Interdependence of hemagglutinin glycosylation and neuraminidase as regulators of influenza virus growth: a study by reverse genetics", Journal of Virology, 74 (14), (Jul. 2000), 6316-6323.

Walker, W. S, et al., "HEL-Flu: an influenza virus containing the hen egg lysozyme epitope recognized by CD4+ T cells from mice transgenic for an alphabeta TCR", J. Immunol., 159(6), (Sep., 1997), 2563-2566.

Wan, Yushun, et al., "Molecular mechanism for Antibody-Dependent Enhancement of Coronavirus EntrM", Journal of Virology, 94(5): e02015-19, (2019), 1-15.

Wang, et al., "Glycoengineering of CHO Cells to Improve Product Quality", Methods in Molecular Biology book series (MIMB, vol. 1603) 25-44, (May 11, 2017), 256 pgs.

Wang, B., et al., "Construction of Non-infectious SARS-CoV-2 Replicons and Their Application in Drug Evaluation", Virologica Sinica, 36, (2021), 890-900.

Wang, C., et al., "Ion Channel Activity of Influenza A Virus M2 Protein: Characterization of the Amantadine Block", Journal of Virology, 67 (9), (Sep. 1993), pp. 5585-5594.

Wang, Sheng-Fan, et al., "Antibody-dependent SARS coronavirus infection is mediated by antibodies against spike proteins", Biochem Biophys Res Commun, 451 208-214, (2014), 8 pgs.

Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.

Wang, Wenlig, et al., "Robust Immunity and Heterologous Protection against Influenza in Mice Elicited by a Novel Recombinant NP-M2e Fusion Protein Expressed in *E. coli*", PLoS ONE 7(12): e52488, (Dec. 2012), 1-13.

Wanitchang, Asawin, et al., "Characterization of influenza A virus pseudotyped with the spike protein of porcine epidemic diarrhea virus", Archives of Virology, 163(12), (2018), 3255-3264.

Ward, C. D., et al., "Direct Measurement of the Poliovirus RNA Polymerase Error Frequency in Vitro", Journal of Virology, 62(2), (1988), 558-562.

Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.

Warfield, et al., "", PNAS, vol. 100(26), (2003), pp. 5889-15894.

(56) References Cited

OTHER PUBLICATIONS

Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza A Virus Lacking M2 Protein as a Live Attenuated Vaccine", Journal of Virology, 83(11), (2009), 5947-5950.
Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals to Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Weber, F., et al., "Conserved vRNA end sequences of Thogotoorthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Webster, R G, et al., "Evolution and molecular epidemiology of H9N2 influenza A viruses from quail in southern China", XP002744257, retrieved from EBI accession No. UNIPROT:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, De, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal of Virology, 68(10), (1994), 6605-6618.
Wilson, et al., "Vaccine Potential of Ebola Virus VP24, VP30, VP35 and VP40 Proteins", Virology 286, (2001), 384-90.
Wilson, Julie A, et al., "Epitopes Involved in Antibody-Mediated Protection from Ebola Virus", Science, 287(5458), (Mar. 2000), 1664-1666.

Winkler, K., et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wolff, et al., "Downstream porcessing of cell culture-derived virus particles", Expert Rev. Vaccines 10(10) 1451-1475, (2011), 25 pgs.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23 pgs.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, P., et al., "Hemagglutinin Specificity and Neuraminidase Coding Capacity of Meuraminidase-Deficient Influenza Viruses", Virology, 229(1), (1997), 155-165.
Yang, Z. Y., et al., "Identification of the Ebola virus glycoprotein as the main viral determinant of vascular cell cytotoxicity and injury", Nat Med., 6(8), (Aug., 2000), Abstract Only.
Yannarell, Dean A., et al., "Factors affecting the yield of cold-adapted influenza virus vaccine", Journal of Virological Methods, vol. 64, 161-169, (1997), 1 pg.
Yasuda, J., "Growth Control of Influenza A Virus by M1 Protein: Analysis of Transfectant Viruses Carrying the Chimeric M Gene", Journal of Virology, 68(12), (1994), 8141-8146.
Yen, H L, et al., "Neuraminidase Inhibitor-Resistant Recombinant A/Vietnam/1203/04 (K5N1) Influenza Viruses Retain Their Replication Efficiency and Pathogenicity in Vitro and in Vivo", Journal of Virology., vol. 81, No. 22, (Nov. 15, 2007), 12418-12426.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yip, Ming S., et al., "Antibody-dependent infection of human macrophages by severe acute respiratory syndrome coronavirus", Virology Journal, 11: 82, (2014), 11 pgs.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

(56) References Cited

OTHER PUBLICATIONS

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain Ig Gene Carrying a Viral T Cell Epitope are Lysed by Specific Cytolytic T Cells", The Journal of Immunology, 148(11), (1992), 3604-3609.

Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zeitlin, L., et al., "Antibody Therapeutics for Ebola Virus Disease", Curr. Opin. Viral. 17:, (2016), 11 pgs.

Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zhang, Q.-Y., et al., "SARS-CoV-2 replicon for high-throughput antiviral screening", J Gen Virol,, 102(5), (2021), 1-4.

Zhang, V. Q, et al., "Easy two-step method for randomizing and cloning gene fragments", Methods Mol Biol., 634, (2010), Abstract Only.

Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.

Zhang, Y., et al., "A bacterial artificial chromosome (BAC)-vectored noninfectious replicon of SARS-CoV-2", Antiviral Research, vol. 185, 104974, (Jan. 2021), 1-9.

Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.

Zhou, Yan, "Membrane-Anchored Incorporation of a Foreign Protein in Recombinant Influenza Virions", Virology 246(1), (1998), 83-94.

Zobel, A., et al., "RNA Polymerase I Catalysed Transcription of Insert Viral cDNA", Nucleic Acids Research, 21(16), (1993), 3607-3614.

U.S. Appl. No. 09/834,095 U.S. Pat. No. 6,872,395, filed Apr. 12, 2001, Viruses Comprising Mutant Ion Channel Protein.
U.S. Appl. No. 11/043,768 U.S. Pat. No. 8,057,806, filed Jan. 26, 2005, Viruses Comprising Mutant Ion Channel Protein.
U.S. Appl. No. 10/081,170 U.S. Pat. No. 7,176,021, filed Feb. 22, 2002, Methods to Identify Mutant Cells With Altered Sialic Acid.
U.S. Appl. No. 11/644,179 U.S. Pat. No. 8,679,819, filed Dec. 22, 2006, Mutant Cells With Altered Sialic Acid.
U.S. Appl. No. 10/353,856 U.S. Pat. No. 7,211,378, filed Jan. 29, 2003, Filovirus Vectors and Noninfectious Filovirus-Based Particles.
U.S. Appl. No. 11/654,863, filed Jan. 18, 2007, Filovirus Vectors and Particles Produced Therefrom.
U.S. Appl. No. 12/245,296 U.S. Pat. No. 8,900,595, filed Oct. 3, 2008, Filovirus Vectors and Noninfectious Filovirus-Based Particles.
U.S. Appl. No. 60/438,679, filed Jan. 7, 2003, Signal for Packaging of Influenza Virus Vectors.
U.S. Appl. No. 15/915,486, filed Mar. 8, 2018, Filovirus Vectors and Particles Produced Therefrom.
U.S. Appl. No. 10/366,630 U.S. Pat. No. 7,226,774, filed Feb. 12, 2003, Signal for Packaging of Influenza Virus Vectors.
U.S. Appl. No. 11/509,249 U.S. Pat. No. 7,585,657, filed Aug. 24, 2006, Signal for Packaging of Influenza Virus Vectors.
U.S. Appl. No. 12/470,287 U.S. Pat. No. 8,298,805, filed May 21, 2009, Signal for Packaging of Influenza Virus Vectors.
U.S. Appl. No. 10/827,995 U.S. Pat. No. 7,588,769, filed Apr. 20, 2004, Viruses Encoding Mutant Membrane Protein.
U.S. Appl. No. 12/467,492, filed May 18, 2009, Viruses Encoding Mutant Membrane Protein.
U.S. Appl. No. 10/855,975 U.S. Pat. No. 7,723,094, filed May 27, 2004, Recombinant Influenza Vectors With a Pollii Promoter and Ribozymes for Vaccines and Gene Therapy.
U.S. Appl. No. 10/855,875 U.S. Pat. No. 8,475,806, filed May 27, 2004, High Titer Recombinant Influenza Viruses for Vaccines and Gene Therapy.
U.S. Appl. No. 11/283,498 U.S. Pat. No. 7,968,101, filed Nov. 18, 2005, Recombinant Influenza Vectors With Tandem Transcription Units.
U.S. Appl. No. 13/113,244 U.S. Pat. No. 8,877,209, filed May 23, 2011, Recombinant Influenza Vectors With Tandem Transcription Units.
U.S. Appl. No. 14/528,997 U.S. Pat. No. 10,358,630, filed Oct. 30, 2014, Recombinant Influenza Vectors With Tandem Transcription Units.
U.S. Appl. No. 11/729,557 U.S. Pat. No. 9,254,318, filed Mar. 29, 2007, High Titer Recombinant Influenza Viruses for Vaccines.
U.S. Appl. No. 15/000,851 U.S. Pat. No. 9,926,535, filed Jan. 19, 2016, High Titer Recombinant Influenza Viruses for Vaccines.
U.S. Appl. No. 15/905,454, filed Feb. 26, 2018, High Titer Recombinant Influenza Viruses for Vaccines.
U.S. Appl. No. 11/810,956, filed Jun. 7, 2007, Screening Method for Modulators of Viral Transcription or Replication.
U.S. Appl. No. 12/139,183 U.S. Pat. No. 8,043,856, filed Jun. 13, 2008, Adenoviral Vectors for Influenza Virus Production.
U.S. Appl. No. 12/113,690 U.S. Pat. No. 8,597,661, filed May 1, 2008, Neuraminidase-Deficient Live Influenza Vaccines.
U.S. Appl. No. 12/058,389 U.S. Pat. No. 8,465,960, filed Mar. 28, 2008, Influenza B Viruses With Reduced Sensitivity to Neuraminidase Inhibitors.
U.S. Appl. No. 12/214,414 U.S. Pat. No. 9,474,798, filed Jun. 18, 2008, Influenza M2 Protein Mutant Viruses as Live Influenza Attenuated Vaccines.
U.S. Appl. No. 15/292,595 U.S. Pat. No. 10,119,124, filed Oct. 13, 2016, Influenza M2 Protein Mutant Viruses as Live Influenza Attenuated Vaccines.
U.S. Appl. No. 16/144,441, filed Sep. 27, 2018, Influenza M2 Protein Mutant Viruses as Live Influenza Attenuated Vaccines.
U.S. Appl. No. 12/854,578 U.S. Pat. No. 8,507,247, filed Aug. 11, 2010, Influenza A Virus With Attenuating Mutations In NS2 Protein.
U.S. Appl. No. 13/127,951 U.S. Pat. No. 9,222,118, filed Jul. 15, 2011, Scren for Inhibitors of Filovirus and Uses Therefor.
U.S. Appl. No. 14/919,431, filed Oct. 21, 2015, Screen for Inhibitors of Filovirus and Uses Therefor.
U.S. Appl. No. 15/227,147, filed Aug. 3, 2016, Screen for Inhibitors of Filovirus and Uses Therefor.
U.S. Appl. No. 15/654,431, filed Jul. 19, 2017, Screen for Inhibitors of Filovirus and Uses Therefor.
U.S. Appl. No. 12/912,411 U.S. Pat. No. 9,109,013, filed Oct. 26, 2010, High Titer Recombinant Influenza Viruses With Enhanced Replication in Vero Cells.
U.S. Appl. No. 14/816,807 U.S. Pat. No. 10,059,925, filed Aug. 3, 2015, High Titer Recombinant Influenza Viruses With Enhanced Replication in Vero Cells.
U.S. Appl. No. 16/046,250 U.S. Pat. No. 10,808,229, filed Jul. 26, 2018, High Titer Recombinant Influenza Viruses With Enhanced Replication in Vero Cells.
U.S. Appl. No. 13/070,110 U.S. Pat. No. 10,130,697, filed Mar. 23, 2011, Vaccines Comprising Mutant Attenuated Influenza Viruses.
U.S. Appl. No. 16/173,605 U.S. Pat. No. 11,007,262, filed Oct. 29, 2018, Vaccines Comprising Mutant Attenuated Influenza Viruses.

(56) References Cited

OTHER PUBLICATIONS

U.S. Appl. No. 17/229,001, filed Apr. 13, 2021, Vaccines Comprising Mutant Attenuated Influenza Viruses.
U.S. Appl. No. 13/594,611 U.S. Pat. No. 9,101,653, filed Aug. 24, 2012, Influenza Viruses With Mutant PB2 Gene Segment as Live Attenuated Vaccines.
U.S. Appl. No. 14/699,213 U.S. Pat. No. 10,513,692, filed Apr. 29, 2015, Influenza Viruses With Mutant PB2 Segment as Live Attenuated Vaccines.
U.S. Appl. No. 16/694,748 U.S. Pat. No. 11,348,339, filed Nov. 25, 2019, Influenza Viruses With Mutant PB2 Gene Segment as Live Attenuated Vaccines.
U.S. Appl. No. 17/835,830, filed Jun. 8, 2022, Influenza Viruses With Mutant PB2 Gene Segment as Live Attenuated Vaccines.
U.S. Appl. No. 14/332,121 U.S. Pat. No. 9,950,057, filed Jul. 15, 2014, High Titer Recombinant Influenza Viruses With Enhanced Replication in MDCK or Vero Cells or Eggs.
U.S. Appl. No. 15/593,039 U.S. Pat. No. 10,172,934, filed May 11, 2017, High Titer Recombinant Influenza Viruses With Enhanced Replication in MDCK or Vero Cells or Eggs.
U.S. Appl. No. 16/178,323, filed Nov. 1, 2018, High Titer Recombinant Influenza Viruses With Enhanced Replication in MDCK or Vero Cells or Eggs.
U.S. Appl. No. 14/745,236 U.S. Pat. No. 10,053,671, filed Jun. 19, 2015, Mutations That Confer Genetic Stability to Additional Genes in Influenza Viruses.
U.S. Appl. No. 15/966,092 U.S. Pat. No. 11,046,934, filed Apr. 30, 2018, Mutations That Confer Genetic Stability to Additional Genes in Influenza Viruses.
U.S. Appl. No. 17/352,845, filed Jun. 21, 2021, Mutations That Confer Genetic Stability to Additional Genes in Influenza Viruses.
U.S. Appl. No. 15/204,381, filed Jul. 7, 2016, Potent Glycoprotein Antibody as a Therapeutic Against Ebola Virus.
U.S. Appl. No. 15/170,556 U.S. Pat. No. 10,633,422, filed Jun. 1, 2016, Influenza Virus Replication By Inhibiting Microrna LEC7C Binding to Influenza Viral CRNA and MRNA.
U.S. Appl. No. 15/203,581 U.S. Pat. No. 9,890,363, filed Jul. 6, 2016, Influenza Virus Replication for Vaccine Development.
U.S. Appl. No. 15/865,364 U.S. Pat. No. 10,246,686, filed Jan. 9, 2018, Influenza Virus Replication for Vaccine Development.
U.S. Appl. No. 16/284,020, filed Feb. 25, 2019, Influenza Virus Replication for Vaccine Development.
U.S. Appl. No. 15/247,006 U.S. Pat. No. 10,494,613, filed Aug. 25, 2016, Generation of Infectious Influenza Viruses From Viruses-Like Particles.
U.S. Appl. No. 16/547,262 U.S. Pat. No. 11,180,737, filed Aug. 21, 2019, Generation of Infectious Influenza Viruses From Viruses-Like Particles.
U.S. Appl. No. 15/436,245 U.S. Pat. No. 11,197,925, filed Feb. 17, 2017, Influenza B Virus Replication for Vaccine Development.
U.S. Appl. No. 17/546,835, filed Dec. 9, 2021, Influenza B Virus Replication for Vaccine Development.
U.S. Appl. No. 16/170,321 U.S. Pat. No. 11,197,926, filed Oct. 25, 2018, Recombinant Influenza Viruses With Stabilized HA for Replication in Eggs.
U.S. Appl. No. 17/546,967, filed Dec. 9, 2021, Recombinant Influenza Viruses With Stabilized HA for Replication in Eggs.
U.S. Appl. No. 17/266,049, filed Feb. 4, 2021, Recombinant Biologically Contatined Filovirus Vaccine.
U.S. Appl. No. 16/545,761 U.S. Pat. No. 11,389,523, filed Aug. 20, 2019, Vectors for Eliciting Immune Responses to Non-Dominant Epitopes in the Hemagglutinin (HA) Protein.
U.S. Appl. No. 17/813,178, filed Jul. 18, 2022, Vectors for Eliciting Immune Responses to Non-Dominant Epitopes in the Hemagglutinin (HA) Protein.
U.S. Appl. No. 16/785,449, filed Feb. 7, 2020, Humanized Cell Line.
U.S. Appl. No. 16/865,194 U.S. Pat. No. 11,390,649, filed May 1, 2020, Influenza Virus Replication for Vaccine Development.
U.S. Appl. No. 17/813,200, filed Jul. 18, 2022, Influenza Virus Replication for Vaccine Development.
U.S. Appl. No. 16/749,910 U.S. Pat. No. 11,241,492, filed Jan. 22, 2020, Mutations that Confer Genetic Stability to Genes in Influenza Viruses.
U.S. Appl. No. 17/578,939, filed Jan. 19, 2022, Mutations that Confer Genetic Stability to Genes in Influenza Viruses.
U.S. Appl. No. 17/004,583, filed Aug. 27, 2020, Recombinant Influenza Viruses With Stabilized HA for Replication in Eggs.
U.S. Appl. No. 17/155,625, filed Jan. 22, 2021, Recombinant Influenza Viruses With Stabilized NA.
U.S. Appl. No. 17/212,836, filed Mar. 25, 2021, Recombinant Multivalent Influenza Viruses.
U.S. Appl. No. 17/936,194, filed Sep. 28, 2022, Compositions Comprising Complexes Displaying Antigens and Methods of Using the Compositions.
U.S. Appl. No. 18/173,535, filed Feb. 23, 2023, Broadly Protective Influenza B Virus Vaccines.
"U.S. Appl. No. 17/212,836, Notice of Allowability mailed Feb. 7, 2025", 5 pgs.
"U.S. Appl. No. 17/212,836, Notice of Allowance mailed Jan. 2, 2025", 8 pgs.
"U.S. Appl. No. 17/212,836, Response filed Nov. 26, 2024 to Non Final Office Action mailed Jun. 13, 2024", 9 pgs.
"U.S. Appl. No. 17/266,049 Corrected Notice of Allowability mailed Jan. 31, 2025", 3 pgs.
"U.S. Appl. No. 17/266,049, Examiner Interview Summary mailed Oct. 16, 2024", 2 pgs.
"U.S. Appl. No. 17/266,049, Final Office Action mailed Oct. 31, 2024", 14 pgs.
"U.S. Appl. No. 17/266,049, Notice of Allowance mailed Jan. 23, 2025", 11 pgs.
"U.S. Appl. No. 17/266,049, Response filed Oct. 14, 2024 to Non Final Office Action mailed Apr. 12, 2024", 12 pgs.
"U.S. Appl. No. 17/266,049, Response filed Dec. 4, 2024 to Final Office Action mailed Oct. 31, 2024", 12 pgs.
"U.S. Appl. No. 17/546,835, Non Final Office Action mailed Sep. 27, 2024", 9 pgs.
"U.S. Appl. No. 17/546,835, Response filed Jan. 22, 2025 to Non Final Office Action mailed Sep. 2027, 24", 9 pgs.
"U.S. Appl. No. 17/546,967, Corrected Notice of Allowability mailed Jan. 29, 2025", 2 pgs.
"U.S. Appl. No. 17/546,967, Notice of Allowance mailed Oct. 15, 2024", 8 pgs.
"U.S. Appl. No. 17/813,200, Corrected Notice of Allowability mailed Sep. 17, 2024", 2 pgs.
"U.S. Appl. No. 17/835,830, Non Final Office Action mailed Dec. 4, 2024", 7 pgs.
"U.S. Appl. No. 18/461,321, Non Final Office Action mailed Nov. 14, 2024", 6 pgs.
"U.S. Appl. No. 18/461,321, Response filed Jan. 7, 2025 to Non Final Office Action mailed Nov. 14, 2024", 6 pgs.
"U.S. Appl. No. 18/525,460, Notice of Allowance mailed Oct. 23, 2024", 11 pgs.
"Chinese Application Serial No. 202080025289.6, Decision of Rejection mailed Jan. 14, 2025", W/English Translation, 15 pgs.
"Chinese Application Serial No. 202080025289.6, Office Action mailed Oct. 9, 2024", W/English Translation, 14 pgs.
"Chinese Application Serial No. 202080025289.6, Response filed Sep. 14, 2024 to Office Action mailed May 15, 2024", w/ current English claims, 16 pgs.
"Chinese Application Serial No. 202080025289.6, Response filed Dec. 9, 2024 to Office Action mailed Oct. 9, 2024", w/ English claims, 13 pgs.
"Chinese Application Serial No. 202080048487.4, Office Action mailed Dec. 30, 2024", w/ English translation, 18 pgs.
"European Application Serial No. 17709236.8, Response filed Sep. 16, 2024 to Communication Pursuant to Article 94(3) EPC mailed Mar. 14, 2024", 16 pgs.
"European Application Serial No. 17709236.8, Supplementary Response filed Jan. 7, 2025 to Communication Pursuant to Article 94(3) EPC mailed Mar. 14, 2024", 8 pgs.

(56) References Cited

OTHER PUBLICATIONS

"European Application Serial No. 19778696.5, Response filed Dec. 3, 2024 to Communication Pursuant to Article 94(3) EPC mailed Jun. 3, 2024", 26 pgs.
"European Application Serial No. 20714015.3, Response filed Nov. 25, 2024 to Communication Pursuant to Article 94(3) EPC mailed Aug. 5, 2024", 9 pgs.
"International Application Serial No. PCT/US2023/027622, International Preliminary Report on Patentability mailed Jan. 23, 2025", 8 pgs.
"Japanese Application Serial No. 2019-171818, Response filed Nov. 14, 2024 to Notification of Reasons for Rejection mailed May 14, 2024", w/ English claims, 12 pgs.
"Japanese Application Serial No. 2020-182549, Notification of Reasons for Refusal mailed Oct. 15, 2024", w/ English translation, 6 pgs.
"Japanese Application Serial No. 2020-182549, Response filed Aug. 20, 2024 to Notification of Reasons for Refusal mailed Feb. 20, 2024", w/ English claims, 12 pgs.
"Japanese Application Serial No. 2020-182549, Response filed Dec. 4, 2024 to Notification of Reasons for Refusal mailed Oct. 15, 2024", w/ English claims, 10 pgs.
"Japanese Application Serial No. 2021-509824, Response filed Nov. 29, 2024 to Notification of Reasons for Rejection mailed Jun. 4, 2024", w/ English claims, 41 pgs.
"Japanese Application Serial No. 2021-546853, Response filed Sep. 6, 2024 to Examiners Decision of Final Refusal mailed May 7, 2024", w/ English claims, 12 pgs.
"Japanese Application Serial No. 2022-016436, Appeal filed Dec. 13, 2024 to Examiners Decision of Final Refusal mailed Aug. 13, 2024", w/ English claims, 15 pgs.
"Japanese Application Serial No. 2022-016436, Examiners Decision of Final Refusal mailed Aug. 13, 2024", w/ English translation, 7 pgs.
"Japanese Application Serial No. 2022-161803, Response filed Dec. 4, 2024 to Notification of Reasons for Refusal mailed Jun. 4, 2024", w/ English claims, 13 pgs.
"Japanese Application Serial No. 2022-513269, Response filed Aug. 19, 2024 to Notification of Reasons for Refusal mailed Feb. 20, 2024", w/ English claims, 23 pgs.
"Japanese Application Serial No. 2023-204069, Notification of Reasons for Rejection mailed Jan. 14, 2025", W/English Translation, 5 pgs.
"Japanese Application Serial No. 2024-176620, Voluntary Amendment filed Dec. 11, 2024", w/ English claims, 13 pgs.
Chang, Chi-Chieh, et al., "Subunit vaccines with a saponin-based adjuvant boost humoral and cellular immunity to MERS coronavirus", Vaccine 41 (2023) 3337-3346, journal homepage: www.elsevier.com/locate/vaccine, (2023), 11.
Chen, Xiaorui, et al., "Comparison of four adjuvants revealed the strongest protection against lethal pneumococcal challenge following immunization with PsaA-PspA fusion protein and AS02 as adjuvant", https://pubmed.ncbi.nlm.nih.gov/30707297/ (abstract), (2019), 1 pg.
Ho, Nataschja I, et al., "Saponin-based adjuvants enhance antigen cross-presentation in human CD11c+ CD1c+ CD5- CD163+ conventional type 2 dendritic cells", J Immunother Cancer 2023, (2023), 17.
Ping, J., et al., "Development of high-yield influenza A virus vaccine viruses", Nature CommunicaTions, vol. 6, (Dec. 31, 2015), 1-15.
Zhao, Tingmei, et al., "Vaccine adjuvants: mechanisms and platforms", Signal Transduction and Targeted Therapy, www.nature.com/sigtrans, (Jul. 19, 2023), 24.
Zhu, Guangrui, et al., "Progress on Pathogenic Mechanism of Influenza A (H1N1) Virus", Progress in Veterinary Medicine, 08 w/English Abstract pp. 70-74, (Aug. 20, 2011), 5 pgs.
"U.S. Appl. No. 17/546,967, Corrected Notice of Allowability mailed Feb. 13, 2025", 2 pgs.
"European Application Serial No. 16778485.9, Communication Pursuant to Article 94(3) EPC mailed Feb. 11, 2025", 4 pgs.
"Japanese Application Serial No. 2020-182549, Office Action mailed Jan. 28, 2025", w/o English Translation, 2 pgs.
"U.S. Appl. No. 18/461,321, Advisory Action mailed Mar. 27, 2025", 2 pgs.
"U.S. Appl. No. 17/835,830, Response filed Apr. 3, 2025 to Non Final Office Action mailed Dec. 4, 2024", 6 pgs.
"U.S. Appl. No. 17/546,835, Corrected Notice of Allowability mailed Apr. 8, 2025", 2 pgs.
"Japanese Application Serial No. 2024-141090, Response filed Mar. 14, 2025 to Notification of Reasons for Refusal mailed Mar. 10, 2025", w English Claims, 41 pgs.
"Chinese Application Serial No. 202080025289.6, Request for Reexamination filed Apr. 11, 2025", W English Claims, 8 pgs.
"U.S. Appl. No. 17/835,830, Notice of Allowance mailed May 7, 2025", 7 pgs.
"Chinese Application Serial No. 202080048487.4, Response filed Apr. 29, 2025 to Office Action mailed Dec. 30, 2024", W English Claims, 70 pgs.
"Japanese Application Serial No. 2022-161803, Final Notification of Reasons for Rejection mailed Mar. 4, 2025", W English Translation, 6 pgs.

Figure 2

SEQ ID NO:1

MNPNQKIITIGSVSLTISTICFFMQIAILITTVTLHFKQYEFNSPPNN
QVMLCEPTIIERNITEIVYLTNTTIEKEICPKLAEYRNWSKPQCNIT
GFAPFSKDNSIRLSAGGDIWVTREPYVSCDPDKCYQFALGQGTTL
NNVHSNDIVHDRTPYRTLLMNELGVPFHLGTKQVCIAWSSSSCHD
GKAWLHVCVTGDDENATASFIYNGRLADSIVSWSKKILRTQESEC
VCINGTCTVVMTDGSASGKADTKILFIEEGKIVHTSTLSGSAQHVE
ECSCYPRYPGVRCVCRDNWKGSNRPIVDINIKDYSIVSSYVCSGLV
GDTPRKNDSSSSSHCLDPNNEEGGHGVKGWAFDDGNDVWMGRT
ISEKLRSGYETFKVIEGWSNPNSKLQINRQVIVDRGNRSGYSGIFSV
EGKSCINRCFYVELIRGRKQETEVLWTSNSIVVFCGTSGTYGTGSW
PDGADINLMPI

A/Yokohama/2017/03

Figure 3

MNPNQKIITIGSVSLTISTICFFMQIAILITTVTLHFKQYEFNSPPNNQVMLCEPTIIERNVTEIVYLTNTTIEKEI
CPKPAEYRNWSKPQCGITGFAPFSKDNSIRLSAGGDIWVTREPYVSCDPDKCYQFALGQGTTLNNVHSNNTVRDRTP
YRTLLMNELGVPFHLGTKQVCIAWSSSSCHDGKAWLHVCITGDDKNATASFIYNGRLVDSVVSWSKDILRTQESECV
CINGTCTVVMTDGSASGKADTKILFIEEGKIVHTSKLSGSAQHVEECSCYPRYPGVRCVCRDNWKGSNRPIVDINIK
DHSIVSSYVCSGLVGDTPRKNDSSSSHCLDPNNEEGGHGVKGWAFDDGNDVWMGRTINETSRLGYETFKVVEGWSN
PKSKLQINRQVIVDRGDRSGYSGIFSVEGKSCINRCFYVELIRGRKEETEVLWTSNSIVVFCGTSGTYGTGSWPDGA
DLNLMPI  (SEQ ID NO:2)

Figure 4

Y2017M3L4-NA(32A, 147N, 329D, 347Q, del46-50aa)
(SEQ ID NO:3)

```
MNPNQKIITIGSVSLTISTICFFMQIAILITA

Figure 5

N3 (Accession No. AAO62039.1)

```
  1 mnpnqkiiti gvvnttlsti alligvgnli fntvihekig dhqtvihptt ttpaipnesd
 61 tiitynntvi nnittiitea erlfkpplpl cpfrqffpfh kdnairlgen kdvivtrepy
121 vscdndncws falaqgallq tkhsngtikd rtpyrsliqf pigtapvlqn ykeiciawss
181 sscfdgkewm hvcmtgndnd asaqiiyagr mtdsikswkr dilrtqesec qcidgtcvva
241 vtdgpaansa dhrvywireg rivkyenvpk tkiqhleecs cyvdidvyci crdnwkgsnr
301 pwmrinneti letgyvcskf hsdtprpadp stvscdspsn vnggpgvkgf qfkvgndvwl
361 grtmstsgrs gfeiikvaeg winspnhaks vtqtlvsnnd wsgysgsfiv ktkacfqpcf
421 yvelirgrpn knddvswtsn sivtfcgldn epgsgnwpdg snigfmpk (SEQ ID NO:4)
```

N4 (Accession No. AAO62043.1)

```
  1 mnpnqkiiti gsvsiiltti gllqitslc siwfshynqv tqtheqpcsn nttyynetf
 61 vnvtnvqnny ttviepsapd vvhysagrdl cpirgwapls kdngirigsr qevfvirepf
121 iscsiseert ffltqgalln dkhsngtvkd rspfrtlmsc piqvapspsn srfesvawsa
181 tacsdgpgwi tlqitgpdat avavikyngi itdtlkswkg nimrtqesec vcqdefcytl
241 itdgpsdaqa fykilkirkg kivsmkdvda tgfhfeecsc ypsqtdiecv crdnwrgsnr
301 pwirfnsdld yqigyvcsgi fgdnprpvdg tgscnspvnn gkqrygvkgf sfrygdgvwi
361 grtkslesrs gfemvwdang wvstdkdsng vqdiidndnw sgysgsfsir qettgrnctv
421 pcfwvemirg qpkektiwts gssiafcgvn sdttgwswpd gallpfdidk (SEQ ID NO:5)
```

N6 (Accession No. AAO62070.1)

```
  1 mnpnqkiici satgmtlsvv slligianlg iniglhykmg dtpdvnipnm netnstttii
 61 nnhtqnnftn itniivnkne egtflnltkp lccevnswhil skdnairige dahilvtrep
121 ylscdpqgcr mfalsqqttl rgrhangtih drspfralis wemgqapspy nvrvecigws
181 stschdgisr msicmsqann nasavvwygg rpvteipswa gnilrtqese cvchkgicpv
241 vmtdgpannr aatkiiyfke gkiqkieela gntqhieecs cygavgvikc icrdnwkgan
301 rpvitidpem mthtskylcs kiltdtsrpn dptngncdap itggspdpgv kqfafldren
361 swlqrtiskd srsgyemlkv pnaetdtqsg pishqvivnn qnwsgysgaf idywankecf
421 npcfyvelir grpkessvlw tsnsivalcg skerlgswsw hdgaeiiyfk (SEQ ID NO:6)
```

N7 (Accession No. AIK26357.1)

```
  1 mnpnqklfal sqvaialsil nlligisnvg invslhlkgs sdqdknwtct svtqnntttli
 61 entyvnnttv idketgtakp nylmlnkslc kvegwvvvak dnairfgese qiivtrepyv
121 scdplgckmy alhqgttirn khsngtihdr tafrglistp lqsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn
```

Figure 5 cont.

```
421 pcfyvelirg rpeeakyvgw tsnslialcg spisvgsgsf pdgaqiqyfs (SEQ ID NO:7)
```

N8 (Accession No. AIK26315.1)

```
  1 mnpnqkiitv gsvslglvvl nillhivsit vtvlvlpgng nnknenstvi reynetvrie
 61 kvtqwhntnv ieyiekpesg hfmnnteaic dakqfapfsk dngirigsrg hvfvirepfv
121 scsptecrtf fltqgsllnd khsngtvkdr spyrtlmsve igqspnvyqa rfeavawsat
181 achdgkkwmt igvtqpdaka vavvhyggip tdvinswaqd ilrtqessct ciqgecywvm
241 tdqpanrqaq yrafkakqgk ivgqteisfn gshieecscy pnegkvecvc rdnwtgtnrp
301 vlvispdlsy ragylcaglp sdtprgedsq ftgsctspvg nqgygvkqfg frqgndvwmg
361 rtisrtsrsg feilkvrngw vqnskeqikr qvvvdnlkws gysgsftlpv eltkrnclvp
421 cfwvemirgk peektiwtss ssivmcgvdh eiadwswhdg ailpfdidkm (SEQ ID NO:8)
```

N9 (Accession No. ALH21371)

```
  1 mnpnqkilct sataiiigai avligianlg lniglhlkpg cncshsqpet tntsqtiinn
 61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpvt eintwarnil rtqesecvch ngvcpvvftd
241 gsatgpadtr iyyfkegkil wesltgtak hieecscyge rtgitctcrd nwqgsnrpvi
301 qidpvamtht sqyicspvlt dnprpndpni gkcndpypgn nnngvkqfsy ldgantwlgr
361 tistasrsgy emlkvpnalt ddrskpiqgq tivlnadwsg ysgsfmdywa egdcyracfy
421 velirgrpke dkvwwtsnsl vsmcsstefl gqwnwpdgak ieyfl (SEQ ID NO:9)
```

Figure 6

SEQ ID NO:10

MERIKELRNLMSQSRTREILTKTTVDHMAIIKKY
TSGRQEKNPALRMKWMMAMKYPITADKRITEM
IPERNEQGQTLWSKMNDAGSDRVMVSPLAVTW
WNRNGPMTNTVHYPKIYKTYFERVERLKHGTF
GPVHFRNQVKIRRRVDINPGHADLSAKEAQDVI
MEVVFPNEVGARILTSESQLTITKEKKEELQDCK
ISPLMVAYMLERELVRKTRFLPVAGGTSSVYIE
VLHLTQGTCWEQMYTPGGEVKNDDVDQSLIIA
ARNIVRRAAVSADPLASLLEMCHSTQIGGIRMV
DILKQNPTEEQAVDICKAAMGLRISSSFSFGGFT
FKRTSGSSVKREEEVLTGNLQTLKIRVHEGSEEF
TMVGRRATAILRKATRRLIQLIVSGRDEQSIAEA
IIVAMVFSQEDCMIKAVRGDLNFVNRANQRLNP
MHQLLRHFQKDAKVLFQNWGVEPIDNVMGMIG
ILPDMTPSIEMSMRGVRISKMGVDEYSSTERVV
VSIDRFLRVRDQRGNVLLSPEEVSETQGTEKLTI
TYSSSMMWEINGPESVLVNTYQWIIRNWETVKI
QWSQNPTMLYNKMEFEPFQSLVPKAIRGQYSGF
VRTLFQQMRDVLGTFDTAQIIKLLPFAAAPPKQ
SRMQFSSFTVNVRGSGMRILVRGNSPVFNYNKA
TKRLTVLGKDAGTLTEDPDEGTAGVESAVLRGF
LILGKEDRRYGPALSINELSNLAKGEKANVLIGQ
GDVVLVMKRKRDSSILTDSQTATKRIRMAIN

SEQ ID NO:11

MDVNPTLLFLKVPAQNAISTTFPYTGDPPYSHG
TGTGYTMDTVNRTHQYSEKGRWTTNTETGAPQ
LNPIDGPLPEDNEPSGYAQTDCVLEAMAFLEES
HPGIFENSCIETMEVVQQTRVDKLTQGRQTYDW
TLNRNQPAATALANTIEVFRSNGLTANESGRLID
FLKDVMESMKKEEMGITTHFQRKRRVRDNMTK
KMITQRTIGKRKQRLNKRGYLIRALTLNTMTKD
AERGKLKRRAIATPGMQIRGFVYFVETLARSICE
KLEQSGLPVGGNEKKAKLANVVRKMMTNSQDT
ELSFTITGDNTKWNENQNPRMFLAMITYMTRNQ
PEWFRNVLSIAPIMFSNKMARLGKGYMFESKSM

Figure 6 cont.

KLRTQIPAEMLASIDLKYFNDSTRKKIEKIRPLLI
EGTASLSPGMMMGMFNMLSTVLGVSILNLGQK
RYTKTTYWWDGLQSSDDFALIVNAPNHEGIQAG
VDRFYRTCKLLGINMSKKKSYINRTGTFEFTSFF
YRYGFVANFSMELPSFGVSGINESADMSIGVTVI
KNNMINNDLGPATAQMALQLFIKDYRYTYRCH
RGDTQIQTRRSFEIKKLWEQTRSKAGLLVSDGG
PNLYNIRNLHIPEVCLKWELMDEDYQGRLCNPL
NPFVSHKEIESMNNAVMMPAHGPAKNMEYDAV
ATTHSWIPKRNRSILNTSQRGVLEDEQMYQRCC
NLFEKFFPSSSYRRPVGISSMVEAMVSRARIDAR
IDFESGRIKKEEFTEIMKICSTIEELRRQK

SEQ ID NO:12

MEDFVRQCFNPMIVELAEKTMKEYGEDLKIETN
KFAAICTHLEVCFMYSDFHFINEQGESIIVELGD
PNALLKHRFEIIEGRDRTMAWTVVNSICNTTGA
EKPKFLPDLYDYKENRFIEIGVTRREVHIYYLEK
ANKIKSEKTHIHIFSFTGEEMATRADYTLDEESR
ARIKTRLFTIRQEMASRGLWDSFRQSERGEETIE
ERFEITGTMRKLADQSLPPNFSSLENFRAYVDGF
EPNGYIEGKLSQMSKEVNARIEPFLKTTPRPLRL
PNGPPCSQRSKFLLMDALKLSIEDPSHEGEGIPL
YDAIKCMRTFFGWKEPNVVKPHEKGINPNYLLS
WKQVLAELQDIENEEKIPKTKNMKKTSQLKWA
LGENMAPEKVDFDDCKDVGDLKQYDSDEPELR
SLASWIQNEFNKACELTDSSWIELDEIGEDVAPI
EHIASMRRNYFTSEVSHCRATEYIMKGVYINTA
LLNASCAAMDDFQLIPMISKCRTKEGRRKTNLY
GFIIKGRSHLRNDTDVVNFVSMEFSLTDPRLEPH
KWEKYCVLEIGDMLLRSAIGQVSRPMFLYVRTN
GTSKIKMKWGMEMRRCLLQSLQQIESMIEAESS
VKEKDMTKEFFENKSETWPIGESPKGVEESSIGK
VCRTLLAKSVFNSLYASPQLEGFSAESRKLLLIV
QALRDNLEPGTFDLGGLYEAIEECLINDPWVLL
NASWFNSFLTHALS

SEQ ID NO:13

Figure 6 cont.

MASQGTKRSYEQMETDGERQNATEIRASVGKMI
GGIGRFYIQMCTELKLSDYEGRLIQNSLTIERMV
LSAFDERRNKYLEEHPSAGKDPKKTGGPIYRRV
NGKWMRELILYDKEEIRRIWRQANNGDDATAG
LTHMMIWHSNLNDATYQRTRALVRTGMDPRMC
SLMQGSTLPRRSGAAGAAVKGVGTMVMELVRM
IKRGINDRNFWRGENGRKTRIAYERMCNILKGK
FQTAAQKAMMDQVRESRNPGNAEFEDLTFLAR
SALILRGSVAHKSCLPACVYGPAVASGYDFERE
GYSLVGIDPFRLLQNSQVYSLIRPNENPAHKSQL
VWMACHSAAFEDLRVLSFIKGTKVVPRGKLSTR
GVQIASNENMETMESSTLELRSRYWAIRTRSGG
NTNQQRASAGQISIQPTFSVQRNLPFDRTTVMA
AFTGNTEGRTSDMRTEIIRMMESARPEDVSFQG
RGVFELSDEKAASPIVPSFDMSNEGSYFFGDNA
EEYDN

SEQ ID NO:14

MSLLTEVETYVLSIIPSGPLKAEIAQRLEDVFAG
KNTDLEVLMEWLKTRPILSPLTKGILGFVFTLTV
PSERGLQRRRFVQNALNGNGDPNNMDKAVKLY
RKLKREITFHGAKEISLSYSAGALASCMGLIYNR
MGAVTTEVAFGLVCATCEQIADSQHRSHRQMV
TTTNPLIRHENRMVLASTTAKAMEQMAGSSEQA
AEAMEVASQARQMVQAMRTIGTHPSSAGLKN
DLLENLQAYQKRMGVQMQRFK

```
  1 mnpnqkiiti gsvcmtigma nlilqignii siwishsiql gnqnqietcn qsvityennt
 61 wvnqtyvnis ntnfaagqsv vsvklagnss lcpvsgwaiy skdnsvrigs kgdvfvirep
121 fiscsplecr tffltqgall ndkhsngtik drspyrtlms cpigevpspy nsrfesvaws
181 asachdginw ltigisqpdn gavavlkyng iitdtikswr nnilrtqese cacvngscft
241 vmtdgpsngq asykifriek gkivksvemn apnyhyeecs cypdsseitc vcrdnwhgsn
301 rpwvsfnqnl eyqigyicsq ifgdnprpnd ktqscqpvss ngangvkgfs fkygngvwig
361 rtksissrng femlwdpngw tgtdnnfsik qdivginews gysgsfvqhp eltgldcirp
421 cfwvelirgr pkentiwtsg ssisfcgvns dtvgwswpdg aelpftidk (SEQ ID
    NO:15)
```

N7

```
  1 mnpnqklfal sgvaialsil nlligisnvg lnvslhlkgs sdqdknwtct svtqnnttli
 61 entyvnnttv idketgtakp nylmlnkslc kvegwvvvak dnairfgese qiivtrepyv
121 scdplgckmy alhqgttirn khsngtihdr tafrqlistp lgsppvvsns dflcvgwsst
181 schdgigrmt icvqgnndna tatvyydrrl tttiktwagn ilrtqesecv chngtcvvim
241 tdgsassqay tkvlyfhkql vikeealkgs arhieecscy ghnskvtcvc rdnwqganrp
301 vieidmname htsqylctgv ltdtsrpsdk smgdcnnpit gspgapgvkg fqfldssntw
361 lgrtisprsr sgfemlkipn aetdpnskit erqeivdnnn wsgysgsfid ywdessecyn 421 pcfyvelirg rpeeakyvgw tsnslialcg spisvgsgsf pdgaqiqyfs (SEQ ID
    NO:16)
```

N9

```
  1 mnpnqkilct sataiiigai avligianlg lniglhlkpg cncshsqpet tntsqtiinn
 61 yynetnitni qmeertsrnf nnitkqlcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpva eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
    421 velirgrpke dkvwwtsnsi vsmcsstefl gqwnwpdgak ieyfl (SEQ ID
NO:17)
```

N2

```
  1 mnpnqkiiti gsvsltisti cffmqiaili ttvtlhfkqy efnsppnnqv mlceptiier
 61 niteivyltn ttiekeicpk laeyrnwskp qcnitgfapf skdnsirlsa ggdiwvtrep
```

Figure 7 cont.

```
121 yvscdpdkcy qfalgqgttl nnvhsndivh drtpyrtllm nelgvpfhlg tkqvciawss
181 sschdgkawl hvcvtgdden atasfiyngr ladsivswsk kilrtqesec vcingtctvv
241 mtdgsasgka dtkilfieeg kivhtstlsg saqhveecsc yprypgvrcv crdnwkgsnr
301 pivdinikdy sivssyvcsg lvgdtprknd ssssshcldp nneegghgvk gwafddgndv
361 wmgrtisekl rsgyetfkvi eqwsnpnskl qinrqvivdr gnrsgysgif svegkscinr
421 cfyvelirgr kqetevlwts nsivvfcgts gtygtgswpd gadinlmpi (SEQ ID
NO:18)
```

Figure 8

>A/Hong Kong/4801/2014NA(T148K)
ATGAATCCAAATCAAAAGATAATAACGATTGGCTCTGTTTCTCTCACCATTTCCACAATATGCTTTTTCATGC
AAATTGCCATTTTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTAACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATCAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACAAAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAAAGATATTCTCAGGACCCAGGAGTCAGAATGCATTTGTATCAATGGAACTTGT
ACAGTAGTAATGACTGATGGAAGTGCTTCAGGAAAAGCTGATACTAAAATACTATTCATTGAGGAGGGGA
AAATCGTTCATACTAGCACATTGTCAGGAAGTGCTCAGCATGTCGAAGAGTGCTCTTGCTATCCTCGATATC
CTGGTGTCAGATGTGTCTGCAGAGACAACTGGAAGGGCTCCAATCGGCCCATCGTAGATATAAACATAAA
GGATCATAGCATTGTTTCCAGTTATGTGTGTTCAGGACTTGTTGGAGACACACCCAGAAAAAACGACAGC
TCCAGCAGTAGCCATTGTTTGGATCCTAACAATGAAGAAGGTGGTCATGGAGTGAAAGGCTGGGCCTTT
GATGATGGAAATGACGTGTGGATGGGAAGAACAATCAACGAGACGTCACGCTTAGGGTATGAAACCTTC
AAAGTCATTGAAGGCTGGTCCAACCCTAAGTCCAAATTGCAGACAAATAGGCAAGTCATAGTTGACAGAG
GTGATAGGTCCGGTTATTCTGGTATTTTCTCTGTTGAAGGCAAAAGCTGCATAAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCCTATATAAGC
TTTCGCAATTTTAGAAAAAACT (SEQ ID NO:19)

> A/Hong Kong/4801/2014NA(T148K, D151E, H347G, T369K)
ATGAATCCAAATCAAAAGATAATAACGATTGGCTCTGTTTCTCTCACCATTTCCACAATATGCTTTTTCATGC
AAATTGCCATTTTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTAACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATCAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACAAAGTACGTGAAAGGACCCCTTATCGGACTCTATTGATGAATGAGTTGGGTGTTCCT
TTCCATCTGGGGACCAAGCAAGTGTGCATAGCATGGTCCAGCTCAAGTTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAAAGATATTCTCAGGACCCAGGAGTCAGAATGCATTTGTATCAATGGAACTTG
TACAGTAGTAATGACTGATGGAAGTGCTTCAGGAAAAGCTGATACTAAAATACTATTCATTGAGGAGGGG

Figure 8 cont.

AAAATCGTTCATACTAGCACATTGTCAGGAAGTGCTCAGCATGTCGAAGAGTGCTCTTGCTATCCTCGATAT
CCTGGTGTCAGATGTGTCTGCAGAGACAACTGGAAGGGCTCCAATCGGCCCATCGTAGATATAAACATAA
AGGATCATAGCATTGTTTCCAGTTATGTGTGTTCAGGACTTGTTGGAGACACACCCAGAAAAAACGACAG
CTCCAGCAGTAGCCATTGTTTGGATCCTAACAATGAAGAAGGTGGTGGCGGAGTGAAAGGCTGGGCCTT
TGATGATGGAAATGACGTGTGGATGGGAAGAACAATCAACGAGAAGTCACGCTTAGGGTATGAAACCTT
CAAAGTCATTGAAGGCTGGTCCAACCCTAAGTCCAAATTGCAGACAAATAGGCAAGTCATAGTTGACAGA
GGTGATAGGTCCGGTTATTCTGGTATTTTCTCTGTTGAAGGCAAAAGCTGCATAAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCCTATATAAG
CTTTCGCAATTTTAGAAAAAACT (SEQ ID NO:20)

> A/Alaska/232/2015NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACACAGTACGTGATAGGACCCCTTATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:21)

>A/Alaska/232/2015NA(T148K, D151E, N245S, G346V, T369K)
ATGAATCCAAATCAAAAGATAATAACGATTGGCTCTGTTTCTCTCACCATTTCCACAATATGCTTCTTCATGC

Figure 8 cont.

AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAAGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACACTAAACAAC
GTGCATTCAAATAACAAAGTACGTGAGAGGACCCCTTATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGCTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAGTGCTACAGGAAAAGCTGATACTAAAATACTATTCATTGAGGAGGG
GAAAATCGTTCATACTAGCAAATTGTCAGGAAGTGCTCAGCATGTCGAAGAGTGCTCTTGCTATCCTCGAT
ATCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAAACGACA
GCTCCAGCAGTAGCCATTGTTTGAATCCTAACAATGAAGAAGGTGTTCATGGAGTGAAAGGCTGGGCCTT
TGATGATGGAAATGACGTGTGGATGGGGAGAACAATCAACGAGAAGTCACGCTTAGGGTATGAAACCTT
CAAAGTCGTTGAAGGCTGGTCCAACCCTAAGTCCAAATTGCAGATAAATAGGCAAGTCATAGTTGACAGA
GGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:22)

A/Yokohama/147/2017NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAAGACAATTCGATTAGGCTTTCCGCTGGTGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAwATGGGAGGCTTGTAGAT
AGTGTTGTTTCATGGTCCAACGATATTCTCAGGACCCAGGAGTCAGAATGCGTTTGTATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGTTATGTGTGTTCAGGACTTGTTGGAGACACACCCAGAAAAAGCGACAG

Figure 8 cont.

CTCCAGCAGTAGCCATTGTTTGAATCCTAACAATGAAGAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATCAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:23)

>A/Yokohama/48/2018NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCCTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATGGCATGGTCCAGCTCAAGTTGTCACGATGGAAAAGCATGGC
TGCATGTTTGTATAACTGGGGATGATAAAAATGCAACTGCTAGCTTCATTTACAATGGGAGGCTTGTAGAT
AGTGTTGTTTCATGGTCCAAAGATATTCTCAGGACCCAGGAGTCAGAATGCGTTTGCATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCCTGCTATCCTCGATA
TCCTGGTGTCAGATGTGTCTGCAGAGACAACTGGAAAGGATCCAACCGGCCCATTGTAGATATAAACATA
AAGGATCATAGCATTGTTTCCAGTTATGTGTGTTCAGGACTTGTTGGAGACACACCCAGAAAAAGCGACA
GCTCCAGCAGTAGCCATTGTTTGAATCCTAACAATGAAGAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACTCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG
TGGCACCTCAGGTACATATGGAACAGGCTCATGGCCTGATGGGGCGGACCTCAATCTCATGCATATATAA
(SEQ ID NO:24)

>A/Delaware/33/2018NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG

Figure 8 cont.

GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTCTCATGGTCCAATGATATTCTCAGGACCCAGGAATCAGAATGCGTTTGTATCAATGGAACTTGTA
CAGTAGTAATGACTGATGGAAATGCTACAGGAAAAGCTGATACTAAAATACTATTCATTGAGGAGGGGAA
AATCGTTCATACTAGCAAATTGTCAGGAAGTGCTCAGCATGTCGAAGAGTGCTCTTGCTATCCTCGATATCC
TGGTGTCAGATGTGTCTGCAGAGACAACTGGAAAGGATCCAACCGGCCCATCATAGATATAAACATAAAG
GATCATAGCATTGTTTCCAGTTATGTGTGTTCAGGACTTGTTGGAGACACACCCAGAAAAAGCGACAGCT
CCAGCAGTAGCCATTGTTTGAATCCTAACAATGAAGAAGGTGGTCATGGAGTGAAAGGCTGGGCCTTTG
ATGATGGAAATGACGTGTGGATGGGGAGAACAATCAACGAGACGTCACGCTTAGGGTATGAAACCTTCA
AAGTCGTTGAAGGCTGGTCCAACCCTAAGTCCAAATTGCAGATAAATAGGCAAGTCTTAGTTGACAGAGG
TGATAGGTCCGGTTATTCTGGTATTTTCTCTGTTGAAGGCAAAAGCTGCATCAATCGGTGCTTTTATGTGGA
GTTGATTAGGGGAAGAAAAGAGGAAACTGAAGTCTTGTGGACCTCAAACAGTATTGTTGTGTTTTGTGG
CACCTCAGGTACATATGGAACAGGCTCATGGCCTGATGGGGCGGACCTCAATCTCATGCATATATAAGCTT
TCGCAATTTTAGAAAAAACT (SEQ ID NO:25)

>A/Tokyo/UT-GR85/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGAACAACACTAAACAACG
TGCATTCAAATAACACAGTACGTGATAGGACCCCTTATCGGACTCTATTGATGAATGAGTTGGGTGTTCCTT
TCCATCTGGGGACCAAGCAAGTGTGCATAGCATGGTCCAGCTCAAGTTGTCACGATGGAAAAGCATGGCT
GCATGTTTGTATAACGGGGGATGATAAAAATGCAACTGCTAGCTTCATTTACAATGGGAGGCTTGTAGATA
GTGTTGTTTCATGGTCCAACGATATTCTCAGGACCCAGGAGTCAGAATGCGTTTGTATCAATGGAACTTGT
ACAGTAGTAATGACTGATGGAAATGCTACAGGAAAGGCTGACACTAAAATACTATTCATTGAGGAGGGA
AAATCGTACATACTAGCAAATTGTCAGGAAGTGCTCAGCATGTCGAAGAGTGCTCTTGCTATCCTCGATATC
CTGGTGTCAGATGTGTCTGCAGAGACAACTGGAAAGGATCCAACCGGCCCATCATAGATATAAACATAAA
GGATCATAGCATTGTTTCCAGGTATGTGTGTTCAGGACTTGTTGGAGACACACCCAGAAAAAGCGACAGC
TCCAGCAGTAGCCATTGTTTGAACCCTAACAATGAAAAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG

Figure 8 cont

GTGATAGGTCCGGTTATTCTGGTATTTTCTCTGTTGAAGGCAAAAGCTGCATCAATCGGTGCTTTTATGTRG
AGTTGATTAGGGGAAGAAAAGAGGAAACTGAAGTCTTGTGGACCTCAAACAGTATTGTTGTGTTTTGTG
GCACCTCAGGTACATATGGAACAGGCTCATGGCCTGATGGGGCGGACCTCAATCTCATGCATATATAAGCT
TTCGCAATTTTAGAAAAAACTCCTTGTTTCTACTG (SEQ ID NO:26)

>A/Saint-Petersburg/RII-3245/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGGACAACACTAAACAACG
TGCATTCAAATAACACAGTACGTGATAGGACCCCTTACCGGACTCTATTGATGAATGAGTTGGGTGTTCCT
TTCCATCTGGGGACCAAGCAAGTGTGCATAGCATGGTCCAGCTCAAGTTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAATCAGAATGCGTTTGTATCAATGGAACTTG
TACAGTAGTAATGACTGATGGAAATGCTACAGGAAAAGCTGATACTAAAATACTATTCATCGAGGAGGGG
AAAATCATTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGTTATGTGTGTTCAGGACTTGTTGGAGACACACCCAGAAAAAGCGACAG
CTCCAGCAGTAGCCATTGTTTGAATCCTAACAATGAAGAAGGTGGTCATGGAGTGAAAGGCTGGGCCTTT
GATGATGGAAATGACGTGTGGATGGGGAGAACAATCAACGAGACGTCACGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAAGC
TTTCGCAATTTTAGAAAAAACTCCTTGTTTCTACT (SEQ ID NO:27)

>A/Kanagawa/IC1820/2019NA
ATGAATCCAAATCAAAAGATAATAACGATTGGCTCTGTTTCTCTCACAATTTCCACAATATGCTTCTTCATGC
AAATTGCCATCCTGATAACTACTGTAACATTGCATTTCAAGCAATATGAATTCAACTCCCCCCCAAATAACCA
AGTGATGCTGTGTGAACCAACAATAATAGAAAGAAACATAACAGAGATAGTGTATTTGACCAACACCACC
ATAGAGAAGGAAATATGCCCCAAACCAGCAGAATACAGAAATTGGTCAAAACCGCAATGTGGCATTACAG
GATTTGCACCTTTCTCTAAGGACAATTCGATTAGGCTTTCCGCTGGTGGGGACATCTGGGTGACAAGAGA
ACCTTATGTGTCATGCGATCTTGACAAGTGTTATCAATTTGCCCTTGGACAGGGGACAACACTAAACAACG
TGCATTCAAATAACACAGTACGTGATAGAACCCCTTATCGGACTCTATTGATGAATGAGTTGGGTGTTCCTT

Figure 8 cont.

TCCATCTGGGGACCAAGCAAGTGTGCATAGCATGGTCCAGCTCAAGCTGTCACGATGGAAAAGCATGGC
TGCATGTTTGTATAACGGGGGATGATAAAAATGCAACTGCTAGCTTCATTTACAATGGGAGGCTTGTAGAT
AGTGTTGTTTCATGGTCCAACGATATTCTCAGGACCCAGGAGTCAGAATGCGTTTGTATCAATGGAACTTG
TACAGTAGTAATGACTGATGGAAATGCTACAGGAAAAGCTGATACTAAAATACTATTCATTGAGGAGGGG
AAAATCGTTCATACTAGCAAATTGTCAGGAAGTGCTCAGCATGTCGAAGAGTGCTCTTGCTATCCTCGATAT
CCTGGTGTCAGATGTGTCTGCAGAGACAACTGGAAAGGATCCAACCGGCCCATCATAGATATAAACATAA
AGGATCATAGCATTGTTTCCAGGTATGTGTGTTCAGGACTTGTTGGAGACACACCCAGAAAAAGCGACAG
CTCCAGCAGTAGCCATTGTTTGAACCCTAACAATGAAAAAGGTGATCATGGAGTGAAAGGCTGGGCCTTT
GATGATGGAAATGACGTGTGGATGGGGAGAACAATCAACGAGACGTCGCGCTTAGGGTATGAAACCTTC
AAAGTCGTTGAAGGCTGGTCCAACCCTAAGTCCAAATTGCAGATAAATAGGCAAGTCATAGTTGACAGAG
GTGATAGGTCCGGTTATTCTGGTATTTTCTCTGTTGAAGGCAAAAGCTGCATCAATCGGTGCTTTTATGTG
GAGTTGATTAGGGGAAGAAAAGAGGAAACTGAAGTCTTGTGGACCTCAAACAGTATTGTTGTGTTTTGT
GGCACCTCAGGTACATATGGAACAGGCTCATGGCCTGATGGGGCGGACCTCAATCTCATGCATATATAA
(SEQ ID NO:28)

>A/Kansas/14/2017NA
ATGAATCCAAATCAAAAGATAATAACGATTGGCTCTGTTTCTCTCACCATTTCCACAATATGCTTCTTCATGC
AAATTGCCATCCTGATAACTACTGTAACATTGCATTTCAAGCAATATGAATTCAACTCCCCCCCAAACAACC
AAGTGATGCTGTGTGAACCAACAATAATAGAAAGAAACATAACAGAGATAGTGTATTTGACCAACACCAC
CATAGAGAGGGAAATATGCCCCAAACCAGCAGAATACAGAAATTGGTCAAAACCGCAATGTGGCATTACA
GGATTTGCACCTTTCTCTAAGGACAATTCGATTAGGCTTTCCGCTGGTGGGGACATCTGGGTGACAAGAG
AACCTTATGTGTCATGCGATCCTGACAAGTGTTATCAATTTGCCCTTGGACAGGGAACAACAATAAACAAC
GTGCATTCAAATAACACAGCACGTGATAGGACCCCTCATCGGACTCTATTGATGAATGAGTTGGGTGTTCC
TTTCCATCTGGGGACCAAGCAAGTGTGCATAGCATGGTCCAGCTCAAGTTGTCACGATGGAAAAGCATGG
CTGCATGTTTGTATAACGGGGGATGATAAAAATGCAACTGCTAGTTTCATTTACAATGGGAGGCTTGTAGA
TAGTGTTGTTTCATGGTCCAAAGATATTCTCAGGACCCAGGAGTCAGAATGCGTTTGTATCAATGGAACTT
GTACAGTAGTAATGACTGATGGAAATGCTACAGGAAAAGCTGATACTAAAATATTATTCATTGAGGAGGGG
AAAATCGTTCATACTAGCAAATTGTCAGGAAGTGCTCAGCATGTCGAAGAGTGCTCTTGCTATCCTCGATA
CCCTGGTGTCAGATGTGTCTGCAGAGACAACTGGAAAGGATCCAACCGGCCCATCGTAGATATAAACATA
AAGGATCATAGCATTGTTTCCAGTTATGTGTGTTCAGGACTTGTTGGAGACACACCCAGAAAAACCGACA
GCTCCAGCAGCAGCCATTGCTTGAATCCTAACAATGAAAAGGTGGTCATGGAGTGAAAGGCTGGGCCT
TTGATGATGGAAATGACGTGTGGATGGGGAGAACAATCAACGAGACGTCACGCTTAGGGTATGAAACCT
TCAAAGTCGTTGAAGGCTGGTCCAACCCTAAGTCCAAATTGCAGATAAATAGGCAAGTCATAGTTGACAG
AGGTGATAGGTCCGGTTATTCTGGTATTTTCTCTGTTGAAGGCAAAAGCTGCATCAATCGGTGCTTTTATGT
GGAGTTGATTAGGGGAAGAAAAGAGGAAACTGAAGTCTTGTGGACCTCAAACAGTATTGTTGTGTTTTG

Figure 8 cont.

TGGCACCTCAGGTACATATGGAACAGGCTCATGGCCTGATGGGGCGGACCTCAATCTCATGCATATATAAG
CTTTCGCAATTTTAGAAAAAACT (SEQ ID NO:29)

Figure 9. Exemplary influenza B neuraminidases

AGA18961

```
mlpstiqtlt lfltsggvll slyvsaslsy llysdillkf srteitaptm pldcanasnv 61
qavnrsatkg vtlllpepew myprlscpgs tfqkallisp hrfgetkgns apliirepfi 121
acgpkeckhf althyaaqpg gyyngtredr nklrhlisvk lgkiptvens ifhmaawsgs 181
achdgrewty igvdgpdsna llkikygeay tdtyhsyakn tlrtqesacn ciggdcylmi 241
tdgpasgise crflkiregr iikeifptgr vkhteectcg fasnktieca crdnsytakr 301
pfvklnvetd taeirlmcte tyldtprpnd gsitgpcesn gdkgsggikg gfvhqrmask 361
igrwysrtms ktkrmgmgly vkydgdpwtd sealalsqvm vsmeepgwys fgfeikdkkc 421
dvpcigiemv hdggkttwhs aataiyclmg sgqllwdtvt gvnmtl (SEQ ID NO:30)
```

ACT85963.1

```
mlpstiqtlt lfltsggvll slyvsaslsy llysdillkf spteitaptm pldcanasnv 61
qavnrsatkg vtlllpepew typrlscpgs tfqkallisp hrfgetkgns apliirepfi 121
acgpkeckhf althyaaqpg gyyngtredk nklrhlisvk lgkiptvens ifhmaawsgs 181
achdgrewty igvdgpdsna llkikygeay tdtyhsyann ilrtqesacn ciggdcylmi 241
tdgsasgise crflkiregr iikeifptgr vehteectcg fasnktieca crdnsytakr 301
pfvklnvetd taeirlmcte tyldtprpdd gsitgpcesn gdkgsggikg gfvhqrmask 361
igrwysrtms ktkrmgmgly vkydgdpwtd sdalalsqvm vsmeepgwys fgfeikdkkc 421
dvpcigiemv hdggkktwhs aataiyclmg sgqllwdtvt gvdmal (SEQ ID NO:31)
```

ABL77391.1

```
mlpstiqtlt lfltsggvll slyvsaslsy llysdillkf spteitaptm pldcanasnv 61
qavnrsatkg vtlllpepew typrlscpgs tfqkallisp hrfgetkgns apliirepfi 121
acgpkeckhf althyaaqpg gyyngtrgdr nklrhlisvk lgkiptvens ifhmaawsgs 181
achdgkewty igvdgpdnna llkikygeay tdtyhsyann ilrtqesacn ciggncylmi 241
tdgsasgvse crflkiregr iikeifptgr vkhteectcg fasnktieca crdnsytakr 301
pfvklnvetd taeirlmcte tyldtprpdd gsitgpcesn gdkgsggikg gfvhqrmask 361
igrwysrtms ktkrmgmgly vkydgdpwad sdalalsqvm vsmeepgwys fgfeikdkkc 421
dvpcigiemv hdggketwhs aataiyclmg sgqllwdtvt gvdmal (SEQ ID NO:32)
```

ABF21335.1

```
mlpstiqtlt lfltsggvll slyvsaslsy llysdillkf spkitaptmt ldcanasnvq 61
avnrsatkem tfllpepewt yprlscqgst fqkallisph rfgeargnsa pliirepfia 121
cgpkeckhfa lthyaaqpgg yyngtredrn klrhlisvkl gkiptvensi fhmaawsgsa 181
chdgrewtyi gvdgpdsnal ikikygeayt dtyhsyanni lrtqesacnc iggdcylmit 241
dgsasgiskc rflkiregri ikeifptgrv ehteectcgf asnktiecac rdnnytakrp 301
```

Figure 9 cont.

```
fvklnvetdt aeirlmctet yldtprpddg sitgpcesng dkgrggikgg fvhqrmaski 361
grwysrtmsk termgmelyv kydgdpwtds daldpsgvmv smkepgwysf gfeikdkkcd 421
vpcigiemvh dggkktwhsa ataiyclmgs gqllwdtvtg vdmal (SEQ ID NO:33)
```

AAA43743.1

```
mlpstiqtlt lfltsggvll slyvsaslsy llysdillkf sptkrtaptm sldcanvsnv 61
qavnrsatke mtfllpepew typrlscqgs tfqkallisp hrfgeargns apliirepfi 121
acgpkeckhf althyaaqpg gyyngtrkdr nklrhlisvk lgkiptvens ifhmaawsgs 181
achdgrewty igvdgpdsna likikygeay tdtyhsyann ilrtqesacn ciggdcylmi 241
tdgsasgisk crflkiregr iikeifptgr vehteectcg fasnktieca crdnsytakr 301
pfvklnvetd taeirlmcte tyldtprpdd gsitgpcesn gdkglggikg gfvhqrmask 361
igrwysrtms ktermgmely vkydgdpwtd sealapsgvm vsmkepgwys fgfeikdkkc 421
dvpcigiemv hdggketwhs aataiyclmg sgqllwdtvt gvdmal (SEQ ID NO:34)
```

AML44612.1 Influenza B virus (B/Victoria/3/2014)

```
mlpstiqtlt lfltsggvll slyvsaslsy llysdillkf srtevtapim pldcanasnv 61
qavnrsatkg vtpllpepew typrlscpgs tfqkallisp hrfgetkgns apliirepfi 121
acgpkeckhf althyaaqpg gyyngtrkdr nklrhlisvk lgkiptvens ifhmaawsgs 181
achdgrewty igvdgpdsna likikygeay tdtyhsyakn ilrtqesacn ciggdcylmi 241
tdgpasgise crflkiregr iikeifptgr vkhteectcg fasnktieca crdnsytakr 301
pfvklnvetd taeirlmctk tyldtprpnd gsitgpcesd qdegsggikg gfvhqrmask 361
igrwysrtms ktkrmgmgly vkydgdpwtd sealalsgvm vsmeepgwys fgfeikdkkc 421
dvpcigiemv hdggkttwhs aataiyclmg sgqllwdtvt gvnmtl (SEQ ID NO:35)
```

RECOMBINANT INFLUENZA VIRUSES WITH STABILIZED NA

CROSS-REFERENCE TO RELATED APPLICATIONS

This application is a divisional of U.S. application Ser. No. 17/155,625, filed Jan. 22, 2021, which claims the benefit of the filing date of U.S. application No. 62/965,225, filed on Jan. 24, 2020, the disclosure of which is incorporated by reference 20 to 30 herein.

STATEMENT OF GOVERNMENT FUNDING

This invention was made with government support under HHSN272201400008C awarded by the National Institutes of Health. The government has certain rights in the invention.

INCORPORATION BY REFERENCE OF SEQUENCE LISTING

A Sequence Listing is provided herewith as an xml file, "2356941.xml" created on Aug. 3, 2023, and having a size of 101,767 bytes. The content of the xml file is incorporated by reference herein in its entirety.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, inactivated virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains.

There are four general types of influenza viruses, Type A, Type B, Type C, and Type D, which are defined by the absence of serological cross reactivity between their internal proteins. Influenza Type A viruses are further classified into subtypes based on antigenic and genetic differences of their glycoproteins, the HA and NA proteins. All the known HA and NA subtypes (H1 to H18 and N1 to N11) have been isolated from aquatic birds, which are thought to act as a natural reservoir for influenza.

It has been suggested that antibodies against NA play important roles in preventing influenza virus infections. However, the current influenza vaccines, which are made by the inactivation of influenza viruses grown in eggs and purification of the virus antigen, are not able to elicit anti-NA antibodies efficiently.

SUMMARY

One of the causes of the low production of anti-NA antibodies is attributed to the structural instability of the NA protein, which works as a homo-tetramer. The NA tetramer may be disrupted during the antigen purification process. Therefore, the amount of NA contained in current vaccines is insufficient to elicit the production of anti-NA antibodies.

The present disclosure relates to influenza viruses with certain residue(s) or modifications in the NA protein that stabilize its natural homotetramer structure, and methods of making and using that virus, e.g., in a vaccine. In one embodiment, an isolated recombinant influenza virus comprising a neuraminidase (NA) viral segment encoding a NA monomer that forms virions having stabilized NA tetramers is provided. In one embodiment, the recombinant influenza virus has a modified NA stalk relative to a parental NA that results in stabilized tetramers. In one embodiment, the modified NA stalk has a deletion. In one embodiment, the modified NA stalk has an insertion relative to a parental NA. In one embodiment, the modified NA stalk has at least one amino acid substitution relative to a parental NA. In one embodiment, at least one substitution in the modified NA stalk is a cysteine substitution. In one embodiment, the modified NA stalk has at least two substitutions relative to a parental NA. In one embodiment, the NA has a cysteine at position 48 relative to the numbering of N1. In one embodiment, the NA has a cysteine at position 50 relative to the numbering of N1. In one embodiment, the NA has a cysteine at position 48 and position 50 relative to the numbering of N1. In one embodiment, the NA stalk is modified within residues 1 to 10 from the C-terminus of the transmembrane domain relative to a parental NA. In one embodiment, the NA stalk is modified within residues 10 to 20 from the C-terminus of the transmembrane domain. In one embodiment, the NA stalk is modified within residues 20 to 30 from the C-terminus of the transmembrane domain. In one embodiment, the NA stalk is modified within residues 30 to 50 from the C-terminus of the transmembrane domain. In one embodiment, the stalk domain begins at the first residue after the last residue in the transmembrane domain of NA up to the conserved cysteine, or one to two residues before the conserved cysteine, in the head region of NA that forms a disulfide bond (see Blumenkrantz et al., *J. Virol.*, 87:10539 (2013)). In one embodiment, the insertion in the NA stalk is an insertion of 1, 2, 3, 4 or 5, or 5 to 10, or 10 to 20, or more residues. In one embodiment, the deletion in the NA stalk is a deletion of 1, 2, 3, 4 or 5, or 5 to 10, or 10 to 20, or more residues. In one embodiment, a NA that has a cysteine is the stalk region is modified to include a second or third cysteine, e.g., within 1 to 10 or 1 to 5 residues of the other cysteine(s). In one embodiment, a NA has at least two cysteines in the stalk region that are within 1 to 2, 2 to 3, 3 to 4 or 5 up to residues of each other. In one embodiment, a NA has at least two cysteines in the stalk region, one of which is within 5 residues, either N-terminal or C-terminal, of residue 48 in the NA, and the other of which is within 5 residues, either N-terminal or C-terminal, of residue 50 in the NA. In one embodiment, the cysteines are adjacent to each other, e.g., at residues 46 and 47, residues 46, 47 and 48, residues 47 and 48, residues 47, 48 and 49, residues 48 and 49, residues 48, 49, and 50, residues 49 and 50, or residues 49, 50 and 51, and in one embodiment both are in the stalk region. In one embodiment, the cysteines are 2 residues apart and in one embodiment both are in the stalk region, e.g., the cysteines are at residues 46 and 48, 47 and 49, 48 and 50, 49 and 51, 50 and 52, 51 and 53, and the like. In one embodiment, the cysteines are 3 residues apart, e.g., the cysteines are at residues 45 and 48, 46 and 49, 47 and 50, 48 and 51, 49 and 52, 50 and 53, 51 and 54, and the like and in one embodiment both are in the stalk region. In one embodiment, the cysteines are 4 residues apart, e.g., the cysteines are at residues 44 and 48, 45 and 49, 46 and 50, 47 and 51, 48 and 52, 49 and 53, 50 and 54, 51 and 55, and the like and in one embodiment both are in the stalk region. In one embodiment, the stalk region has no more than 10, 9, 8, 7, 6, 5, 4, 3, 2 or 1 cysteine residues. In one embodiment, the cysteine(s) in the stalk region are in the N-terminal 30 residues of the stalk region. In one embodiment, the cysteine(s) in the stalk region are in the N-terminal 20 residues of the stalk region.

As described herein, a highly proliferative recombinant influenza viruses expressing structurally stabilized neuraminidase tetramers was prepared. In one embodiment, recombinant influenza viruses containing either NA-48C or NA-50C or both express stabilized NA tetramers and replicate efficiently. Thus, amino acid mutations in influenza NA that enable the generation of highly proliferative recombinant influenza viruses expressing structurally stabilized NA tetramers can be used to generate influenza vaccine strains that can be used to produce influenza vaccines containing a greater amount of NA antigen. Influenza vaccine strains containing a greater amount of NA antigen that can elicit anti-NA antibodies efficiently.

In one embodiment, a vaccine comprising an effective amount of the recombinant influenza virus or a portion thereof is provided. In one embodiment, the vaccine is a whole virus vaccine. In one embodiment, the vaccine is a split virus vaccine. In one embodiment, the vaccine is a subunit vaccine. In one embodiment, the vaccine further comprises an adjuvant. In one embodiment, the vaccine further comprises a pharmaceutically acceptable carrier. In one embodiment, the carrier is suitable for intranasal or intramuscular administration. In one embodiment, the vaccine further comprises at least one other influenza virus isolate.

In one embodiment, a method of preparing influenza virus having stabilized NA tetramers is provided. The method includes contacting a cell with one or more vectors comprising nucleic acid for an influenza virus NA segment encoding, for example, at least one cysteine in the stalk region, nucleic acid for an influenza virus PA segment, nucleic acid for an influenza virus a PB1 segment, nucleic acid for an influenza virus PB2 segment, nucleic acid for an influenza virus NP segment, nucleic acid for an influenza virus NS segment, nucleic acid for an influenza virus M segment, and nucleic acid for an influenza virus HA segment, in an amount effective to produce influenza virus having stabilized NA tetramers. In one embodiment, the NA is N1, N2, N3 or N5. In one embodiment, the NA is N4, N6, N7, N8 or N9. In one embodiment, the cell is a mammalian cell. In one embodiment, the cell is a Vero cell, 293T cell or MDCK cell.

In one embodiment, a method of making an influenza vaccine is provided. The method includes combining the recombinant virus with an adjuvant or treating the virus with an agent that inactivates the virus. In one embodiment, the method further comprises aliquoting a selected dose of the virus into a receptacle. In one embodiment, the adjuvant comprises immunostimulatory DNA sequences, bacterium-derived components, aluminum salt (alum) or squalene oil-in-water emulsion systems such as MF59 and AS03. In one embodiment, the agent chemically inactivates the virus. In one embodiment, the agent comprises formalin or beta-propiolactone. In one embodiment, the agent comprises a detergent, e.g., a non-ionic detergent, a cationic detergent or an anionic detergent. In one embodiment, the detergent comprises CTAB, Triton, SDS, Neodol 23-6, or sodium desoxycholate. In one embodiment, the method further comprises separating HA and NA from other viral components, e.g., using centrifugation and collection of soluble molecules.

In one embodiment, a method of preparing influenza virus is provided that includes contacting cells with the recombinant virus in an amount effective to yield progeny virus. In one embodiment, the virus is contacted with an avian egg. In one embodiment, the cells are mammalian cells. In one embodiment, the HA of the virus is H1, H3, H5 or H7.

Also provided is a method of preparing stabilized NA tetramers, comprising: contacting a cell with one or more vectors comprising nucleic acid for an influenza virus NA segment encoding at least one cysteine in the stalk region and nucleic acid for an influenza virus HA. In one embodiment, the method further comprises isolating NA and HA from the cell. In one embodiment, the cell is an insect cell.

Further provided is a method of immunizing an avian or a mammal, comprising: administering to the avian or the mammal a composition having an effective amount of the recombinant virus. In one embodiment, the composition comprises at least one other different influenza virus. In one embodiment, the mammal is a human. In one embodiment, the composition is administered intranasally or via injection.

BRIEF DESCRIPTION OF FIGURES

FIG. 2. Amino acid sequence of the NA of A/Yokohama/2017/2003 (SEQ ID NO:1).

FIG. 3. Amino acid sequence for the NA of A/Saitama/103/2014 (SEQ ID NO:2).

FIG. 4. Amino acid sequences for NA of mutant of A/Yokohama/2017/2003 (SEQ ID NO:3).

FIG. 5. Exemplary NA sequences for N3, N4, N6, N7, N8, and N9 (SEQ ID Nos. 4-9). The stalk region is indicated by red font, underlining.

FIG. 6. Exemplary viral backbone sequences (SEQ ID Nos.10-14).

FIG. 7. Exemplary NA sequences (SEQ ID Nos. 15-18). The stalk region is indicated by red font, underlining.

FIG. 8. Exemplary NA nucleic acid sequences (SEQ ID Nos 19-29).

FIG. 9. Exemplary influenza B virus NA sequences (SEQ ID Nos. 45-50). In one embodiment, the stalk region in the NA of influenza B virus may be from residue 38 to 86.

DETAILED DESCRIPTION

Definitions

Figure 1:
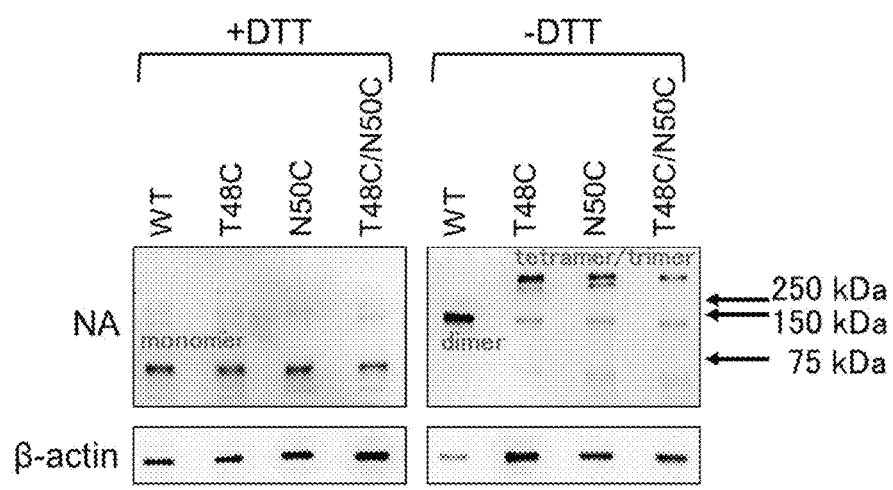
FIG. 1. Western blot to detect NA in hCK cells infected with influenza viruses.
Figure 10:
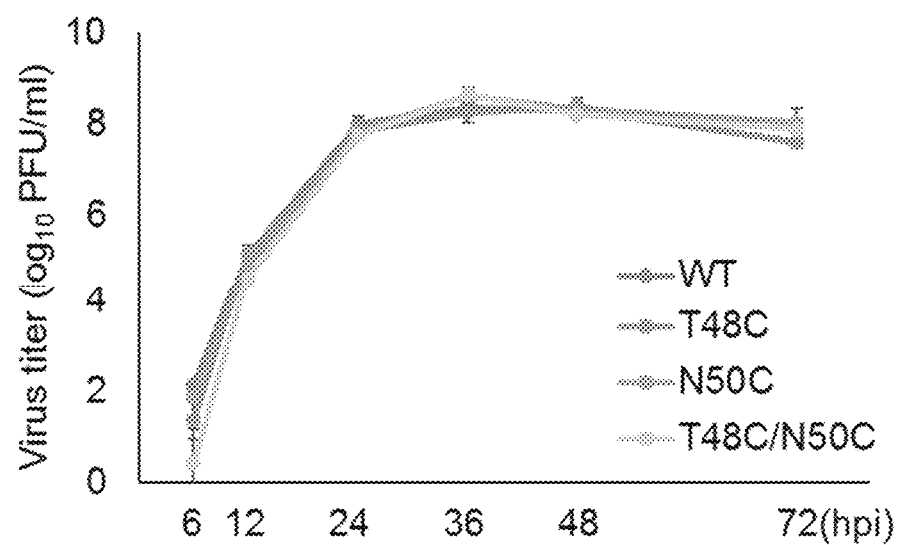
FIG. 10. Virus growth curves. 6+2 reassortant influenza viruses containing the HA and NA viral segments from A/Singapore/GP1908/2015 (H1N1) pdm09 in the backbone of high-yield A/Puerto Rico/8/1934 (H1N1) were prepared using reverse genetics and propagation in hCK cells at 37° C. Mutant viruses with either the NA-T48C or NA-N50C mutation or both mutations were generated. hCK cells were infected with these viruses at a MOI (multiplicity of infection) of 0.001. The supernatants were collected at the indicated times post-infection and virus titers were determined by means of plaque assay in hCK cells.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the disclosure, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus has only seven viral segments.

Cells that can be Used to Produce Virus

Any cell, e.g., any avian or mammalian cell, such as avian eggs, a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present disclosure, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, 0.1 to 2 µg, 0.5 to 5 µg, 1 to 10 µg, 10 µg to 20 µg, 15 µg to 30 µg, or 10 to 30 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present disclosure is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present disclosure may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present disclosure may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present disclosure may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present disclosure thus includes methods for preventing or attenuating a disorder or disease, e.g., an infection by at least one strain of pathogen such as an influenza virus. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present disclosure, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present disclosure, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{14}$, $10^3$-$10^{12}$, $10^2$-$10^{10}$, $10^5$-$10^1$, $10^6$-$10^{15}$, $10^2$-$10^{10}$, or $10^{15}$-$10^{20}$ plaque forming units (PFU)/kg, about $10^2$-$10^{10}$, $10^3$-$10^{12}$, $10^4$-$10^{10}$, $10^5$-$10^{11}$, $10^6$-$10^{14}$, $10^5$-$10^{12}$, or $10^{14}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 μg, 1 to 20 μg, 30 to 100 μg, 10 to 50 μg, 50 to 200 μg, or 150 to 300 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 0.1 μg to 1 μg, 0.5 μg to 5 μg, 1 μg to 10 μg, 10 μg to 20 μg, 15 μg to 30 μg, or 30 μg to 100 μg or any range or value therein, or the amount recommended by government agencies or recognized professional organizations. The quantity of NA can also be standardized.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children>3 years of age, and 7.5 μg per component for children<3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Viruses and Vaccine Formulations

The present disclosure provides a method that stabilizes the NA tetrameric structure of influenza virus, recombinant viruses having the stabilized NA, and methods of using that virus. For example, NA-48C and/or NA-50C mutations in influenza generate highly proliferative recombinant influenza viruses expressing structurally stabilized NA tetramers that can be used to generate influenza vaccine strains containing a greater amount of NA antigen, e.g., so as to elicit an effective immune response. The influenza vaccines can comprise live attenuated viruses or an inactivated (killed) preparation, e.g., whole virus, subunit or split virus preparation, or exogenously expressed NA and HA. There are three types of inactivated vaccines: whole virus vaccines, split virus vaccines (e.g., disrupted by a detergent), and subunit vaccines (i.e., HA and NA have been further purified by removal of other viral components). In one embodiment, the recombinant virus is grown in eggs and a split inactivated vaccine is prepared therefrom. In one embodiment, the dose in a vaccine contains about 10 to about 20, e.g., 15, µg of HA per strain (for example for a total HA concentration of 45 µg for trivalent and 60 µg for quadrivalent) and is administered as a single dose to those aged>9 years. Younger children (between 6 months and 8 years of age) may need two doses administered 4 weeks apart, if they have not been vaccinated in previous influenza seasons. The standard dose is typically delivered as an intramuscular (i.m.) injection (although intradermal [i.d.] formulations and intranasal formulations are also available).

In one embodiment, whole-virus vaccines are prepared from harvested allantoic fluid, chemically inactivated, e.g., with formalin or β-propiolactone, and subsequently concentrated and purified to remove nonviral protein contaminants. In one embodiment, the split-virus vaccine includes treatment with detergent to dissociate the viral lipid envelope, exposing all viral proteins and subviral elements. In one embodiment, for subunit vaccines, the HA (and NA) protein is further enriched through additional purification steps. Because the split-virus and subunit vaccines had comparable immunogenicity in primed populations but reduced reactogenicity compared to the whole-virus vaccine preparations, most contemporary vaccines since the 1970s have been split-virus or subunit formulations.

Exemplary NA Modifications

The present disclosure thus relates to influenza modification relative to parental NA that stabilize the neuraminidase (NA) tetramer, e.g., of human influenza viruses. Those NA modification(s) may also increase the vaccine virus yield.

Therefore, the disclosure provides isolated recombinant, e.g., reassortant, influenza viruses with selected amino acid residues, insertions, deletions, or any combination thereof, in the stalk region in NA. In one embodiment, the NA is selected to encode a cysteine at residue 48. In one embodiment, the NA is selected to encode a cysteine at position 50. In one embodiment, the NA is selected to encode a cysteine at positions 48 and 50.

In one embodiment, the NA is selected to have a deletion in one or more of residues 1 to 10 after the last residue in the transmembrane domain, which deletion stabilizes the NA tetramer. In one embodiment, the NA is selected to have a deletion in one or more of residues 10 to 20 after the last residue in the transmembrane domain that stabilizes the NA tetramer. In one embodiment, the NA is selected to have a deletion in one or more of residues 20 to 30 after the last residue in the transmembrane domain that stabilizes the NA tetramer. In one embodiment, the NA is selected to have a deletion in one or more of residues 30 to 40 after the last residue in the transmembrane domain that stabilizes the NA tetramer. In one embodiment, the NA is selected to have a deletion in one or more of residues 40 to 50 after the last residue in the transmembrane domain that stabilizes the NA tetramer. In one embodiment, the deletion includes a deletion of 1, 2, 3, 4 or 5 residues in the stalk region. In one embodiment, the deletion includes a deletion of 6, 7, 8, or 9 residues in the stalk region. In one embodiment, the deletion includes a deletion of 10, 11, 12, 13, 14 or 15 residues in the stalk region. In one embodiment, the deletion includes a deletion of 16, 17, 18, or 19 residues in the stalk region. In one embodiment, the deletion includes a deletion of 20, 21, 22, 23, 24 or 25 residues in the stalk region. In one embodiment, the deletion includes a deletion of 26, 27, 28, or 29 residues in the stalk region.

In one embodiment, the NA is selected to have an insertion of one or more amino acid residues in residues 1 to 10 after the last residue in the transmembrane domain, which insertion stabilizes the NA tetramer. In one embodiment, the NA is selected to have an insertion of one or more amino acid residues in residues 10 to 20 after the last residue in the transmembrane domain that stabilizes the NA tetramer. In one embodiment, the NA is selected to have an insertion of one or more amino acid residues 20 to 30 after the last residue in the transmembrane domain that stabilizes the NA tetramer. In one embodiment, the NA is selected to have an insertion of one or more amino acid residues 30 to 40 after the last residue in the transmembrane domain that stabilizes the NA tetramer. In one embodiment, the NA is selected to have an insertion of one or more amino acid residues 40 to 50 after the last residue in the transmembrane domain that stabilizes the NA tetramer. In one embodiment, the insertion includes an insertion of 1, 2, 3, 4 or 5 residues in the stalk region. In one embodiment, the insertion includes an insertion of 6, 7, 8, or 9 residues in the stalk region. In one embodiment, the insertion includes an insertion of 10, 11, 12, 13, 14 or 15 residues in the stalk region. In one embodiment, the insertion includes an insertion of 16, 17, 18, or 19 residues in the stalk region. In one embodiment, the insertion includes an insertion of 20, 21, 22, 23, 24 or 25 residues in the stalk region. In one embodiment, the insertion includes an insertion of 26, 27, 28, or 29 residues in the stalk region.

In one embodiment, the NA is selected to have a substitution of one or more amino acid residues in residues 1 to 10 after the last residue in the transmembrane domain, which substitution stabilizes the NA tetramer. In one embodiment, the NA is selected to have a substitution of one or more amino acid residues in residues 10 to 20 after the last residue in the transmembrane domain that stabilizes the NA tetramer. In one embodiment, the NA is selected to have a substitution of one or more amino acid residues 20 to 30 after the last residue in the transmembrane domain that stabilizes the NA tetramer. In one embodiment, the NA is selected to have a substitution of one or more amino acid residues 30 to 40 after the last residue in the transmembrane domain that stabilizes the NA tetramer. In one embodiment, the NA is selected to have a substitution of one or more amino acid residues 40 to 50 after the last residue in the transmembrane domain that stabilizes the NA tetramer. In one embodiment, the substitution to a cysteine is at a residue that faces towards the stalk region of a NA in another NA molecule, e.g., in a dimer, timer or tetramer.

In one embodiment, the NA is selected to have one or more cysteines at one or more of residues 1 to 10 after the last residue in the transmembrane domain that stabilizes the NA tetramer. In one embodiment, the NA is selected to have one or more cysteines at one or more of residues 10 to 20 after the last residue in the transmembrane domain that stabilizes the NA tetramer. In one embodiment, the NA is selected to have one or more cysteines at one or more of residues 20 to 30 after the last residue in the transmembrane domain that stabilizes the NA tetramer. In one embodiment, the NA is selected to have one or more cysteines at one or more of residues 30 to 40 after the last residue in the transmembrane domain that stabilizes the NA tetramer. In one embodiment, the NA is selected to have one or more cysteines at one or more of residues 40 to 50 after the last residue in the transmembrane domain that stabilizes the NA tetramer. For example, a virus with a NA having a 7 amino acid cytoplasmic tail, a 26 amino acid transmembrane domain and a Cys at residue 48, is a virus that has a cysteine at a residue that is between residues 10 to 20 after the last residue in the transmembrane domain (the numbering for NA is based on N1). In one embodiment, the disclosure provides an isolated recombinant reassortant influenza virus having six "internal" viral segments from a vaccine influenza virus, e.g., PR8UW, a NA viral segment with one or more of the specified modifications, and a HA viral segment, e.g., any of H1-H18, e.g., from a circulating influenza virus. Also provided are compositions comprising the recombinant influenza virus, pharmaceutical compositions such as vaccines.

Thus, for vaccine viruses that are to be grown or passaged in cells, e.g., in eggs, replacement of the residue at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, e.g., by mutation, or selection of a NA viral segment for a NA with a particular amino acid, e.g., cysteine, at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, wherein the numbering is based on N1, may result in stabilization of NA and/or higher viral titers.

In one embodiment, the disclosure provides an isolated recombinant influenza virus comprising PA, PB1, PB2, NP, NS, M, and HA viral segments and a NA viral segment that encodes an NA selected to encode a particular amino acid, e.g., cysteine, at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, wherein the numbering is based on N1, wherein the recombinant influenza virus may have enhanced replication in avian eggs or a NA tetramer with enhanced stability, e.g., during vaccine production.

In one embodiment, the disclosure provides an isolated recombinant influenza virus comprising PA, PB1, PB2, NP, NS, M, and HA viral segments and a NA viral segment that encodes an NA with a replacement (substitution) of a residue at any one of residues from 1 to 60 after the last residue in the transmembrane domain, an insertion of one or more residues from 1 to 60 after the last residue in the transmembrane domain or a deletion of one or more residues from 1 to 60 after the last residue in the transmembrane domain, or any combination thereof, in NA, e.g., by mutation, wherein the numbering is based on N1, wherein the recombinant influenza virus may have enhanced replication in avian eggs or a NA tetramer with enhanced stability, e.g., during vaccine production.

In one embodiment, the isolated recombinant influenza virus is a reassortant. In one embodiment, the NA viral segment encodes a NA that has at least 50%, 55%, 60%, 65%, 70%, 75%, 80%, 85%, 90%, 95%, or 99% amino acid sequence identity to any one of SEQ ID Nos. 1-9, 15-18, 37, or 44-50, or a polypeptide encoded by any one of SEQ ID Nos. 19-29, or having at least 50%, 55%, 60%, 65%, 70%, 75%, 80%, 85%, 90%, 95%, or 99% amino acid sequence identity to the stalk region in any one of SEQ ID Nos. 1-9, 15-18, 37, or 44-50, or encoded by one of SEQ ID Nos. 19-29. In one embodiment, the NA viral segment encodes a N2, N3, N7, or N9 and the positions in N3, N7, or N9 with the specified modification(s). In one embodiment, the NA viral segment encodes a N1, N4, N5, N6, N8, N10 or N11 with the specified modification(s). In one embodiment, the PA, PB1, PB2, NP, M, and NS viral segments have at least 85% nucleic acid sequence identity to SEQ ID Nos. 30 to 35 or 38 to 43 or encode a polypeptide having at least 80%, 85%, 90%, 95%, or 99 amino acid sequence identity to a polypeptide encoded by SEQ ID Nos. 30-35 or 38 to 43. In one embodiment, the virus is an influenza B virus.

Also provided is a method to prepare influenza virus having a stabilized NA tetramer. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production has a modification in the stalk region as described herein, wherein the numbering for NA residues is that for N1; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally comprising one or more of: a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2; in an amount effective to yield infectious influenza virus. In one embodiment, the NA viral segment encodes a NA that has at least 50%, 55%, 60%, 65%, 70%, 75%, 80%, 85%, 90%, 95%, or 99% amino acid sequence identity to any one of SEQ ID Nos. 1-9, 15-18, 37, or 44-50, or having at least 50%, 55%, 60%, 65%, 70%, 75%, 80%, 85%, 90%, 95%, or 99% amino acid sequence identity to the stalk region in any one of SEQ ID Nos. 1-9, 15-18, 37, or 44-50. In one embodiment, the NA is N1, N4, N5, N6, N8, N10 or N11.

In one embodiment, the HA is H1, H3, H5, H7, or H9. In one embodiment, the virus is an influenza A virus. In one embodiment, PA, PB1, PB2, NP, M, and NS viral segments have at least 85%, 85%, 90%, 95%, or 99% nucleic acid sequence identity to SEQ ID Nos. 30 to 35 or 38 to 43 or encode a polypeptide having at least 80%, 85%, 90%, 95%, or 99% amino acid sequence identity to a polypeptide encoded by SEQ ID Nos. 30-35 or 38 to 43. In one embodiment, HA is H2, H4, H5, H6, H8, or any of H10-H18.

In one embodiment, the virus is an influenza B virus.

Further provided is a method of immunizing an avian or a mammal with a composition having an effective amount of the virus described herein. In one embodiment, the composition comprises at least one other different influenza virus. In one embodiment, the mammal is a human. In one embodiment, the composition is administered intranasally or via injection.

In one embodiment, the disclosure provides isolated influenza type A virus with a characteristic residue(s), insertion and/or deletion, or a combination thereof, in NA described herein. In one embodiment, the isolated influenza type A virus with a characteristic residue(s), insertion and/or deletion, or a combination thereof, has a NA with at least 50%, 55%, 60%, 65%, 70%, 75%, 80%, 85%, 90%, 95%, or 99% amino acid sequence identity to any one of SEQ ID Nos. 1-9, 15-18, 37, or 44-50, or a polypeptide encoded by any one of SEQ ID Nos. 19-29, or having at least 50%, 55%, 60%, 65%, 70%, 75%, 80%, 85%, 90%, 95%, or 99% amino acid sequence identity to the stalk region in any one of SEQ ID Nos. 1-9, 15-18, 37, or 44-50 or encoded by one of SEQ ID Nos. 19-29.

In one embodiment, the isolated influenza type A virus of the invention with a characteristic residue(s) and/or deletion, or a combination thereof, has an HA from any one of subtypes 1-18 of HA. In one embodiment the characteristic residue is a conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine. In one embodiment, the characteristic residue is a non-conservative substitution.

In one embodiment, a mutation is introduced into a NA viral segment of an influenza virus isolate, e.g., via recombinant DNA techniques including site-specific mutagenesis, or replacing a portion of the NA coding sequence with a portion that includes the characteristic residue(s), insertion or deletion. In one embodiment, a NA viral segment with a characteristic residue, insertion and/or deletion described herein is combined with a HA segment, and internal viral segments of an influenza vaccine virus.

The disclosure provides a plurality of influenza virus vectors of the invention, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a HA viral segment that is from a different (second) viral isolate than the vaccine virus, and a NA viral segment with a characteristic residue(s), insertion, and/or deletion, or a combination thereof, as described herein, which is from a different viral source than the HA segment and the vaccine virus; a 6:2 reassortant is an influenza virus with 6 internal viral segments from a vaccine virus, and a NA viral segment having a characteristic residue(s), insertion and/or deletion, or a combination thereof, which segment is from the same source as the HA segment, and a HA viral segment from a different viral isolate than the vaccine virus; and a 7:1 reassortant, in one embodiment, is an influenza virus with 6 internal viral segments and a HA segment from a vaccine virus, and a NA segment that is modified to include the characteristic residue(s) and/or deletion, or a combination thereof, which NA segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6@ cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. For example, the DNAs for vRNA production include influenza B virus PA, PB1, PB2, NP, NS, and M or influenza B virus PA, PB1, PB2, NP, NS, M, and NA, wherein the vRNA for NA has a NA with a characteristic residue, insertion and/or deletion as described herein. The DNAs for vRNA production of NA and HA may be from different strains or isolates (6:1:1 reassortants) or from the same strain or isolate (6:2 reassortants), or the NA or HA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$ PFU/mL, e.g., at least $10^8$ PFU/mL, or high titers in two of more of those host cells.

Other reassortants with internal genes from other PR8 isolates or vaccine viruses may be employed in recombinant reassortant viruses.

In one embodiment, the DNAs for the internal genes for PB1, PB2, PA, NP, M, and NS encode proteins with substantially the same activity as a corresponding polypeptide encoded by one of SEQ ID NOs:30-35 or 38-43. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:30-35 or 38-43. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:30-35 or 38-43 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs: 30-35 or 38-43. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs: 30-35 or 38-43. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:30-35.

In one embodiment, the nucleic acid is a sequence encoding a NA polypeptide which is substantially the same as, e.g., having at least 50%, 55%, 60%, 65%, 70%, 75%, 80%, e.g., 90%, 92%, 95%, 97% or 99%, including any integer between 80 and 99, contiguous amino acid sequence identity to, one of Accession Nos. ACP41107.1 (N1), AIK26357.1 (N7), ALH21372.1 (N9), or BAK86313.1 (N2), the sequences of which are incorporated by reference herein, or at least the stalk region thereof. In one embodiment, the isolated and/or purified nucleic acid molecule encodes a polypeptide having at least 50%, 55%, 60%, 65%, 70%, 75%, 80%, e.g., 90%, 92%, 95%, 97% or 99%, including any integer between 80 and 99, contiguous amino acid sequence identity to any one of Accession Nos. ACP41107.1 (N1), AIK26357.1 (N7), ALH21372.1 (N9), or BAK86313.1 (N2), the sequences of which are incorporated by reference herein, or at least the stalk region thereof. In one embodiment, the influenza virus polypeptide has one or more, for instance, 2, 5, 10, 15, 20 or more, conservative amino acids substitutions, e.g., conservative substitutions of up to 10% or 20% of the residues, relative to SEQ ID NOs:1-18, or one of Accession Nos. ACP41107.1 (N1) AIK26357.1 (N7), ALH21372.1 (N9), or BAK86313.1 (N2), or at least the stalk region thereof. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide having one of SEQ ID NOs:1-18, 3, or one of Accession Nos. ACP41107.1 (N1) AIK26357.1 (N7), ALH21372.1 (N9), or BAK86313.1 (N2), or at least the stalk region thereof.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields *Virology* (Fields et al. (eds.), Lippincott, Williams and Wickens (2013), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase II transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:30-35, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:30-35. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

One example of an influenza A virus (A/Yokohama/2013/2003(H3N2)) neuraminidase protein sequence and its stalk region is provided below (stalk region is underlined).

```
                                              (SEQ ID NO: 1)
MNPNQKIITI GSVSLTISTI CFFMQIAILI TTVTLHFKQY

EFNSPPNNQV MLCEPTIIER NITEIVYLTN TTIEKEICPK

LAEYRNWSKP QCNITGFAPF SKDNSIRLSA GGDIWVTREP

YVSCDPDKCY QFALGQGTTL NNVHSNDIVH DRTPYRTLLM

NELGVPFHLG TKQVCIAWSS SSCHDGKAWL HVCVTGDDEN

ATASFIYNGR LADSIVSWSK KILRTQESEC VCINGTCTVV

MTDGSASGKA DTKILFIEEG KIVHTSTLSG SAQHVEECSC

YPRYPGVRCV CRDNWKGSNR PIVDINIKDY SIVSSYVCSG

LVGDTPRKND SSSSSHCLDP NNEEGGHGVK GWAFDDGNDV

WMGRTISEKL RSGYETFKVI EGWSNPNSKL QINRQVIVDR

GNRSGYSGIF SVEGKSCINR CFYVELIRGR KQETEVLWTS

NSIVVFCGTS GTYGTGSWPD GADINLMPI
```

Another example of an influenza A virus (A/Yokohama/47/2002(H1N2)) neuraminidase sequence and its stalk region is shown below (stalk region is underlined).

```
                                              (SEQ ID NO: 3)
MNPNQKIITI GSVSLTIATI CFLMQIAILV TTVTLHFKQY

ECNSPPNNQV MLCEPTIIER NITEIVYLTN TTIEKEICPK

LAEYRNWSKP QCNITGFAPF SKDNSIRLSA GGDIWVTREP

YVSCDPDKCY QFALGQGTTL NNGHSNDTVH DRTPYRTLLM
```

-continued
```
NELGVPFHLG TKQVCIAWSS SSCHDGKAWL HVCVTGDDGN

ATASFIYNGR LVDSIGSWSK KILRTQESEC VCINGTCTVV

MTDGSASGKA DTKILFIEEG KIVHTSLLSG SAQHVEECSC

YPRYPGVRCV CRDNWKGSNR PIVDINVKDY SIVSSYVCSG

LVGDTPRKND SSSSSHCLDP NNEEGGHGVK GWAFDDGNDV

WMGRTISEKL RSGYETFKVI EGWSKPNSKL QINRQVIVDR

GNRSGYSGIF SVEGKSCINR CFYVELIRGR NQETEVLWTS

NSIVVFCGTS GTYGTGSWPD GADINLMPI
```

The amino acid sequence for Singapore0019 NA and its stalk region is as follows (stalk region is underlined):

```
                                              (SEQ ID NO: 2)
M N P N Q K I I T I G S V S L T I S T I C F F M Q

I A I L I T T V T L H F K Q Y E F N S P P N N Q V

M L C E P T I I E R N I T E I V Y L T N T T I E K

E I C P K P A E Y R N W S K P Q C G I T G F A P F

S K D N S I R L S A G G D I W V T R E P Y V S C D

P D K C Y Q F A L G Q G T T L N N V H S N N T V R

D R T P Y R T L L M N E L G V P F H L G T K Q V C

I A W S S S S C H D G K A W L H V C I T G D D K N

A T A S F I Y N G R L I D S V V S W S K D I L R T

Q E S E C V C I N G T C T V V M T D G N A T G K A

D T K I L F I E E G K I V H T S K L S G S A Q H V

E E C S C Y P R Y P G V R C V C R D N W K G S N R

P I V D I N I K D H S I V S S Y V C S G L V G D T

P R K N D S S S S S H C L N P N N E E G G H G V K

G W A F D D G N D V W M G R T I N E T S R L G Y E

T F K V V E G W S N P K S K L Q I N R Q V I V D R

G D R S G Y S G I F S V E G K S C I N R C F Y V E

L I R G R K E E T E V L W T S N S I V V F C G T S

G T Y G T G S W P D G A D L N L M H I.
```

The NA for A/Alaska/232/2015 has the following sequence (stalk region is underlined):

```
                                             (SEQ ID NO: 44)
mnpnqkiiti gsvsltisti cffmqiaili ttvtlhfkqy efnsppnnqv mlceptiier niteivyltn ttiekeicpk paeyrnwskp qcgitgfapf skdnsirlsa ggdiwvtrep yvscdpdkcy qfalgqgttl nnvhsnntvr drtpyrtllm nelgvpfhlg tkqvciawss sschdgkawl hvcitgddkn atasfiyngr lvdsvvswsk dilrtqesec vcingtctvv mtdgnatgka dtkilfieeg kivhtsklsg saqhveecsc yprypgvrcv crdnwkgsnr pivdinikdh sivssyvcsg lvgdtprknd sssshclnp nneegghgvk gwafddgndv wmgrtinets rlgyetfkvv egwsnpnskl qinrqvivdr gdrsgysgif svegkscinr
```

-continued cfyvelirgr keetevlwts nsivvfcgts gtygtgswpd gadlnlmhi.

NA nucleotide sequence for A/Singapore/GP1908/2015 (H1N1) pdm09

(SEQ ID NO: 36)

agtttaaaatgaatccaaaccaaaagataataaccattggttcgatcagtatgacaattggaatggctaacttaatattacaaattgg aaacataatctcaatatgggttagccactcaattcaaattggaaatcaaagccagattgaaacatgcaatcaaagcgtcattacttat gaaaacaacacttgggtaaatcagacatatgttaacatcagcaacaccaactttgctgctggacagtcagtggtttccgtgaaattag cgggcaattcctctctctgccctgttagtggatggctatatacagtaaagacaacagtgtaagaatcggttccaaggggggatgtgtt tgtcataagggaaccattcatatcatgctctcccttggaatgcagaaccttcttcttgactcaagggccttgctaaatgacaaacat tccaatggaaccattaaagacaggagcccatatcgaaccctaatgagctgtcctattggtgaagttccctctccatacaactcaagat ttgagtcagtcgcttggtcagcaagtgcttgtcatgatggcatcaattggctaacaattggaatttctgcccagacagtggggcagt ggctgtgttaaagtacaatggcataataacagacactatcaagagttggaggaacaatatattgagaacacaagagtctgaatgtgca tgtgtaaatggttcttgctttaccataatgaccgatggaccaagtgatggacaggcctcatacaaaatcttcagaatagaaaagggaa agataatcaaatcagtcgaaatgaaagcccctaattatcactatgaggaatgctcctgttaccctgattctagtgaaatcacatgtgt gtgcagggataactggcatggctcgaatcgaccgtgggtgtctttcaaccagaatctggaatatcagatgggatacatatgcagtggg gttttcggagacaatccacgccctaatgataagacaggcagttgtggtccagtatcgtctaatggagcaaatggagtaaaaggatttt cattcaaatacggcaatggtgtttggatagggagaactaaaagcattagttcaagaaaaggttttgagatgatttgggatccgaatgg atggactgggactgacaataaattctcaataaagcaagatatcgtaggaataaatgagtggtcagggtatagcgggagttttgttcag catccagaactaacagggctggattgtataagaccttgcttctgggttgaactaataagagggcgacccgaagagaacacaatctgga ctagcgggagcagcatatcctttgtggtgtaaacagtgacactgtgggttggtcttggccagacggtgctgagttgccatttaccat tgacaagtaatttgttcaaaaaact Amino acid sequence for NA of A/Singapore/GP1908/2015 (H1N1) pdm09 (stalk is underlined)

(SEQ ID NO: 37)

MNPNQKIITIGSISMTIGMANLILQIGNIISIWVSH<u>SIQIGNQSQIETCNQSVITYENNTWVN</u>

<u>QTYVNISNTNFAAGQSVVSVKLAGNSS</u>LCPVSGWAIYSKDNSVRIGSKGDVFVIREPFISC

SPLECRTFFLTQGALLNDKHSNGTIKDRSPYRTLMSCPIGEVPSPYNSRFESVAWSASACH

DGINWLTIGISGPDSGAVAVLKYNGIITDTIKSWRNNILRTQESECACVNGSCFTIMTDGP

SDGQASYKIFRIEKGKIIKSVEMKAPNYHYEECSCYPDSSEITCVCRDNWHGSNRPWVSF

NQNLEYQMGYICSGVFGDNPRPNDKTGSCGPVSSNGANGVKGFSFKYGNGVWIGRTKS

ISSRKGFEMIWDPNGWTGTDNKFSIKQDIVGINEWSGYSGSFVQHPELTGLDCIRPCFWV

ELIRGRPEENTIWTSGSSISFCGVNSDTVGWSWPDGAELPFTIDK

In some cases, in one or more modifications can also be introduced into HA, PA, PB1, PB2, NP, M1, M2, NS2, PB1-F2, PA-X, and/or NS1 proteins (and nucleic acids encoding such proteins).

Besides enhanced stability during vaccine production, enhanced growth of the virus when passaged through embryonated chicken eggs or cultured cells may be observed when the modified NA proteins are expressed and such expression may result in significantly higher viral titers. Thus, the invention provides a method for making influenza viruses with enhanced replication in cell culture or embryonated eggs. The method includes providing cells suitable for influenza vaccine production; infecting the cells with viruses having modified neuraminidase; and isolating virus strains with enhanced growth relative to the one or more unmodified viral isolates. In some cases, a method for making influenza viruses with enhanced replication in cell culture can involve, serially culturing one or more influenza virus isolates in embryonated chicken eggs; and isolating serially cultured virus with enhanced growth relative to the one or more isolates prior to serial culture. In some cases, the viruses can be grown or passaged within cells in culture, e.g., MDCK or Vero cells.

As discussed herein, the modified neuraminidases can be expressed in a variety of influenza strains. For example, A/Puerto Rico/8/34 (H1N1), "PR8," virus often serves as the genetic backbone for generation of inactivated influenza vaccines.

In one embodiment, vectors for vRNA production can include a vector comprising a promoter operably linked to a modified NA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6@ cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). Vectors for mRNA production can include a vector encoding a modified NA, a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8(Cam) NS ("1"); 6:1:1 reassortants having UW-PR8 (modified) NA, PB1, PB2, PA, NP, and M ("6") and PR8(Cam) NS ("1"); and 7:1 reassortants having UW-PR8 PB1, PB2, PA, NP, M, (modified) NA, and NS ("7") may be employed.

The neuraminidases that can be modified can have any sequence including but not limited to the sequences described herein. However, in some cases, the modified neuraminidases can have substantially the same activity as a corresponding polypeptide described by sequence herein. As used herein, "substantially the same activity" includes an activity that is about 0.1%, 1%, 10%, 30%, 50%, 90%, e.g., up to 100% or more activity, or a detectable protein level that is about 80%, 90% or more protein level, of the corresponding protein described herein. In one embodiment, the nucleic acid encodes a polypeptide which is substantially the same as, e.g., having at least 80%, e.g., 90%, 92%, 95%, 97%, 98%, or 99%, including any integer between 80 and 99, contiguous amino acid sequence identity to a polypeptide encoded by one of sequences described herein. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of the nucleic acid sequences described herein. In one embodiment, a nucleic acid also encodes a polypeptide having at least 80%, e.g., 90%, 92%, 95%, 97%, 98%, or 99%, including any integer between 80 and 99, contiguous amino acid sequence identity to a polypeptide described herein.

Exemplary viral sequences for a master vaccine strain (PR8UW) are as follows:

```
PA
                                                                    (SEQ ID NO: 30)
AGCGAAAGCA GGTACTGATC CAAAATGGAA GATTTTGTGC GACAATGCTT CAATCCGATG

ATTGTCGAGC TTGCGGAAAA AACAATGAAA GAGTATGGGG AGGACCTGAA AATCGAAACA

AACAAATTTG CAGCAATATG CACTCACTTG GAAGTATGCT TCATGTATTC AGATTTTCAC

TTCATCAATG AGCAAGGCGA GTCAATAATC GTAGAACTTG GTGATCCAAA TGCACTTTTG

AAGCACAGAT TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT GTATGATTAC

AAGGAGAATA GATTCATCGA AATTGGAGTA ACAAGGAGAG AAGTTCACAT ATACTATCTG

GAAAAGGCCA ATAAAATTAA ATCTGAGAAA ACACACATCC ACATTTTCTC GTTCACTGGG

GAAGAAATGG CCACAAAGGC AGACTACACT CTCGATGAAG AAAGCAGGGC TAGGATCAAA

ACCAGACTAT TCACCATAAG ACAAGAAATG GCCAGCAGAG GCCTCTGGGA TTCCTTTCGT

CAGTCCGAGA GAGGAGAAGA GACAATTGAA GAAAGGTTTG AAATCACAGG AACAATGCGC

AAGCTTGCCG ACCAAAGTCT CCCGCCGAAC TTCTCCAGCC TTGAAAATTT TAGAGCCTAT

GTGGATGGAT TCGAACCGAA CGGCTACATT GAGGGCAAGC TGTCTCAAAT GTCCAAAGAA

GTAAATGCTA GAATTGAACC TTTTTTGAAA ACAACACCAC GACCACTTAG ACTTCCGAAT

GGGCCTCCCT GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA ATGCATGAGA

ACATTCTTTG GATGGAAGGA ACCCAATGTT GTTAAACCAC ACGAAAAGGG AATAAATCCA
```

-continued

```
AATTATCTTC TGTCATGGAA GCAAGTACTG GCAGAACTGC AGGACATTGA GAATGAGGAG

AAAATTCCAA AGACTAAAAA TATGAAGAAA ACAAGTCAGC TAAAGTGGGC ACTTGGTGAG

AACATGGCAC CAGAAAAGGT AGACTTTGAC GACTGTAAAG ATGTAGGTGA TTTGAAGCAA

TATGATAGTG ATGAACCAGA ATTGAGGTCG CTTGCAAGTT GGATTCAGAA TGAGTTTAAC

AAGGCATGCG AACTGACAGA TTCAAGCTGG ATAGAGCTCG ATGAGATTGG AGAAGATGTG

GCTCCAATTG AACACATTGC AAGCATGAGA AGGAATTATT TCACATCAGA GGTGTCTCAC

TGCAGAGCCA CAGAATACAT AATGAAGGGA GTGTACATCA ATACTGCCTT GCTTAATGCA

TCTTGTGCAG CAATGGATGA TTTCCAATTA ATTCCAATGA TAAGCAAGTG TAGAACTAAG

GAGGGAAGGC GAAAGACCAA CTTGTATGGT TTCATCATAA AAGGAAGATC CCACTTAAGG

AATGACACCG ACGTGGTAAA CTTTGTGAGC ATGGAGTTTT CTCTCACTGA CCCAAGACTT

GAACCACATA AATGGGAGAA GTACTGTGTT CTTGAGATAG GAGATATGCT TATAAGAAGT

GCCATAGGCC AGGTTTCAAG GCCCATGTTC TTGTATGTGA GAACAAATGG AACCTCAAAA

ATTAAATGA AATGGGGAAT GGAGATGAGG CGTTGCCTCC TCCAGTCACT TCAACAAATT

GAGAGTATGA TTGAAGCTGA GTCCTCTGTC AAAGAGAAAG ACATGACCAA AGAGTTCTTT

GAGAACAAAT CAGAAACATG GCCCATTGGA GAGTCCCCCA AAGGAGTGGA GGAAAGTTCC

ATTGGGAAGG TCTGCAGGAC TTTATTAGCA AAGTCGGTAT TCAACAGCTT GTATGCATCT

CCACAACTAG AAGGATTTTC AGCTGAATCA AGAAAACTGC TTCTTATCGT TCAGGCTCTT

AGGGACAACC TGGAACCTGG GACCTTTGAT CTTGGGGGGC TATATGAAGC AATTGAGGAG

TGCCTGATTA ATGATCCCTG GGTTTTGCTT AATGCTTCTT GGTTCAACTC CTTCCTTACA

CATGCATTGA GTTAGTTGTG GCAGTGCTAC TATTTGCTAT CCATACTGTC CAAAAAGTA

CCTTGTTTCT ACT
```

PB1
(SEQ ID NO: 31)
```
AGCGAAAGCAGGCAAACCATTTGAATGGATGTCAATCCGACCTTACTTTTCTTAAAAGTGCCAGCACA

AAATGCTATAAGCACAACTTTCCCTTATACTGGAGACCCTCCTTACAGCCATGGGACAGGAACAGGA

TACACCATGGATACTGTCAACAGGACACATCAGTACTCAGAAAAGGGAAGATGGACAACAAACACCG

AAACTGGAGCACCGCAACTCAACCCGATTGATGGGCCACTGCCAGAAGACAATGAACCAAGTGGTTA

TGCCCAAACAGATTGTGTATTGGAGGCGATGGCTTTCCTTGAGGAATCCCATCCTGGTATTTTTGAAA

ACTCGTGTATTGAAACGATGGAGGTTGTTCAGCAAACACGAGTAGACAAGCTGACACAAGGCCGACA

GACCTATGACTGGACTCTAAATAGAAACCAACCTGCTGCAACAGCATTGGCCAACACAATAGAAGTG

TTCAGATCAAATGGCCTCACGGCCAATGAGTCTGGAAGGCTCATAGACTTCCTTAAGGATGTAATGG

AGTCAATGAACAAAGAAGAAATGGGGATCACAACTCATTTTCAGAGAAAGAGACGGGTGAGAGACAA

TATGACTAAGAAAATGATAACACAGAGAACAATGGGTAAAAAGAAGCAGAGATTGAACAAAAGGAGTT

ATCTAATTAGAGCATTGACCCTGAACACAATGACCAAAGATGCTGAGAGAGGGAAGCTAAAACGGAG

AGCAATTGCAACCCCAGGGATGCAAATAAGGGGGTTTGTATACTTTGTTGAGACACTGGCAAGGAGT

ATATGTGAGAAACTTGAACAATCAGGGTTGCCAGTTGGAGGCAATGAGAAGAAAGCAAAGTTGGCAA

ATGTTGTAAGGAAGATGATGACCAATTCTCAGGACACCGAACTTTCTTTCACCATCACTGGAGATAAC

ACCAAATGGAACGAAAATCAGAATCCTCGGATGTTTTTGGCCATGATCACATATATGACCAGAAATCA

GCCCGAATGGTTCAGAAATGTTCTAAGTATTGCTCCAATAATGTTCTCAAACAAAATGGCGAGACTGG

GAAAAGGGTATATGTTTGAGAGCAAGAGTATGAAACTTAGAACTCAAATACCTGCAGAAATGCTAGCA

AGCATCGATTTGAAATATTTCAATGATTCAACAAGAAAGAAGATTGAAAAAATCCGACCGCTCTTAATA

GAGGGGACTGCATCATTGAGCCCTGGAATGATGATGGGCATGTTCAATATGTTAAGCACTGTATTAG
```

```
GCGTCTCCATCCTGAATCTTGGACAAAAGAGATACACCAAGACTACTTACTGGTGGGATGGTCTTCA
ATCCTCTGACGATTTTGCTCTGATTGTGAATGCACCCAATCATGAAGGGATTCAAGCCGGAGTCGAC
AGGTTTTATCGAACCTGTAAGCTACTTGGAATCAATATGAGCAAGAAAAAGTCTTACATAAACAGAAC
AGGTACATTTGAATTCACAAGTTTTTTCTATCGTTATGGGTTTGTTGCCAATTTCAGCATGGAGCTTCC
CAGTTTTGGGGTGTCTGGGATCAACGAGTCAGCGGACATGAGTATTGGAGTTACTGTCATCAAAAAC
AATATGATAAACAATGATCTTGGTCCAGCAACAGCTCAAATGGCCCTTCAGTTGTTCATCAAAGATTA
CAGGTACACGTACCGATGCCATATAGGTGACACACAAATACAAACCCGAAGATCATTTGAAATAAAGA
AACTGTGGGAGCAAACCCGTTCCAAAGCTGGACTGCTGGTCTCCGACGGAGGCCCAAATTTATACAA
CATTAGAAATCTCCACATTCCTGAAGTCTGCCTAAAATGGGAATTGATGGATGAGGATTACCAGGGG
CGTTTATGCAACCCACTGAACCCATTTGTCAGCCATAAAGAAATTGAATCAATGAACAATGCAGTGAT
GATGCCAGCACATGGTCCAGCCAAAAACATGGAGTATGATGCTGTTGCAACAACACACTCCTGGATC
CCCAAAAGAAATCGATCCATCTTGAATACAAGTCAAAGAGGAGTACTTGAGGATGAACAAATGTACCA
AAGGTGCTGCAATTTATTTGAAAAATTCTTCCCCAGCAGTTCATACAGAAGACCAGTCGGGATATCCA
GTATGGTGGAGGCTATGGTTTCCAGAGCCCGAATTGATGCACGGATTGATTTCGAATCTGGAAGGAT
AAAGAAAGAAGAGTTCACTGAGATCATGAAGATCTGTTCCACCATTGAAGAGCTCAGACGGCAAAAA
TAGTGAATTTAGCTTGTCCTTCATGAAAAAATGCCTTGTTTCTACT
```

PB2
(SEQ ID NO: 32)
```
AGCGAAAGCA GGTCAATTAT ATTCAATATG GAAAGAATAA AAGAACTACG AAATCTAATG
TCGCAGTCTC GCACCCGCGA GATACTCACA AAAACCACCG TGGACCATAT GGCCATAATC
AAGAAGTACA CATCAGGAAG ACAGGAGAAG AACCCAGCAC TTAGGATGAA ATGGATGATG
GCAATGAAAT ATCCAATTAC AGCAGACAAG AGGATAACGG AAATGATTCC TGAGAGAAAT
GAGCAAGGAC AAACTTTATG GAGTAAAATG AATGATGCCG GATCAGACCG AGTGATGGTA
TCACCTCTGG CTGTGACATG GTGGAATAGG AATGGACCAA TAACAAATAC AGTTCATTAT
CCAAAAATCT ACAAAACTTA TTTTGAAAGA GTCGAAAGGC TAAAGCATGG AACCTTTGGC
CCTGTCCATT TTAGAAACCA AGTCAAAATA CGTCGGAGAG TTGACATAAA TCCTGGTCAT
GCAGATCTCA GTGCCAAGGA GGCACAGGAT GTAATCATGG AAGTTGTTTT CCCTAACGAA
GTGGGAGCCA GGATACTAAC ATCGGAATCG CAACTAACGA TAACCAAAGA AGAGAAAGAA
GAACTCCAGG ATTGCAAAAT TTCTCCTTTG ATGGTTGCAT ACATGTTGGA GAGAGAACTG
GTCCGCAAAA CGAGATTCCT CCCAGTGGCT GGTGGAACAA GCAGTGTGTA CATTGAAGTG
TTGCATTTGA CTCAAGGAAC ATGCTGGGAA CAGATGTATA CTCCAGGAGG GGAAGTGAGG
AATGATGATG TTGATCAAAG CTTGATTATT GCTGCTAGGA ACATAGTGAG AAGAGCTGCA
GTATCAGCAG ATCCACTAGC ATCTTTATTG GAGATGTGCC ACAGCACACA GATTGGTGGA
ATTAGGATGG TAGACATCCT TAGGCAGAAC CCAACAGAAG AGCAAGCCGT GGATATATGC
AAGGCTGCAA TGGGACTGAG AATTAGCTCA TCCTTCAGTT TTGGTGGATT CACATTTAAG
AGAACAAGCG GATCATCAGT CAAGAGAGAG GAAGAGGTGC TTACGGGCAA TCTTCAAACA
TTGAAGATAA GAGTGCATGA GGGATATGAA GAGTTCACAA TGGTTGGGAG AAGAGCAACA
GCCATACTCA GAAAAGCAAC CAGGAGATTG ATTCAGCTGA TAGTGAGTGG GAGAGACGAA
CAGTCGATTG CCGAAGCAAT AATTGTGGCC ATGGTATTTT CACAAGAGGA TTGTATGATA
AAAGCAGTCA GAGGTGATCT GAATTTCGTC AATAGGGCGA ATCAACGATT GAATCCTATG
CATCAACTTT TAAGACATTT TCAGAAGGAT GCGAAAGTGC TTTTTCAAAA TTGGGGAGTT
```

-continued

GAACCTATCG ACAATGTGAT GGGAATGATT GGGATATTGC CCGACATGAC TCCAAGCATC

GAGATGTCAA TGAGAGGAGT GAGAATCAGC AAAATGGGTG TAGATGAGTA CTCCAGCACG

GAGAGGGTAG TGGTGAGCAT TGACCGTTTT TTGAGAATCC GGGACCAACG AGGAAATGTA

CTACTGTCTC CCGAGGAGGT CAGTGAAACA CAGGGAACAG AGAAACTGAC AATAACTTAC

TCATCGTCAA TGATGTGGGA GATTAATGGT CCTGAATCAG TGTTGGTCAA TACCTATCAA

TGGATCATCA GAAACTGGGA AACTGTTAAA ATTCAGTGGT CCCAGAACCC TACAATGCTA

TACAATAAAA TGGAATTTGA ACCATTTCAG TCTTTAGTAC CTAAGGCCAT TAGAGGCCAA

TACAGTGGGT TTGTAAGAAC TCTGTTCCAA CAAATGAGGG ATGTGCTTGG GACATTTGAT

ACCGCACAGA TAATAAAACT TCTTCCCTTC GCAGCCGCTC CACCAAAGCA AAGTAGAATG

CAGTTCTCCT CATTTACTGT GAATGTGAGG GGATCAGGAA TGAGAATACT TGTAAGGGGC

AATTCTCCTG TATTCAACTA TAACAAGGCC ACGAAGAGAC TCACAGTTCT CGGAAAGGAT

GCTGGCACTT TAACTGAAGA CCCAGATGAA GGCACAGCTG GAGTGGAGTC CGCTGTTCTG

AGGGGATTCC TCATTCTGGG CAAAGAAGAC AAGAGATATG GCCAGCACT AAGCATCAAT

GAACTGAGCA ACCTTGCGAA AGGAGAGAAG GCTAATGTGC TAATTGGGCA AGGAGACGTG

GTGTTGGTAA TGAAACGGAA ACGGGACTCT AGCATACTTA CTGACAGCCA GACAGCGACC

AAAAGAATTC GGATGGCCAT CAATTAGTGT CGAATAGTTT AAAAACGACC TTGTTTCTAC T

NP
(SEQ ID NO: 33)
AGCAAAAGCA GGGTAGATAA TCACTCACTG AGTGACATCA AAATCATGGC GTCTCAAGGC

ACCAAACGAT CTTACGAACA GATGGAGACT GATGGAGAAC GCCAGAATGC CACTGAAATC

AGAGCATCCG TCGGAAAAAT GATTGGTGGA ATTGGACGAT TCTACATCCA AATGTGCACC

GAACTCAAAC TCAGTGATTA TGAGGGACGG TTGATCCAAA ACAGCTTAAC AATAGAGAGA

ATGGTGCTCT CTGCTTTTGA CGAAAGGAGA AATAAATACC TTGAAGAACA TCCCAGTGCG

GGGAAAGATC CTAAGAAAAC TGGAGGACCT ATATACAGGA GAGTAAACGG AAAGTGGATG

AGAGAACTCA TCCTTTATGA CAAAGAAGAA ATAAGGCGAA TCTGGCGCCA AGCTAATAAT

GGTGACGATG CAACGGCTGG TCTGACTCAC ATGATGATCT GGCATTCCAA TTTGAATGAT

GCAACTTATC AGAGGACAAG AGCTCTTGTT CGCACCGGAA TGGATCCCAG GATGTGCTCT

CTGATGCAAG GTTCAACTCT CCCTAGGAGG TCTGGAGCCG CAGGTGCTGC AGTCAAAGGA

GTTGGAACAA TGGTGATGGA ATTGGTCAGA ATGATCAAAC GTGGGATCAA TGATCGGAAC

TTCTGGAGGG GTGAGAATGG ACGAAAAACA AGAATTGCTT ATGAAAGAAT GTGCAACATT

CTCAAAGGGA AATTTCAAAC TGCTGCACAA AAAGCAATGA TGGATCAAGT GAGAGAGAGC

CGGAACCCAG GGAATGCTGA GTTCGAAGAT CTCACTTTTC TAGCACGGTC TGCACTCATA

TTGAGAGGGT CGGTTGCTCA CAAGTCCTGC CTGCCTGCCT GTGTGTATGG ACCTGCCGTA

GCCAGTGGGT ACGACTTTGA AAGGGAGGGA TACTCTCTAG TCGGAATAGA CCCTTTCAGA

CTGCTTCAAA ACAGCCAAGT GTACAGCCTA ATCAGACCAA ATGAGAATCC AGCACACAAG

AGTCAACTGG TGTGGATGGC ATGCCATTCT GCCGCATTTG AAGATCTAAG AGTATTAAGC

TTCATCAAAG GGACGAAGGT GCTCCCAAGA GGGAAGCTTT CCACTAGAGG AGTTCAAATT

GCTTCCAATG AAAATATGGA GACTATGGAA TCAAGTACAC TTGAACTGAG AAGCAGGTAC

TGGGCCATAA GGACCAGAAG TGGAGGAAAC ACCAATCAAC AGAGGGCATC TGCGGGCCAA

ATCAGCATAC AACCTACGTT CTCAGTACAG AGAAATCTCC CTTTTGACAG AACAACCATT

ATGGCAGCAT TCAATGGGAA TACAGAGGGG AGAACATCTG ACATGAGGAC CGAAATCATA

AGGATGATGG AAAGTGCAAG ACCAGAAGAT GTGTCTTTCC AGGGGGGGGG AGTCTTCGAG

-continued

```
CTCTCGGACG AAAAGGCAGC GAGCCCGATC GTGCCTTCCT TTGACATGAG TAATGAAGGA

TCTTATTTCT TCGGAGACAA TGCAGAGGAG TACGACAATT AAAGAAAAAT ACCCTTGTTT CTACT
```

M (SEQ ID NO: 34)
```
AGCAAAAGCA GGTAGATATT GAAAGATGAG TCTTCTAACC GAGGTCGAAA CGTACGTACT

CTCTATCATC CCGTCAGGCC CCCTCAAAGC CGAGATCGCA CAGAGACTTG AAGATGTCTT

TGCAGGGAAG AACACCGATC TTGAGGTTCT CATGGAATGG CTAAAGACAA GACCAATCCT

GTCACCTCTG ACTAAGGGGA TTTTAGGATT TGTGTTCACG CTCACCGTGC CCAGTGAGCG

AGGACTGCAG CGTAGACGCT TTGTCCAAAA TGCCCTTAAT GGGAACGGGG ATCCAAATAA

CATGGACAAA GCAGTTAAAC TGTATAGGAA GCTCAAGAGG GAGATAACAT TCCATGGGGC

CAAAGAAATC TCACTCAGTT ATTCTGCTGG TGCACTTGCC AGTTGTATGG GCCTCATATA

CAACAGGATG GGGGCTGTGA CCACTGAAGT GGCATTTGGC CTGGTATGTG CAACCTGTGA

ACAGATTGCT GACTCCCAGC ATCGGTCTCA TAGGCAAATG GTGACAACAA CCAATCCACT

AATCAGACAT GAGAACAGAA TGGTTTTAGC CAGCACTACA GCTAAGGCTA TGGAGCAAAT

GGCTGGATCG AGTGAGCAAG CAGCAGAGGC CATGGAGGTT GCTAGTCAGG CTAGACAAAT

GGTGCAAGCG ATGAGAACCA TTGGGACTCA TCCTAGCTCC AGTGCTGGTC TGAAAAATGA

TCTTCTTGAA AATTTGCAGG CCTATCAGAA ACGAATGGGG GTGCAGATGC AACGGTTCAA

GTGATCCTCT CACTATTGCC GCAAATATCA TTGGGATCTT GCACTTGACA TTGTGGATTC

TTGATCGTCT TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA CAGCAGAGTG

CTGTGGATGC TGACGATGGT CATTTTGTCA GCATAGAGCT GGAGTAAAAA ACTACCTTGT

TTCTAC
```

NS (SEQ ID NO: 35)
```
AGCAAAAGCA GGGTGACAAA AACATAATGG ATCCAAACAC TGTGTCAAGC TTTCAGGTAG

ATTGCTTTCT TTGGCATGTC CGCAAACGAG TTGCAGACCA AGAACTAGGC GATGCCCCAT

TCCTTGATCG GCTTCGCCGA GATCAGAAAT CCCTAAGAGG AAGGGGCAGT ACTCTCGGTC

TGGACATCAA GACAGCCACA CGTGCTGGAA AGCAGATAGT GGAGCGGATT CTGAAAGAAG

AATCCGATGA GGCACTTAAA ATGACCATGG CCTCTGTACC TGCGTCGCGT TACCTAACTG

ACATGACTCT TGAGGAAATG TCAAGGGACT GGTCCATGCT CATACCCAAG CAGAAAGTGG

CAGGCCCTCT TTGTATCAGA ATGGACCAGG CGATCATGGA TAAGAACATC ATACTGAAAG

CGAACTTCAG TGTGATTTTT GACCGGCTGG AGACTCTAAT ATTGCTAAGG GCTTTCACCG

AAGAGGGAGC AATTGTTGGC GAAATTTCAC CATTGCCTTC TCTTCCAGGA CATACTGCTG

AGGATGTCAA AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG AATGGGAGAC

CTCCACTCAC TCCAAAACAG AAACGAGAAA TGGCGGGAAC AATTAGGTCA GAAGTTTGAA

GAAATAAGAT GGTTGATTGA AGAAGTGAGA CACAAACTGA AGATAACAGA GAATAGTTTT

GAGCAAATAA CATTTATGCA AGCCTTACAT CTATTGCTTG AAGTGGAGCA AGAGATAAGA

ACTTTCTCGT TCAGCTTAT TTAGTACTAA AAACACCCT TGTTTCTACT.
```

Sequences for the internal segments of another master strain (Cambridge) are shown below:

(SEQ ID NO: 38)
```
agcgaaagca ggtcaattat attcaatatg gaaagaataa agaactaag aaatctaatg tcgcagtctc gcacccgcga gatactcaca aaaaccaccg tggaccatat ggccataatc
```

-continued

```
aagaagtaca catcaggaag acaggagaag aacccagcac ttaggatgaa atggatgatg gcaatgaaat atccaattac agcagacaag aggataacgg aaatgattcc tgagagaaat gagcaaggac aaactttatg gagtaaaatg aatgatgccg gatcagaccg agtgatggta tcacctctgg ctgtgacatg gtggaatagg aatggaccaa tgacaaatac agttcattat ccaaaaatct acaaaactta ttttgaaaga gtcgaaaggc taaagcatgg aacctttggc cctgtccatt ttagaaacca agtcaaaata cgtcggagag ttgacataaa tcctggtcat gcagatctca gtgccaagga ggcacaggat gtaatcatgg aagttgtttt ccctaacgaa gtgggagcca ggatactaac atcggaatcg caactaacga taaccaaaga gaagaaagaa gaactccagg attgcaaaat ttctcctttg atggttgcat acatgttgga gagagaactg gtccgcaaaa cgagattcct cccagtggct ggtggaacaa gcagtgtgta cattgaagtg ttgcatttga ctcaaggaac atgctgggaa cagatgtata ctccaggagg ggaagtgaag aatgatgatg ttgatcaaag cttgattatt gctgctagga acatagtgag aagagctgca gtatcagcag acccactagc atctttattg gagatgtgcc acagcacaca gattggtgga attaggatgg tagacatcct taagcagaac ccaacagaag agcaagccgt ggatatatgc aaggctgcaa tgggactgag aattagctca tccttcagtt ttggtggatt cacatttaag agaacaagcg gatcatcagt caagagagag gaagaggtgc ttacgggcaa tcttcaaaca ttgaagataa gagtgcatga gggatctgaa gagttcacaa tggttgggag aagagcaaca gccatactca gaaaagcaac caggagattg attcagctga tagtgagtgg gagagacgaa cagtcgattg ccgaagcaat aattgtggcc atggtatttt cacaagagga ttgtatgata aaagcagtta gaggtgatct gaatttcgtc aatagggcga atcagcgact gaatcctatg catcaacttt taagacattt tcagaaggat gcgaaagtgc ttttcaaaa ttggggagtt gaacctatcg acaatgtgat gggaatgatt gggatattgc ccgacatgac tccaagcatc gagatgtcaa tgagaggagt gagaatcagc aaaatgggtg tagatgagta ctccagcacg gagagggtag tggtgagcat tgaccggttc ttgagagtca gggaccaacg aggaaatgta ctactgtctc ccgaggaggt cagtgaaaca cagggaacag agaaactgac aataacttac tcatcgtcaa tgatgtggga gattaatggt cctgaatcag tgttggtcaa tacctatcaa tggatcatca gaaactggga aactgttaaa attcagtggt cccagaaccc tacaatgcta tacaataaaa tggaattga accatttcag tctttagtac ctaaggccat tagaggccaa tacagtgggt ttgtaagaac tctgttccaa caaatgaggg atgtgcttgg acatttgat accgcacaga taataaaact tcttcccttc gcagccgctc caccaaagca agtagaatg cagttctcct catttactgt gaatgtgagg ggatcaggaa tgagaatact tgtaaggggc aattctcctg tattcaacta caacaaggcc acgaagagac tcacagttct cggaaaggat gctggcactt taaccgaaga cccagatgaa ggcacagctg gagtggagtc cgctgttctg aggggattcc tcattctggg caaagaagac aggagatatg ggccagcatt aagcatcaat gaactgagca accttgcgaa aggagagaag gctaatgtgc taattgggca aggagacgtg gtgttggtaa tgaaacgaaa acgggactct agcatactta ctgacagcca gacagcgacc aaaagaattc ggatggccat caattagtgt cgaatagttt aaaaacgacc ttgtttctac t
```

(SEQ ID NO: 39)
```
agcgaaagca ggcaaaccat ttgaatggat gtcaatccga ccttactttt cttaaaagtg ccagcacaaa atgctataag cacaactttc ccttataccg gagaccctcc ttacagccat
```

-continued

```
gggacaggaa caggatacac catggatact gtcaacagga cacatcagta ctcagaaaag ggaagatgga caacaaacac cgaaactgga gcaccgcaac tcaacccgat tgatgggcca ctgccagaag acaatgaacc aagtggttat gcccaaacag attgtgtatt ggaagcaatg gctttccttg aggaatccca tcctggtatt tttgaaaact cgtgtattga acgatggag gttgttcagc aaacacgagt agacaagctg acacaaggcc gacagaccta tgactggact ttaaatagaa accagcctgc tgcaacagca ttggccaaca caatagaagt gttcagatca aatggcctca cggccaatga gtcaggaagg ctcatagact tccttaagga tgtaatggag tcaatgaaaa aagaagaaat ggggatcaca actcattttc agagaaagag acgggtgaga gacaatatga ctaagaaaat gataacacag agaacaatag gtaaaaggaa acagagattg aacaaaaggg gttatctaat tagagcattg accctgaaca caatgaccaa agatgctgag agagggaagc taaaacggag agcaattgca accccaggga tgcaaataag ggggtttgta tactttgttg agacactggc aaggagtata tgtgagaaac ttgaacaatc agggttgcca gttggaggca atgagaagaa agcaaagttg gcaaatgttg taaggaagat gatgaccaat tctcaggaca ccgaactttc tttcaccatc actggagata caccaaatg gaacgaaaat cagaatcctc ggatgttttt ggccatgatc acatatatga ccagaaatca gcccgaatgg ttcagaaatg ttctaagtat tgctccaata atgttctcaa acaaaatggc gagactggga aaagggtata tgtttgagag caagagtatg aaacttagaa ctcaaatacc tgcagaaatg ctagcaagca ttgatttgaa atatttcaat gattcaacaa gaaagaagat tgaaaaaatc cgaccgctct taatagaggg gactgcatca ttgagccctg gaatgatgat gggcatgttc aatatgttaa gcactgtatt aggcgtctcc atcctgaatc ttggacaaaa gagatacacc aagactactt actggtggga tggtcttcaa tcctctgacg attttgctct gattgtgaat gcacccaatc atgaagggat tcaagccgga gtcgacaggt tttatcgaac ctgtaagcta cttggaatca atatgagcaa gaaaaagtct tacataaaca gaacaggtac atttgaattc acaagttttt tctatcgtta tgggtttgtt gccaatttca gcatggagct tcccagtttt ggggtgtctg ggatcaacga gtcagcggac atgagtattg gagttactgt catcaaaaac aatatgataa acaatgatct tggtccagca acagctcaaa tggcccttca gttgttcatc aaagattaca ggtacacgta ccgatgccat agaggtgaca cacaaataca aacccgaaga tcatttgaaa taaagaaact gtgggagcaa acccgttcca aagctggact gctggtctcc gacgaggcc caaatttata caacattaga aatctccaca ttcctgaagt ctgcctaaaa tgggaattga tggatgagga ttaccagggg cgtttatgca acccactgaa cccatttgtc agccataaag aaattgaatc aatgaacaat gcagtgatga tgccagcaca tggtccagcc aaaaacatgg agtatgatgc tgttgcaaca acacactcct ggatcccaa agaaatcga tccatcttga atacaagtca aagaggagta cttgaagatg aacaaatgta ccaaggtgc tgcaatttat ttgaaaaatt cttccccagc agttcataca aagaccagt cgggatatcc agtatggtgg aggctatggt ttccagagcc cgaattgatg cacggattga tttcgaatct ggaaggataa agaaagaaga gttcactgag atcatgaaga tctgttccac cattgaagag ctcagacggc aaaaatagtg aatttagctt gtccttcatg aaaaaatgcc ttgtttctac t
```

(SEQ ID NO: 40)
```
agcgaaagca ggtactgatt caaaatggaa gattttgtgc gacaatgctt caatccgatg attgtcgagc ttgcggaaaa aacaatgaaa gagtatgggg aggacctgaa aatcgaaaca
```

-continued

```
aacaaatttg cagcaatatg cactcacttg gaagtatgct tcatgtattc agatttccac
ttcatcaatg agcaaggcga gtcaataatc gtagaacttg gtgatcctaa tgcacttttg
aagcacagat ttgaaataat cgagggaaga gatcgcacaa tggcctggac agtagtaaac
agtatttgca acactacagg ggctgagaaa ccaaagtttc taccagattt gtatgattac
aaggaaaata gattcatcga aattggagta acaaggagag aagttcacat atactatctg
gaaaaggcca ataaaattaa atctgagaaa acacacatcc acattttctc gttcactggg
gaagaaatgg ccacaagggc cgactacact ctcgatgaag aaagcagggc taggatcaaa
accaggctat tcaccataag acaagaaatg ccagcagag gcctctggga ttcctttcgt
cagtccgaga gaggagaaga gacaattgaa gaaaggtttg aaatcacagg aacaatgcgc
aagcttgccg accaaagtct cccgccgaac ttctccagcc ttgaaaattt tagagcctat
gtggatggat tcgaaccgaa cggctacatt gagggcaagc tgtctcaaat gtccaaagaa
gtaaatgcta gaattgaacc ttttttgaaa acaacaccac gaccacttag acttccgaat
gggcctccct gttctcagcg gtccaaattc ctgctgatgg atgccttaaa attaagcatt
gaggacccaa gtcatgaagg agagggaata ccgctatatg atgcaatcaa atgcatgaga
acattctttg gatggaagga acccaatgtt gttaaaccac acgaaaaggg aataaatcca
aattatcttc tgtcatggaa gcaagtactg gcagaactgc aggacattga gaatgaggag
aaaattccaa agactaaaaa tatgaaaaaa acaagtcagc taaagtgggc acttggtgag
aacatggcac cagaaaaggt agactttgac gactgtaaag atgtaggtga tttgaagcaa
tatgatagtg atgaaccaga attgaggtcg cttgcaagtt ggattcagaa tgagttcaac
aaggcatgcg aactgacaga ttcaagctgg atagagcttg atgagattgg agaagatgtg
gctccaattg aacacattgc aagcatgaga aggaattatt tcacatcaga ggtgtctcac
tgcagagcca cagaatacat aatgaagggg gtgtacatca atactgcctt acttaatgca
tcttgtgcag caatggatga tttccaatta attccaatga taagcaagtg tagaactaag
gagggaaggc gaaagaccaa cttgtatggt tcatcataa aaggaagatc ccacttaagg
aatgacaccg acgtggtaaa cttttgtgagc atggagtttt ctctcactga cccaagactt
gaaccacaca aatgggagaa gtactgtgtt cttgagatag gagatatgct tctaagaagt
gccataggcc aggtttcaag gcccatgttc ttgtatgtga ggacaaatgg aacctcaaaa
attaaaatga atggggaat ggagatgagg cgttgtctcc tccagtcact tcaacaaatt
gagagtatga ttgaagctga gtcctctgtc aaagagaaag acatgaccaa agagttcttt
gagaacaaat cagaaacatg gcccattgga gagtctccca aaggagtgga ggaaagttcc
attgggaagg tctgcaggac tttattagca aagtcggtat ttaacagctt gtatgcatct
ccacaactag aaggattttc agctgaatca agaaaactgc ttcttatcgt tcaggctctt
agggacaatc tggaacctgg gacctttgat cttggggggc tatatgaagc aattgaggag
tgcctaatta atgatccctg ggttttgctt aatgcttctt ggttcaactc cttccttaca
catgcattga gttagttgtg gcagtgctac tatttgctat ccatactgtc caaaaagta
ccttgtttct act
```
(SEQ ID NO: 41)
```
agcaaaagca gggtagataa tcactcactg agtgacatca aaatcatggc gtcccaaggc
accaaacggt cttacgaaca gatggagact gatggagaac gccagaatgc cactgaaatc
agagcatccg tcgaaaaaat gattggtgga attggacgat tctacatcca aatgtgcaca
gaacttaaac tcagtgatta tgagggacgg ttgatccaaa acagcttaac aatagagaga
```

-continued

```
atggtgctct ctgcttttga cgaaaggaga aataaatacc tggaagaaca tcccagtgcg gggaaagatc ctaagaaaac tggaggacct atatacagaa gagtaaacgg aaagtggatg agagaactca tcctttatga caaagaagaa ataaggcgaa tctggcgcca agctaataat ggtgacgatg caacggctgg tctgactcac atgatgatct ggcattccaa tttgaatgat gcaacttatc agaggacaag ggctcttgtt cgcaccggaa tggatcccag gatgtgctct ctgatgcaag gttcaactct ccctaggagg tctggagccg caggtgctgc agtcaaagga gttggaacaa tggtgatgga attggtcagg atgatcaaac gtgggatcaa tgatcggaac ttctggaggg gtgagaatgg acgaaaaaca agaattgctt atgaaagaat gtgcaacatt ctcaaaggga aatttcaaac tgctgcacaa aaagcaatga tggatcaagt gagagagagc cggaacccag ggaatgctga gttcgaagat ctcactttc tagcacggtc tgcactcata ttgagagggt cggttgctca caagtcctgc ctgcctgcct gtgtgtatgg acctgccgta gccagtgggt acgactttga agagaggga tactctctag tcggaataga cccttcaga ctgcttcaaa acagccaagt gtacagccta atcagaccaa atgagaatcc agcacacaag agtcaactgg tgtggatggc atgccattct gccgcatttg aagatctaag agtattgagc ttcatcaaag ggacgaaggt ggtcccaaga gggaagcttt ccactagagg agttcaaatt gcttccaatg aaaatatgga gactatggaa tcaagtacac ttgaactgag aagcaggtac tgggccataa ggaccagaag tggaggaaac accaatcaac agagggcatc tgcgggccaa atcagcatac aacctacgtt ctcagtacag agaaatctcc cttttgacag aacaaccgtt atggcagcat tcactgggaa tacagagggg agaaacatctg acatgaggac cgaaatcata aggatgatgg aaagtgcaag accagaagat gtgtctttcc aggggggg agtcttcgag ctctcggacg aaaaggcagc gagcccgatc gtgccttcct ttgacatgag taatgaagga tcttatttct tcggagacaa tgcagaggag tacgacaatt aaagaaaaat acccttgttt ctact
                                                             (SEQ ID NO: 42)
agcaaaagca ggtagatatt gaaagatgag tcttctaacc gaggtcgaaa cgtacgttct ctctatcatc ccgtcaggcc ccctcaaagc cgagatcgca cagagacttg aagatgtctt tgcagggaag aacaccgatc ttgaggttct catggaatgg ctaaagacaa gaccaatcct gtcacctctg actaagggga ttttaggatt tgtgttcacg ctcaccgtgc ccagtgagcg aggactgcag cgtagacgct ttgtccaaaa tgcccttaat gggaacgggg atccaaataa catggacaaa gcagttaaac tgtataggaa gctcaagagg gagataacat tccatgggc caaagaaatc tcactcagtt attctgctgg tgcacttgcc agttgtatgg gcctcatata caacaggatg ggggctgtga ccactgaagt ggcatttggc ctggtatgtg caacctgtga acagattgct gactcccagc atcggtctca taggcaaatg gtgacaacaa ccaacccact aatcagacat gagaacagaa tggttttagc cagcactaca gctaaggcta tggagcaaat ggctggatcg agtgagcaag cagcagaggc catggaggtt gctagtcagg ctaggcaaat ggtgcaagcg atgagaacca ttgggactca tcctagctcc agtgctggtc tgaaaaatga tcttcttgaa aatttgcagg cctatcagaa acgaatgggg gtgcagatgc aacggttcaa gtgatcctct cgctattgcc gcaaatatca ttgggatctt gcacttgata ttgtggattc ttgatcgtct ttttttcaaa tgcatttacc gtcgctttaa atacggactg aaaggagggc
```

-continued

```
cttctacgga aggagtgcca aagtctatga gggaagaata tcgaaaggaa cagcagagtg ctgtggatgc tgacgatggt cattttgtca gcatagagct ggagtaaaaa actaccttgt ttctact
```

(SEQ ID NO: 43)
```
agcaaaagca gggtgacaaa gacataatgg atccaaacac tgtgtcaagc tttcaggtag attgctttct ttggcatgtc cgcaaacgag ttgcagacca agaactaggt gatgccccat tccttgatcg gcttcgccga gatcagaaat ccctaagagg aaggggcagc actcttggtc tggacatcga gacagccaca cgtgctggaa agcagatagt ggagcggatt ctgaaagaag aatccgatga ggcacttaaa atgaccatgg cctctgtacc tgcgtcgcgt tacctaaccg acatgactct tgaggaaatg tcaagggaat ggtccatgct catacccaag cagaaagtgg caggccctct ttgtatcaga atggaccagg cgatcatgga taaaaacatc atactgaaag cgaacttcag tgtgattttt gaccggctgg agactctaat attgctaagg gctttcaccg aagagggagc aattgttggc gaaatttcac cattgccttc tcttccagga catactgctg aggatgtcaa aaatgcagtt ggagtcctca tcggaggact tgaatggaat gataacacag ttcgagtctc tgaaactcta cagagattcg cttggagaag cagtaatgag aatgggagac ctccactcac tccaaaacag aaacgagaaa tggcgggaac aattaggtca gaagtttgaa gaaataagat ggttgattga agaagtgaga cacaaactga aggtaacaga gaatagtttt gagcaaataa catttatgca agccttacat ctattgcttg aagtggagca agagataaga actttctcat ttcagcttat ttaataataa aaaacaccct tgtttctact
```

Exemplary Embodiments

In one embodiment, an isolated recombinant influenza virus comprising a neuraminidase (NA) viral segment encoding a NA monomer that forms virions having stabilized NA tetramers is provided. In one embodiment, the recombinant influenza virus has a modified NA stalk that results in stabilized tetramers relative to an influenza virus having a NA with an unmodified NA stalk. In one embodiment, the modified NA stalk has a deletion. In one embodiment, the modified NA stalk has an insertion. In one embodiment, the modified NA stalk has at least one amino acid substitution relative to the unmodified stalk. In one embodiment, the modified stalk has two or more of: a deletion, an insertion, or at least one amino acid substitution. In one embodiment, the at least one substitution in the modified NA stalk is a cysteine substitution. In one embodiment, the modified NA stalk has at least two substitutions. In one embodiment, the NA has a cysteine at position 48 relative to the numbering of N1. In one embodiment, the NA has a cysteine at position 50 relative to the numbering of N1. In one embodiment, the NA has a cysteine at position 48 and position 50 relative to the numbering of N1. In one embodiment, the NA stalk is modified within residues 1 to 10 from the C-terminus of the transmembrane domain. In one embodiment, the NA stalk is modified within residues 10 to 20 from the C-terminus of the transmembrane domain. In one embodiment, the NA stalk is modified within residues 20 to 30 from the C-terminus of the transmembrane domain. In one embodiment, the NA stalk is modified within residues 30 to 50 from the C-terminus of the transmembrane domain.

For example, the recombinant influenza virus may have a N1 NA, and that N2 may have one or two cysteines in the stalk region, e.g., spaced apart with at least one residue in between, e.g., the stalk may have the following sequence:

(SEQ ID NO: 51)
SIQIGNQSQIETCNQSVITYENNTWVNQTYVNISNTNFAAGQSVVSVKL
AGNSS, which could be modified to, for example, (SEQ ID NO: 52)
IQIGNQSQIECCNQSVITYENNTWVNQTYVNISNTNFAAGQSVVSVKLA
GNSS, (SEQ ID NO: 53)
IQIGNQSQIETCCQSVITYENNTWVNQTYVNISNTNFAAGQSVVSVKLA
GNSS, (SEQ ID NO: 54)
IQIGNQSQIECCCQSVITYENNTWVNQTYVNISNTNFAAGQSVVSVKLA
GNSS, (SEQ ID NO: 55)
IQIGNQSQICTCNQSVITYENNTWVNQTYVNISNTNFAAGQSVVSVKLA
GNSS,
or (SEQ ID NO: 56)
IQIGNQSQIETCNCSVITYENNTWVNQTYVNISNTNFAAGQSVVSVKLA
GNSS.

In one embodiment, a vaccine comprising an effective amount of the recombinant influenza virus or a portion thereof is provided. In one embodiment, the vaccine is a whole virus vaccine. In one embodiment, the vaccine is a split virus vaccine. In one embodiment, the vaccine is a subunit vaccine. In one embodiment, the vaccine further comprises an adjuvant. In one embodiment, the vaccine further comprises a pharmaceutically acceptable carrier. In one embodiment, the carrier is suitable for intranasal or intramuscular administration. In one embodiment, the vaccine further comprises at least one other influenza virus isolate. In one embodiment, the vaccine further comprises at least one other microbe or microbial antigen, e.g., a non-influenza virus, a bacterial or fungal antigen.

In one embodiment, a method of preparing influenza virus having stabilized NA tetramers is provided. The method includes contacting a cell with one or more vectors comprising nucleic acid for an influenza virus NA segment encoding a NA monomer that forms virions having stabilized NA tetramers, nucleic acid for an influenza virus PA segment, nucleic acid for an influenza virus a PB1 segment, nucleic acid for an influenza virus PB2 segment, nucleic acid for an influenza virus NP segment, nucleic acid for an influenza virus NS segment, nucleic acid for an influenza virus M segment, and nucleic acid for an influenza virus HA segment, in an amount effective to produce influenza virus having stabilized NA tetramers. In one embodiment, the NA is N1, N2, N3 or N5. In one embodiment, the cell is a mammalian cell. In one embodiment, the cell is a 293T, PER.C6®, MDCK, MvLu1, CHO or Vero cell, or a cell in an avian egg.

In one embodiment, a method of making an influenza vaccine is provided comprising: providing the recombinant virus; and combining the virus with an adjuvant or treating the virus with an agent that inactivates the virus. In one embodiment, the method includes aliquoting a dose of the virus into a receptacle. In one embodiment, the adjuvant comprises immunostimulatory DNA sequences, bacterium-derived components, aluminum salt (alum) or squalene oil-in-water emulsion systems such as MF59 and AS03. In one embodiment, wherein the agent chemically inactivates the virus. In one embodiment, the agent comprises formalin or beta-propiolactone. In one embodiment, the agent comprises a detergent. In one embodiment, the detergent is a non-ionic detergent. In one embodiment, the detergent is a cationic detergent. In one embodiment, the detergent is an anionic detergent. In one embodiment, the detergent comprises CTAB, ammonium deoxycholate, Triton, SDS, Neodol 23-6, or sodium desoxycholate. In one embodiment, the agent comprises ether. In one embodiment, the method further comprises separating HA and NA from other viral components.

In one embodiment, a method of preparing influenza virus is provided comprising: contacting cells with the recombinant virus in an amount effective to yield progeny virus. In one embodiment, the virus is contacted with an avian egg. In one embodiment, the cells are mammalian cells. In one embodiment, the HA of the virus is H1, H3, H5 or H7.

Further provided is a method of preparing stabilized NA tetramers. The method includes contacting a cell with one or more vectors comprising nucleic acid for an influenza virus NA segment encoding a NA monomer that forms virions having stabilized NA tetramers and nucleic acid for an influenza virus HA. In one embodiment, the method further comprises isolating NA and HA from the cell. In one embodiment, the cell is an insect cell. In one embodiment, the cell is a CHO, MDCK, Vero, or EB66 cell.

Also provided is isolated virus prepared by the above-described methods.

In one embodiment, a method of immunizing an avian or a mammal is provided comprising: administering to the avian or the mammal a composition having an effective amount of the above-described virus. In one embodiment, the composition comprises at least one other different influenza virus. In one embodiment, the mammal is a human. In one embodiment, the composition is administered intranasally or via injection.

Further provided is a method comprising passaging the virus in eggs.

The invention will be described by the following non-limiting examples.

Example I

Neuraminidase (NA) is one of the major transmembrane glycoproteins of influenza viruses. It has been suggested that antibodies against NA play important roles in preventing influenza virus infection. However, the current influenza vaccines, which are made by inactivating egg-grown influenza viruses and purifying virus antigen, do not efficiently elicit the production of anti-NA antibodies. One possible reason for the low production of anti-NA antibodies is the structural instability of the NA protein, which functions as a homo-tetramer; the NA tetramer is apparently disrupted during the antigen purification process. Therefore, the amount of NA contained in vaccines is insufficient to elicit the production of anti-NA antibodies.

The establishment of a method that stabilizes the NA tetrameric structure may solve this problem. The amino acids 48C and 50C in NA have previously been introduced to NA in vitro (Silva et al., 2013); however, the effect of these amino acids on influenza virus replication or replication efficiency was unknown. As described herein, recombinant influenza viruses containing either the NA-48C or NA-50C mutation or both mutations expressed a stabilized NA tetramer and replicated efficiently.

Methods

A 6+2 reassortant influenza viruses containing the HA and NA gene segments from A/Singapore/GP1908/2015 (H1N1) pdm09 in the backbone of high-yield A/Puerto Rico/8/1934 (H1N1) was prepared using reverse genetics and propagation in hCK cells at 37° C. Mutant viruses with either the NA-T48C or NA-N50C mutation or both mutations were generated. hCK cells were infected with these viruses at a MOI (multiplicity of infection) of 1. Cells were lysed at 9 hours post-infection with or without DTT, and NA was detected by western blotting.

Results

In the presence of DTT, only the band representing the NA monomer was detected. In the absence of DTT, the band representing the WT-NA dimer was detected. For the mutant viruses, bands representing tetrameric NA-T48C, NA-N50C, and NA-T48C/N50C were detected. This result demonstrates that the ratio of tetrameric NA was increased by NA-T48C, NA-N50C, or both. Stabilization may be detected by any method, e.g., sialidase activity.

CONCLUSION

The NA-48C and NA-50C mutations, either singly or in combination, can stabilize the NA tetrameric structure. These amino acid mutations are thus helpful to establish a new vaccine strain that can elicit greater amounts of NA antibodies compared with those elicited by current vaccine strains.

REFERENCES

Avery's Drug Treatment: Principles and Practice of Clinical Pharmacology and Therapeutics, 3rd edition, ADIS Press, Ltd., Williams and Wilkins, Baltimore, MD (1987).

Aymard-Henry et al., Virology: A Practical Approach, Oxford IRL Press, Oxford, 119-150 (1985).

Bachmeyer, Intervirology, 5:260 (1975).

Berkow et al., eds., *The Merck Manual*, 16th edition, Merck & Co., Rahway, NJ (1992).
Bachmayer et al., *Postgrad. Med.*, 52:360 (1976).
Brady et al., *J. Hyg.*, 77:173 (1976).
Brady et al., *J. Hyg.*, 77:161 (1976).
Chen et al., *Cell*, 173:417 (2018).
Da Silva et al., *J. Biol. Chem.*, 288:644 (2013).
Duxbury et al., *J. Immunol.*, 101:62 (1968).
Hatta et al., *Science*, 293:1840 (2001).
Horimoto et al., *J. Virol.*, 68:3120 (1994).
Horimoto et al., *Vaccine*, 24:3669 (2006).
Keitel et al., in Textbook of Influenza, eds. Nickolson, K. G., Webster, R. G., and Hay, A. (Blackwell, Oxford), pp. 373-390 (1998).
Kuwahara et al., *Jpn. J. Infect. Dis.*, 71:234 (2018).
Laver & Webster, *Virology*, 69:511 (1976).
Neumann et al., *Adv. Virus Res.*, 53:265 (1999).
Neumann et al., *J. Gen. Virol.*, 83:2635 (2002).
Neumann et al., *J. Virol.*, 71:9690 (1997).
Neumann et al., *Proc. Natl. Acad. Sci. USA*, 96:9345 (1999).
Neumann et al., *Virology*, 287:243 (2001).
Osol (ed.), *Remington's Pharmaceutical Sciences*, Mack Publishing Co., Easton, PA 1324-1341 (1980).
Sugawara et al., *Biologicals*, 30:303 (2002).
Webby & Webster et al., *Science*, 302:1519 (2003).
Wood & Robertson, *Nat. Rev. Microbiol.*, 2:842 (2004).
World Health Organization TSR No. 673 (1982).
World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

SEQUENCE LISTING

```
Sequence total quantity: 56
SEQ ID NO: 1            moltype = AA  length = 469
FEATURE                 Location/Qualifiers
source                  1..469
                        mol_type = protein
                        organism = Influenza A
SEQUENCE: 1
MNPNQKIITI GSVSLTISTI CFFMQIAILI TTVTLHFKQY EFNSPPNNQV MLCEPTIIER   60
NITEIVYLTN TTIEKEICPK LAEYRNWSKP QCNITGFAPF SKDNSIRLSA GGDIWVTREP  120
YVSCDPDKCY QFALGQGTTL NNVHSNDIVH DRTPYRTLLM NELGVPFHLG TKQVCIAWSS  180
SSCHDGKAWL HVCVTGDDEN ATASFIYNGR LADSIVSWSK KILRTQESEC VCINGTCTVV  240
MTDGSASGKA DTKILFIEEG KIVHTSTLSG SAQHVEECSC YPRYPGVRCV CRDNWKGSNR  300
PIVDINIKDY SIVSSYVCSG LVGDTPRKND SSSSSHCLDP NNEEGGHGVK GWAFDDGNDV  360
WMGRTISEKL RSGYETFKVI EGWSNPNSKL QINRQVIVDR GNRSGYSGIF SVEGKSCINR  420
CFYVELIRGR KQETEVLWTS NSIVVFCGTS GTYGTGSWPD GADINLMPI              469

SEQ ID NO: 2            moltype = AA  length = 469
FEATURE                 Location/Qualifiers
source                  1..469
                        mol_type = protein
                        organism = Influenza A
SEQUENCE: 2
MNPNQKIITI GSVSLTISTI CFFMQIAILI TTVTLHFKQY EFNSPPNNQV MLCEPTIIER   60
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LIDSVVSWSK DILRTQESEC VCINGTCTVV  240
MTDGNATGKA DTKILFIEEG KIVHTSKLSG SAQHVEECSC YPRYPGVRCV CRDNWKGSNR  300
PIVDINIKDH SIVSSYVCSG LVGDTPRKND SSSSSHCLNP NNEEGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHI              469

SEQ ID NO: 3            moltype = AA  length = 469
FEATURE                 Location/Qualifiers
source                  1..469
                        mol_type = protein
                        organism = Influenza A
SEQUENCE: 3
MNPNQKIITI GSVSLTIATI CFLMQIAILV TTVTLHFKQY ECNSPPNNQV MLCEPTIIER   60
NITEIVYLTN TTIEKEICPK LAEYRNWSKP QCNITGFAPF SKDNSIRLSA GGDIWVTREP  120
YVSCDPDKCY QFALGQGTTL NNGHSNDTVH DRTPYRTLLM NELGVPFHLG TKQVCIAWSS  180
SSCHDGKAWL HVCVTGDDGN ATASFIYNGR LVDSIGSWSK KILRTQESEC VCINGTCTVV  240
MTDGSASGKA DTKILFIEEG KIVHTSLLSG SAQHVEECSC YPRYPGVRCV CRDNWKGSNR  300
PIVDINVKDY SIVSSYVCSG LVGDTPRKND SSSSSHCLDP NNEEGGHGVK GWAFDDGNDV  360
WMGRTISEKL RSGYETFKVI EGWSKPNSKL QINRQVIVDR GNRSGYSGIF SVEGKSCINR  420
CFYVELIRGR NQETEVLWTS NSIVVFCGTS GTYGTGSWPD GADINLMPI              469

SEQ ID NO: 4            moltype = AA  length = 468
FEATURE                 Location/Qualifiers
source                  1..468
                        mol_type = protein
                        organism = Influenza A
SEQUENCE: 4
```

```
MNPNQKIITI GVVNTTLSTI ALLIGVGNLI FNTVIHEKIG DHQTVIHPTT TTPAIPNCSD    60
TIIITYNNTVI NNITTIITEA ERLFKPPLPL CPFRGFFPPH KDNAIRLGEN KDVIVTREPY  120
VSCDNDNCWS FALAQGALLG TKHSNGTIKD RTPYRSLIQF PIGTAPVLGN YKEICIAWSS   180
SSCFDGKEWM HVCMTGNDND ASAQIIYAGR MTDSIKSWKR DILRTQESEC QCIDGTCVVA   240
VTDGPAANSA DHRVYWIREG RIVKYENVPK TKIQHLEECS CYVDIDVYCI CRDNWKGSNR   300
PWMRINNETI LETGYVCSKF HSDTPRPADP STVSCDSPSN VNGGPGVKGF GFKVGNDVWL   360
GRTMSTSGRS GFEIIKVAEG WINSPNHAKS VTQTLVSNND WSGYSGSFIV KTKACFQPCF   420
YVELIRGRPN KNDDVSWTSN SIVTFCGLDN EPGSGNWPDG SNIGFMPK              468

SEQ ID NO: 5               moltype = AA  length = 470
FEATURE                    Location/Qualifiers
source                     1..470
                           mol_type = protein
                           organism = Influenza A
SEQUENCE: 5
MNPNQKIITI GSVSIILTTI GLLLQITSLC SIWFSHYNQV TQTHEQPCSN NTTNYYNETF    60
VNVTNVQNNY TTVIEPSAPD VVHYSSGRDL CPIRGWAPLS KDNGIRIGSR GEVFVIREPF   120
ISCSISECRT FFLTQGALLN DKHSNGTVKD RSPFRTLMSC PIGVAPSPSN SRFESVAWSA   180
TACSDGPGWL TLGITGPDAT AVAVLKYNGI ITDTLKSWKG NIMRTQESEC VCQDEFCYTL   240
ITDGPSDAQA FYKILKIRKG KIVSMKDVDA TGFHFEECSC YPSGTDIECV CRDNWRGSNR   300
PWIRFNSDLD YQIGYVCSGI FGDNPRPVDG TGSCNSPVNN GKGRYGVKGF SFRYGDVWI    360
GRTKSLESRS GFEMVWDANG WVSTDKDSNG VQDIIDNDNW SGYSGSFSIR GETTGRNCTV   420
PCFWVEMIRG QPKEKTIWTS GSSIAFCGVN SDTTGWSWPD GALLPFDIDK              470

SEQ ID NO: 6               moltype = AA  length = 470
FEATURE                    Location/Qualifiers
source                     1..470
                           mol_type = protein
                           organism = Influenza A
SEQUENCE: 6
MNPNQKIICI SATGMTLSVV SLLIGIANLG LNIGLHYKMG DTPDVNIPNM NETNSTTTII    60
NNHTQNNFTN ITNIIVNKNE EGTFLNLTKP LCEVNSWHIL SKDNAIRIGE DAHILVTREP   120
YLSCDPQGCR MFALSQGTTL RGRHANGTIH DRSPFRALIS WEMGQAPSPY NVRVECIGWS   180
STSCHDGISR MSICMSGANN NASAVVWYGG RPVTEIPSWA GNILRTQESE CVCHCKGICPV 240
VMTDGPANNR AATKIIYFKE GKIQKIEELA GNTQHIEECS CYGAVGVIKC ICRDNWKGAN   300
RPVITIDPEM MTHTSKYLCS KILTDTSRPN DPTNGNCDAP ITGGSPDPGV KGFAFLDREN   360
SWLGRTISKD SRSGYEMLKV PNAETDTQSG PISHQVIVNN QNWSGYSGAF IDYWANKECF   420
NPCFYVELIR GRPKESSVLW TSNSIVALCG SKERLGSWSW HDGAEIIYFK              470

SEQ ID NO: 7               moltype = AA  length = 470
FEATURE                    Location/Qualifiers
source                     1..470
                           mol_type = protein
                           organism = Influenza A
SEQUENCE: 7
MNPNQKLFAL SGVAIALSIL NLLIGISNVG LNVSLHLKGS SDQDKNWTCT SVTQNNTTLI    60
ENTYVNNTTV IDKETGTAKP NYLMLNKSLC KVEGWVVVKA DNAIRFGESE QIIVTREPYV   120
SCDPLGCKMY ALHQGTTIRN KHSNGTIHDR TAFRGLISTP LGSPPVVSNS DFLCVGWSST   180
SCHDGIGRMT ICVQGNNDNA TATVYYDRRL TTTIKTWAGN ILRTQESECV CHNGTCVVIM   240
TDGSASSQAY TKVLYFHKGL VIKEEALKGS ARHIEECSCY GHNSKVTCVC RDNWQGANRP   300
VIEIDMNAME HTSQYLCTGV LTDTSRPSDK SMGDCNNPIT GSPGAPGVKG FGFLDSSNTW   360
LGRTISPRSR SGFEMLKIPN AETDPNSKIT ERQEIVDNNN WSGYSGSFID YWDESSECYN   420
PCFYVELIRG RPEEAKYVGW TSNSLIALCG SPISVGSGSF PDGAQIQYFS              470

SEQ ID NO: 8               moltype = AA  length = 470
FEATURE                    Location/Qualifiers
source                     1..470
                           mol_type = protein
                           organism = Influenza A
SEQUENCE: 8
MNPNQKIITV GSVSLGLVVL NILLHIVSIT TVLVLPGNG NNKNCNETVI REYNETVRIE    60
KVTQWHNTNV IEYIEKPESG HFMNNTEALC DAKGFAPFSK DNGIRIGSRG HVFVIREPFV  120
SCSPTECRTF FLTQGSLLND KHSNGTVKDR SPYRTLMSEG IQSPNVYQA RFEAVAWSAT   180
ACHDGKKWMT IGVGPDAKA VAVVHYGGIP TDVINSWAGD ILRTQESSCT CIQGECYWVM   240
TDGPANRQAQ YRAFKAKQGK IVGQTEISFN GSHIEECSCY PNEGKVECVC RDNWTGTNRP  300
VLVISPDLSY RAGYLCAGLP SDTPRGEDSQ FTGSCTSPVG NQGYGVKGFG FRQGNDVWMG  360
RTISRTSRSG FEILKVRNGW VQNSKEQIKR QVVVDNLKWS GYSGSFTLPV ELTKRNCLVP  420
CFWVEMIRGK PEEKTIWTSS SSIVMCGVDH EIADWSWHDG AILPFDIDKM             470

SEQ ID NO: 9               moltype = AA  length = 465
FEATURE                    Location/Qualifiers
source                     1..465
                           mol_type = protein
                           organism = Influenza A
SEQUENCE: 9
MNPNQKILCT SATAIIIGAI AVLIGIANLG LNIGLHLKPG CNCSHSQPET TNTSQTIINN    60
YYNETNITNI QMEERTSRNF NNLTKGLCTI NSWHIYGKDN AVRIGESSDV LVTREPYVSC   120
DPDECRFYAL SQGTTIRGKH SNGTIHDRSQ YRALISWPLS SPPTVYNSRV ECIGWSSTSC   180
HDGKSRMSIC ISGPNNNASA VVWYNRRPVT EINTWARNIL RTQESECVCH NGVCPVVFTD   240
```

```
GSATGPADTR IYYFKEGKIL KWESLTGTAK HIEECSCYGE RTGITCTCRD NWQGSNRPVI    300
QIDPVAMTHT SQYICSPVLT DNPRPNDPNI GKCNDPYPGN NNNGVKGFSY LDGANTWLGR    360
TISTASRSGY EMLKVPNALT DDRSKPIQGQ TIVLNADWSG YSGSFMDYWA EGDCYRACFY    420
VELIRGRPKE DKVWWTSNSI VSMCSSTEFL GQWNWPDGAK IEYFL                   465

SEQ ID NO: 10           moltype = AA   length = 759
FEATURE                 Location/Qualifiers
source                  1..759
                        mol_type = protein
                        organism = Influenza A
SEQUENCE: 10
MERIKELRNL MSQSRTREIL TKTTVDHMAI IKKYTSGRQE KNPALRMKWM MAMKYPITAD     60
KRITEMIPER NEQGQTLWSK MNDAGSDRVM VSPLAVTWWN RNGPMTNTVH YPKIYKTYFE    120
RVERLKHGTF GPVHFRNQVK IRRRVDINPG HADLSAKEAQ DVIMEVVFPN EVGARILTSE    180
SQLTITKEKK EELQDCKISP LMVAYMLERE LVRKTRFLPV AGGTSSVYIE VLHLTQGTCW    240
EQMYTPGGEV KNDDVDQSLI IAARNIVRRA AVSADPLASL LEMCHSTQIG GIRMVDILKQ    300
NPTEEQAVDI CKAAMGLRIS SSFSFGGFTF KRTSGSSVKR EEEVLTGNLQ TLKIRVHEGS    360
EEFTMVGRRA TAILRKATRR LIQLIVSGRD EQSIAEAIIV AMVFSQEDCM IKAVRGDLNF    420
VNRANQRLNP MHQLLRHFQK DAKVLFQNWG VEPIDNVMGM IGILPDMTPS IEMSMRGVRI    480
SKMGVDEYSS TERVVVSIDR FLRVRDQRGN VLLSPEEVSE TQGTEKLTIT YSSSMMWEIN    540
GPESVLVNTY QWIIRNWETV KIQWSQNPTM LYNKMEFEPF QSLVPKAIRG QYSGFVRTLF    600
QQMRDVLGTF DTAQIIKLLP FAAAPPKQSR MQFSSFTVNV RGSGMRILVR GNSPVFNYNK    660
ATKRLTVLGK DAGTLTEDPD EGTAGVESAV LRGFLILGKE DRRYGPALSI NELSNLAKGE    720
KANVLIGQGD VVLVMKRKRD SSILTDSQTA TKRIRMAIN                          759

SEQ ID NO: 11           moltype = AA   length = 757
FEATURE                 Location/Qualifiers
source                  1..757
                        mol_type = protein
                        organism = Influenza A
SEQUENCE: 11
MDVNPTLLFL KVPAQNAIST TFPYTGDPPY SHGTGTGYTM DTVNRTHQYS EKGRWTTNTE     60
TGAPQLNPID GPLPEDNEPS GYAQTDCVLE AMAFLEESHP GIFENSCIET MEVVQQTRVD    120
KLTQGRQTYD WTLNRNQPAA TALANTIEVF RSNGLTANES GRLIDFLKDV MESMKKEEMG    180
ITTHFQRKRR VRDNMTKKMI TQRTIGKRKQ RLNKRGYLIR ALTLNTMTKD AERGKLKRRA    240
IATPGMQIRG FVYFVETLAR SICEKLEQSG LPVGGNEKKA KLANVVRKMM TNSQDTELSF    300
TITGDNTKWN ENQNPRMFLA MITYMTRNQP EWFRNVLSIA PIMFSNKMAR LGKGYMFESK    360
SMKLRTQIPA EMLASIDLKY FNDSTRKKIE KIRPLLIEGT ASLSPGMMMG MFNMLSTVLG    420
VSILNLGQKR YTKTTYWWDG LQSSDDFALI VNAPNHEGIQ AGVDRFYRTC KLLGINMSKK    480
KSYINRTGTF EFTSFFYRYG FVANFSMELP SFGVSGINES ADMSIGVTVI KNNMINNDLG    540
PATAQMALQL FIKDYRYTYR CHRGDTQIQT RRSFEIKKLW EQTRSKAGLL VSDGGPNLYN    600
IRNLHIPEVC LKWELMDEDY QGRLCNPLNP FVSHKEIESM NNAVMMPAHG PAKNMEYDAV    660
ATTHSWIPKR NRSILNTSQR GVLEDEQMYQ RCCNLFEKFF PSSSYRRPVG ISSMVEAMVS    720
RARIDARIDF ESGRIKKEEF TEIMKICSTI EELRRQK                            757

SEQ ID NO: 12           moltype = AA   length = 716
FEATURE                 Location/Qualifiers
source                  1..716
                        mol_type = protein
                        organism = Influenza A
SEQUENCE: 12
MEDFVRQCFN PMIVELAEKT MKEYGEDLKI ETNKFAAICT HLEVCFMYSD FHFINEQGES     60
IIVELGDPNA LLKHRFEIIE GRDRTMAWTV VNSICNTTGA EKPKFLPDLY DYKENRFIEI    120
GVTRREVHIY YLEKANKIKS EKTHIHIFSF TGEEMATRAD YTLDEESRAR IKTRLFTIRQ    180
EMASRGLWDS FRQSERGEET IEERFEITGT MRKLADQSLP PNFSSLENFR AYVDGFEPNG    240
YIEGKLSQMS KEVNARIEPF LKTTPRPLRL PNGPPCSQRS KFLLMDALKL SIEDPSHEGE    300
GIPLYDAIKC MRTFFGWKEP NVVKPHEKGI NPNYLLSWKQ VLAELQDIEN EEKIPKTKNM    360
KKTSQLKWAL GENMAPEKVD FDDCKDVGDL KQYDSDEPEL RSLASWIQNE FNKACELTDS    420
SWIELDEIGE DVAPIEHIAS MRRNYFTSEV SHCRATEYIM KGVYINTALL NASCAAMDDF    480
QLIPMISKCR TKEGRRKTNL YGFIIKGRSH LRNDTDVVNF VSMEFSLTDP RLEPHKWEKY    540
CVLEIGDMLL RSAIGQVSRP MFLYVRTNGT SKIKMKWGME MRRCLLQSLQ QIESMIEAES    600
SVKEKDMTKE FFENKSETWP IGESPKGVEE SSIGKVCRTL LAKSVFNSLY ASPQLEGFSA    660
ESRKLLLIVQ ALRDNLEPGT FDLGGLYEAI EECLINDPWV LLNASWFNSF LTHALS       716

SEQ ID NO: 13           moltype = AA   length = 498
FEATURE                 Location/Qualifiers
source                  1..498
                        mol_type = protein
                        organism = Influenza A
SEQUENCE: 13
MASQGTKRSY EQMETDGERQ NATEIRASVG KMIGGIGRFY IQMCTELKLS DYEGRLIQNS     60
LTIERMVLSA FDERRNKYLE EHPSAGKDPK KTGGPIYRRV NGKWMRELIL YDKEEIRRIW    120
RQANNGDDAT AGLTHMMIWH SNLNDATYQR TRALVRTGMD PRMCSLMQGS TLPRRSGAAG    180
AAVKGVGTMV MELVRMIKRG INDRNFWRGE NGRKTRIAYE RMCNILKGKF QTAAQKAMMD    240
QVRESRNPGN AEFEDLTFLA RSALILRGSV AHKSCLPACV YGPAVASGYD FEREGYSLVG    300
IDPFRLLQNS QVYSLIRPNE NPAHKSQLVW MACHSAAFED LRVLSFIKGT KVVPRGKLST    360
RGVQIASNEN METMESSTLE LRSRYWAIRT RSGGNTNQQR ASAGQISIQP TFSVQRNLPF    420
DRTTVMAAFT GNTEGRTSDM RTEIIRMMES ARPEDVSFQG RGVFELSDEK AASPIVPSFD    480
MSNEGSYFFG DNAEEYDN                                                 498
```

```
SEQ ID NO: 14              moltype = AA  length = 252
FEATURE                    Location/Qualifiers
source                     1..252
                           mol_type = protein
                           organism = Influenza A
SEQUENCE: 14
MSLLTEVETY VLSIIPSGPL KAEIAQRLED VFAGKNTDLE VLMEWLKTRP ILSPLTKGIL     60
GPVFTLTVPS ERGLQRRRFV QNALNGNGDP NNMDKAVKLY RKLKREITFH GAKEISLSYS    120
AGALASCMGL IYNRMGAVTT EVAFGLVCAT CEQIADSQHR SHRQMVTTTN PLIRHENRMV    180
LASTTAKAME QMAGSSEQAA EAMEVASQAR QMVQAMRTIG THPSSSAGLK NDLLENLQAY    240
QKRMGVQMQR FK                                                       252

SEQ ID NO: 15              moltype = AA  length = 469
FEATURE                    Location/Qualifiers
source                     1..469
                           mol_type = protein
                           organism = Influenza A
SEQUENCE: 15
MNPNQKIITI GSVCMTIGMA NLILQIGNII SIWISHSIQL GNQNQIETCN QSVITYENNT     60
WVNQTYVNIS NTNFAAGQSV VSVKLAGNSS LCPVSGWAIY SKDNSVRIGS KGDVFVIREP    120
FISCSPLECR TFFLTQGALL NDKHSNGTIK DRSPYRTLMS CPIGEVPSPY NSRFESVAWS    180
ASACHDGINW LTIGISGPDN GAVAVLKYNG IITDTIKSWR NNILRTQESE CACVNGSCFT    240
VMTDGPSNGQ ASYKIFRIEK GKIVKSVEMN APNYHYEECS CYPDSSEITC VCRDNWHGSN    300
RPWVSFNQNL EYQIGYICSG IFGDNPRPND KTGSCGPVSS NGANGVKGFS FKYGNGVWIG    360
RTKSISSRNG FEMIWDPNGW TGTDNNFSIK QDIVGINEWS GYSGSFVQHP ELTGLDCIRP    420
CFWVELIRGR PKENTIWTSG SSISFCGVNS DTVGWSWPDG AELPFTIDK               469

SEQ ID NO: 16              moltype = AA  length = 470
FEATURE                    Location/Qualifiers
source                     1..470
                           mol_type = protein
                           organism = Influenza A
SEQUENCE: 16
MNPNQKLFAL SGVAIALSIL NLLIGISNVG LNVSLHLKGS SDQDKNWTCT SVTQNNTTLI     60
ENTYVNNTTV IDKETGTAKP NYLMLNKSLC KVEGWVVVAK DNAIRFGESE QIIVTREPYV    120
SCDPLGCKMY ALHQGTTIRN KHSNGTIHDR TAFRGLISTP LGSPPVVSNS DFLCVGWSST    180
SCHDGIGRMT ICVQGNNDNA TATVYYDRRL TTTIKTWAGN ILRTQESECV CHNGTCVVIM    240
TDGSASSQAY TKVLYFHKGL VIKEEALKGS ARHIEECSCY GHNSKVTCVC RDNWQGANRP    300
VIEIDMNAME HTSQYLCTGV LTDTSRPSDK SMGDCNNPIT GSPGAPGVKG FGFLDSSNTW    360
LGRTISPRSR SGFEMLKIPN AETDPNSKIT ERQEIVDNNN WSGYSGSFID YWDESSECYN    420
PCFYVELIRG RPEEAKYVGW TSNSLIALCG SPISVGSGSF PDGAQIQYFS               470

SEQ ID NO: 17              moltype = AA  length = 465
FEATURE                    Location/Qualifiers
source                     1..465
                           mol_type = protein
                           organism = Influenza A
SEQUENCE: 17
MNPNQKILCT SATAIIIGAI AVLIGIANLG LNIGLHLKPG CNCSHSQPET TNTSQTIINN     60
YYNETNITNI QMEERTSRNF NNLTKGLCTI NSWHIYGKDN AVRIGESSDV LVTREPYVSC    120
DPDECRFYAL SQGTTIRGKH SNGTIHDRSQ YRALISWPLS SPPTVYNSRV ECIGWSSTSC    180
HDGKSRMSIC ISGPNNNASA VVWYNRRPVA EINTWARNIL RTQESECVCH NGVCPVVFTD    240
GSATGPADTR IYYFKEGKIL KWESLTGTAK HIEECSCYGE RTGITCTCRD NWQGSNRPVI    300
QIDPVAMTHT SQYICSPVLT DNPRPNDPNI GKCNDPYPGN NNNGVKGFSY LDGANTWLGR    360
TISTASRSGY EMLKVPNALT DDRSKPIQGQ TIVLNADWSG YSGSFMDYWA EGDCYRACFY    420
VELIRGRPKE DKVWWTSNSI VSMCSSTEFL GQWNWPDGAK IEYFL                   465

SEQ ID NO: 18              moltype = AA  length = 469
FEATURE                    Location/Qualifiers
source                     1..469
                           mol_type = protein
                           organism = Influenza A
SEQUENCE: 18
MNPNQKIITI GSVSLTISTI CFFMQIAILI TTVTLHFKQY EFNSPPNNQV MLCEPTIIER     60
NITEIVYLTN TTIEKEICPK LAEYRNWSKP QCNITGFAPF SKDNSIRLSA GGDIWVTREP    120
YVSCDPDKCY QFALGQGTTL NNVHSNDIVH DRTPYRTLLM NELGVPFHLG TKQVCIAWSS    180
SSCHDGKAWL HVCVTGDDEN ATASPIYNGR LADSIVSWSK KILRTQESEC VCINGTCTVV    240
MTDGSASGKA DTKILFIEEG KIVHTSTLSG SAQHVEECSC YPRYPGVRCV CRDNWKGSNR    300
PIVDINIKDY SIVSSYVCSG LVGDTPRKND SSSSSHCLDP NNEEGGHGVK GWAFDDGNDV    360
WMGRTISEKL RSGYETFKVI EGWSNPNSKL QINRQVIVDR GNRSGYSGIF SVEGKSCINR    420
CFYVELIRGR KQETEVLWTS NSIVVFCGTS GTYGTGSWPD GADINLMPI                469

SEQ ID NO: 19              moltype = DNA  length = 1434
FEATURE                    Location/Qualifiers
source                     1..1434
                           mol_type = other DNA
                           organism = Influenza A
SEQUENCE: 19
```

-continued

```
atgaatccaa atcaaaagat aataacgatt ggctctgttt ctctcaccat ttccacaata  60
tgctttttca tgcaaattgc cattttgata actactgtaa cattgcattt caagcaatat  120
gaattcaact cccccccaaa caaccaagtg atgctgtgtg aaccaacaat aatagaaaga  180
aacataacag agatagtgta tttaaccaac accaccatag agaaggaaat atgccccaaa  240
ccagcagaat acagaaattg gtcaaaaccg caatgtggca ttacaggatt tgcacctttc  300
tctaaggaca attcgatcag gctttccgct ggtggggaca tctgggtgac aagagaacct  360
tatgtgtcat gcgatcctga caagtgttat caatttgccc ttggacaggg aacaacacta  420
aacaacgtgc attcaaataa caaagtacgt gataggaccc cttatcggac tctattgatg  480
aatgagttgg gtgttccttt ccatctgggg accaagcaag tgtgcatagc atggtccagc  540
tcaagttgtc acgatggaaa agcatggctg catgtttgta taacgggga tgataaaaat  600
gcaactgcta gcttcattta caatgggagg cttgtagata gtgttgtttc atggtccaaa  660
gatattctca ggacccagga gtcagaatgc atttgtatca atggaacttg tacagtagta  720
atgactgatg gaagtgcttc aggaaaagct gatactaaaa tactattcat tgaggagggg  780
aaaatcgttc atactagcac attgtcagga agtgctcagc atgtcgaaga gtgctcttgc  840
tatcctcgat atcctggtgt cagatgtgtc tgcagagaca actggaaggg ctccaatcgg  900
cccatcgtag atataaacat aaaggatcat agcattgttt ccagttatgt gtgttcagga  960
cttgttggag acacacccag aaaaaacgac agctccagca gtagccattg tttggatcct  1020
aacaatgaag aaggtggtca tggagtgaaa ggctgggcct ttgatgatgg aaatgacgtg  1080
tggatgggaa gaacaatcaa cgagacgtca cgcttagggt atgaaacctt caaagtcatt  1140
gaaggctggt ccaaccctaa gtccaaattg cagacaaata ggcaagtcat agttgacaga  1200
ggtgataggt ccggttattc tggtattttc tctgttgaag gcaaaagctg cataaatcgg  1260
tgcttttatg tggagttgat taggggaaga aaagaggaaa ctgaagtctt gtggacctca  1320
aacagtattg ttgtgttttg tggcacctca ggtacatatg gaacaggctc atggcctgat  1380
ggggcggacc tcaatctcat gcctatataa gctttcgcaa ttttagaaaa aact        1434

SEQ ID NO: 20          moltype = DNA  length = 1434
FEATURE                Location/Qualifiers
source                 1..1434
                       mol_type = other DNA
                       organism = Influenza A
SEQUENCE: 20
atgaatccaa atcaaaagat aataacgatt ggctctgttt ctctcaccat ttccacaata  60
tgctttttca tgcaaattgc cattttgata actactgtaa cattgcattt caagcaatat  120
gaattcaact cccccccaaa caaccaagtg atgctgtgtg aaccaacaat aatagaaaga  180
aacataacag agatagtgta tttaaccaac accaccatag agaaggaaat atgccccaaa  240
ccagcagaat acagaaattg gtcaaaaccg caatgtggca ttacaggatt tgcacctttc  300
tctaaggaca attcgatcag gctttccgct ggtggggaca tctgggtgac aagagaacct  360
tatgtgtcat gcgatcctga caagtgttat caatttgccc ttggacaggg aacaacacta  420
aacaacgtgc attcaaataa caaagtacgt gaaaggaccc cttatcggac tctattgatg  480
aatgagttgg gtgttccttt ccatctgggg accaagcaag tgtgcatagc atggtccagc  540
tcaagttgtc acgatggaaa agcatggctg catgtttgta taacgggga tgataaaaat  600
gcaactgcta gcttcattta caatgggagg cttgtagata gtgttgtttc atggtccaaa  660
gatattctca ggacccagga gtcagaatgc atttgtatca atggaacttg tacagtagta  720
atgactgatg gaagtgcttc aggaaaagct gatactaaaa tactattcat tgaggagggg  780
aaaatcgttc atactagcac attgtcagga agtgctcagc atgtcgaaga gtgctcttgc  840
tatcctcgat atcctggtgt cagatgtgtc tgcagagaca actggaaggg ctccaatcgg  900
cccatcgtag atataaacat aaaggatcat agcattgttt ccagttatgt gtgttcagga  960
cttgttggag acacacccag aaaaaacgac agctccagca gtagccattg tttggatcct  1020
aacaatgaag aaggtggtgg cggagtgaaa ggctgggcct ttgatgatgg aaatgacgtg  1080
tggatgggaa gaacaatcaa cgagaagtca cgcttagggt atgaaacctt caaagtcatt  1140
gaaggctggt ccaaccctaa gtccaaattg cagacaaata ggcaagtcat agttgacaga  1200
ggtgataggt ccggttattc tggtattttc tctgttgaag gcaaaagctg cataaatcgg  1260
tgcttttatg tggagttgat taggggaaga aaagaggaaa ctgaagtctt gtggacctca  1320
aacagtattg ttgtgttttg tggcacctca ggtacatatg gaacaggctc atggcctgat  1380
ggggcggacc tcaatctcat gcctatataa gctttcgcaa ttttagaaaa aact        1434

SEQ ID NO: 21          moltype = DNA  length = 1410
FEATURE                Location/Qualifiers
source                 1..1410
                       mol_type = other DNA
                       organism = Influenza A
SEQUENCE: 21
atgaatccaa atcaaaagat aataacgatt ggctctgttt ctctcaccat ttccacaata  60
tgcttcttca tgcaaattgc catcctgata actactgtaa cattgcattt caagcaatat  120
gaattcaact cccccccaaa caaccaagtg atgctgtgtg aaccaacaat aatagaaaga  180
aacataacag agatagtgta tttgaccaac accaccatag agaaggaaat atgccccaaa  240
ccagcagaat acagaaattg gtcaaaaccg caatgtggca ttacaggatt tgcacctttc  300
tctaaggaca attcgattag gctttccgct ggtggggaca tctgggtgac aagagaacct  360
tatgtgtcat gcgatcctga caagtgttat caatttgccc ttggacaggg aacaacacta  420
aacaacgtgc attcaaataa cacagtacgt gataggaccc cttatcggac tctattgatg  480
aatgagttgg gtgttccttt ccatctgggg accaagcaag tgtgcatagc atggtccagc  540
tcaagttgtc acgatggaaa agcatggctg catgtttgta taacgggga tgataaaaat  600
gcaactgcta gcttcattta caatgggagg cttgtagata gtgttgtttc atggtccaaa  660
gatattctca ggacccagga gtcagaatgc gtttgtatca atggaacttg tacagtagta  720
atgactgatg gaaatgctac aggaaaagct gatactaaaa tactattcat tgaggagggg  780
aaaatcgttc atactagcaa attgtcagga agtgctcagc atgtcgaaga gtgctcttgc  840
tatcctcgat atcctggtgt cagatgtgtc tgcagagaca actggaaagg atccaaccgg  900
cccatcgtag atataaacat aaaggatcat agcattgttt ccagttatgt gtgttcagga  960
cttgttggag acacacccag aaaaaacgac agctccagca gtagccattg tttgaatcct  1020
```

```
aacaatgaag aaggtggtca tggagtgaaa ggctgggcct ttgatgatgg aaatgacgtg 1080
tggatgggga gaacaatcaa cgagacgtca cgcttagggt atgaaacctt caaagtcgtt 1140
gaaggctggt ccaaccctaa gtccaaattg cagataaata ggcaagtcat agttgacaga 1200
ggtgataggc ccgttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg aacaggctc atggcctgat 1380
ggggcggacc tcaatctcat gcatatataa                                    1410

SEQ ID NO: 22           moltype = DNA  length = 1410
FEATURE                 Location/Qualifiers
source                  1..1410
                        mol_type = other DNA
                        organism = Influenza A
SEQUENCE: 22
atgaatccaa atcaaaagat aataacgatt ggctctgttt ctctcaccat ttccacaata 60
tgcttcttca tgcaaattgc catcctgata actactgtaa cattgcattt caagcaatat 120
gaattcaact ccccccaaa caaccaagtg atgctgtgtg aaccaacaat aatagaaaga 180
aacataacag agatagtgta tttgaccaac accaccatag agaaggaaat atgccccaaa 240
ccagcagaat acagaaattg gtcaaaaccg caatgtggca ttacaggatt tgcaccttc 300
tctaaggaca attcgattag gctttccgct ggtgggaca tctgggtgac aagagaacct 360
tatgtgtcat cgatcctga caagtgttat caatttgccc ttggacaggg aacaacacta 420
aacaacgtgc attcaaataa caaagtacgt gagaggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta caatgggagg cttgtagata gtgttgtttc atggtccaaa 660
gatattctca ggacccagga gtcagaatgc gtttgtatca atggaacttg tacagtagta 720
atgactgatg gaagtgctac aggaaaagct gatactaaaa tactattcat tgaggagggg 780
aaaatcgttc atactagcaa attgtcagga agtgctcagc atgtcgaaga gtgctcttgc 840
tatcctcgat atcctggtgt cagatgtgtc tgcagagaca ctggaaagg atccaaccgg 900
cccatcgtag atataaacat aaaggatcat agcattgttt ccagttatgt gtgttcagga 960
cttgttggag acacacccag aaaaacgac agctccagca gtagccattg tttgaatcct 1020
aacaatgaag aaggtgttca tggagtgaaa ggctgggcct ttgatgatgg aaatgacgtg 1080
tggatgggga gaacaatcaa cgagaagtca cgcttagggt atgaaacctt caaagtcgtt 1140
gaaggctggt ccaaccctaa gtccaaattg cagataaata ggcaagtcat agttgacaga 1200
ggtgataggc ccgttattc tggtattttc tctgttgaag gcaaaagctg catcaatcgg 1260
tgcttttatg tggagttgat taggggaaga aaagaggaaa ctgaagtctt gtggacctca 1320
aacagtattg ttgtgttttg tggcacctca ggtacatatg aacaggctc atggcctgat 1380
ggggcggacc tcaatctcat gcatatataa                                    1410

SEQ ID NO: 23           moltype = DNA  length = 1411
FEATURE                 Location/Qualifiers
source                  1..1411
                        mol_type = other DNA
                        organism = Influenza A
SEQUENCE: 23
atgaatccaa atcaaaagat aataacgatt ggctctgttt ctctcacaat ttccacaata 60
tgcttcttca tgcaaattgc catcctgata actactgtaa cattgcattt caagcaatat 120
gaattcaact ccccccaaa taaccaagtg atgctgtgtg aaccaacaat aatagaaaga 180
aacataacag agatagtgta tttgaccaac accaccatag aaggaaat atgccccaaa 240
ccagcagaat acagaaattg gtcaaaaccg caatgtggca ttacaggatt tgcacctttc 300
tctaaagaca attcgattag gctttccgct ggtgggaca tctgggtgac aagagaacct 360
tatgtgtcat cgatcttga caagtgttat caatttgccc ttggacaggg aacaacacta 420
aacaacgtgc attcaaataa cacagtacgt gataggaccc cttatcggac tctattgatg 480
aatgagttgg gtgttccttt ccatctgggg accaagcaag tgtgcatagc atggtccagc 540
tcaagttgtc acgatggaaa agcatggctg catgtttgta taacggggga tgataaaaat 600
gcaactgcta gcttcattta cawatgggag gcttgtagat agtgttgttt catggtccaa 660
cgatattctc aggacccagg agtcagaatg cgtttgtatc aatggaactt gtacagtagt 720
aatgactgat ggaaatgcta caggaaaagc tgatactaaa atactattca ttgaggaggg 780
gaaaatcgtt catactagca aattgtcagg aagtgctcag catgtcgaag agtgctcttg 840
ctatcctcga tatcctggtg tcagatgtgt ctgcagagac aactggaaag gatccaaccg 900
gcccatcata gatataaaca taaggatca tagcattgtt tccagttatg tgtgttcagg 960
acttgttgga gacacaccca gaaaaagcga cagctccagc agtagccatt gtttgaatcc 1020
taacaatgaa gaaggtggtc atggagtgaa aggctgggcc tttgatgatg gaaatgacgt 1080
gtggatgggg agaacaatca cgagacgtc acgcttaggg tatgaaacct tcaaagtcgt 1140
tgaaggctgg tccaacccta gtccaaattg cagataaat ggcaagtca tagttgacag 1200
aggtgatagg cccggttatt ctggtattt tctgttgaa ggcaaaagct gcatcaatcg 1260
gtgctttat gtggagttga tcaggggaag aaaagaggaa actgaagtct tgtggacctc 1320
aaacagtatt gttgtgtttt gtggcacctc aggtacatat ggaacaggct catggcctga 1380
tggggcggac tcaatctca tgcatatata a                                 1411

SEQ ID NO: 24           moltype = DNA  length = 1410
FEATURE                 Location/Qualifiers
source                  1..1410
                        mol_type = other DNA
                        organism = Influenza A
SEQUENCE: 24
atgaatccaa atcaaaagat aataacgatt ggctctgttt ctctcaccat ttccacaata 60
tgcttcttca tgcaaattgc catcctgata actactgtaa cattgcattt caagcaatat 120
gaattcaact ccccccaaa taaccaagtg atgctgtgtg aaccaacaat aatagaaaga 180
```

```
aacataacag agatagtgta tttgaccaac accaccatag agaaggaaat atgcccaaa   240
ccagcagaat acagaaattg gtcaaaaccg caatgtggca ttacaggatt tgcacctttc  300
tctaaggaca attcgattag gctttccgct ggtggggaca tctgggtgac aagagaacct  360
tatgtgtcat gcgatcctga caagtgttat caatttgccc ttggacaggg aacaacacta  420
aacaacgtgc attcaaataa cacagtacgt gataggaccc cttatcggac tctattgatg  480
aatgagttgg gtgttccttt ccatctgggg accaagcaag tgtgcatggc atggtccagc  540
tcaagttgtc acgatggaaa agcatggctg catgtttgta taactgggga tgataaaaat  600
gcaactgcta gcttcattta caatggggag cttgtagata gtgttgtttc atggtccaaa  660
gatattctca ggacccagga gtcagaatgc gtttgcatca atggaacttg tacagtagta  720
atgactgatg gaaatgctac aggaaaagct gatactaaaa tactattcat tgaggagggg  780
aaaatcgttc atactagcaa attgtcagga agtgctcagc atgtcgaaga gtgctcctgc  840
tatcctcgat atcctggtgt cagatgtgtc tgcagagaca actggaaagg atccaaccgg  900
cccattgtag atataaacat aaaggatcat agcattgttt ccagttatgt gtgttcagga  960
cttgttggag acacacccag aaaaagcgac agctccagca gtagccattg tttgaatcct  1020
aacaatgaag aaggtggtca tggagtgaaa ggctgggcct tgatgatgg aaatgacgtg  1080
tggatgggga gaacaatcaa cgagacgtca cgcttagggt atgaaacctt caaagtcgtt  1140
gaaggctggt ccaactctaa gtccaaattg cagataaata ggcaagtcat agttgacaga  1200
ggtgataggt ccggttattc tggtattttc tctgttgaag gcaaaagctg catcaatcgg  1260
tgcttttatg tggagttgat taggggaaga aaagaggaaa ctgaagtctt gtggacctca  1320
aacagtattg ttgtgtttttg tggcacctca ggtacatatg aacaggctc atggcctgat  1380
ggggcggacc tcaatctcat gcatatataa                                   1410

SEQ ID NO: 25           moltype = DNA   length = 1434
FEATURE                 Location/Qualifiers
source                  1..1434
                        mol_type = other DNA
                        organism = Influenza A
SEQUENCE: 25
atgaatccaa atcaaaagat aataacgatt ggctctgttt ctctcacaat ttccacaata  60
tgcttcttca tgcaaattgc catcctgata actactgtaa cattgcattt caagcaatat  120
gaattcaact ccccccaaa taccaagtg atgctgtgtg aaccaacaat aatagaaaga  180
aacataacag agatagtgta tttgaccaac accaccatag agaaggaaat atgcccaaa  240
ccagcagaat acagaaattg gtcaaaaccg caatgtggca ttacaggatt tgcacctttc  300
tctaaggaca attcgattag gctttccgct ggtggggaca tctgggtgac aagagaacct  360
tatgtgtcat gcgatcttga caagtgttat caatttgccc ttggacaggg aacaacacta  420
aacaacgtgc attcaaataa cacagtacgt gataggaccc cttatcggac tctattgatg  480
aatgagttgg gtgttccttt ccatctgggg accaagcaag tgtgcatagc atggtccagc  540
tcaagttgtc acgatggaaa agcatggctg catgtttgta taacggggga tgataaaaat  600
gcaactgcta gcttcattta caatggggag cttgtagata gtgttgtctc atggtccaaa  660
gatattctca ggacccagga gtcagaatgc gtttgtatca atggaacttg tacagtagta  720
atgactgatg gaaatgctac aggaaaagct gatactaaaa tactattcat tgaggagggg  780
aaaatcgttc atactagcaa attgtcagga agtgctcagc atgtcgaaga gtgctcttgc  840
tatcctcgat atcctggtgt cagatgtgtc tgcagagaca actggaaagg atccaaccgg  900
cccatcatag atataaacat aaaggatcat agcattgttt ccagttatgt gtgttcagga  960
cttgttggag acacacccag aaaaagcgac agctccagca gtagccattg tttgaatcct  1020
aacaatgaag aaggtggtca tggagtgaaa ggctgggcct tgatgatgg aaatgacgtg  1080
tggatgggga gaacaatcaa cgagacgtca cgcttagggt atgaaacctt caaagtcgtt  1140
gaaggctggt ccaaccctaa gtccaaattg cagataaata ggcaagtctt agttgacaga  1200
ggtgataggt ccggttattc tggtattttc tctgttgaag gcaaaagctg catcaatcgg  1260
tgcttttatg tggagttgat taggggaaga aaagaggaaa ctgaagtctt gtggacctca  1320
aacagtattg ttgtgtttttg tggcacctca ggtacatatg aacaggctc atggcctgat  1380
ggggcggacc tcaatctcat gcatatataa gctttcgcaa ttttagaaaa aact         1434

SEQ ID NO: 26           moltype = DNA   length = 1448
FEATURE                 Location/Qualifiers
source                  1..1448
                        mol_type = other DNA
                        organism = Influenza A
SEQUENCE: 26
atgaatccaa atcaaaagat aataacgatt ggctctgttt ctctcacaat tccacaata   60
tgcttcttca tgcaaattgc catcctgata actactgtaa cattgcatttt caagcaatat  120
gaattcaact ccccccaaa taccaagtg atgctgtgtg aaccaacaat aatagaaga   180
aacataacag agatagtgta tttgaccaac accaccatag agaaggaaat atgcccaaa   240
ccagcagaat acagaaattg gtcaaaaccg caatgtggca ttacaggatt tgcacctttc  300
tctaaggaca attcgattag gctttccgct ggtggggaca tctgggtgac aagagaacct  360
tatgtgtcat gcgatcttga caagtgttat caatttgccc ttggacaggg aacaacacta  420
aacaacgtgc attcaaataa cacagtacgt gataggaccc cttatcggac tctattgatg  480
aatgagttgg gtgttccttt ccatctgggg accaagcaag tgtgcatagc atggtccagc  540
tcaagttgtc acgatggaaa agcatggctg catgtttgta taacggggga tgataaaaat  600
gcaactgcta gcttcattta caatggggag cttgtagata gtgttgtttc atggtccaac  660
gatattctca ggacccagga gtcagaatgc gtttgtatca atggaacttg tacagtagta  720
atgactgatg gaaatgctac aggaaaggct gacactaaaa tactattcat tgaggagggg  780
aaaatcgtac atactagcaa attgtcagga agtgctcagc atgtcgaaga gtgctcttgc  840
tatcctcgat atcctggtgt cagatgtgtc tgcagagaca actggaaagg atccaaccgg  900
cccatcatag atataaacat aaaggatcat agcattgttt ccagttatgt gtgttcagga  960
cttgttggag acacacccag aaaaagcgac agctccagca gtagccattg tttgaacctt  1020
aacaatgaag aaggtggtca tggagtgaaa ggctgggcct tgatgatgg aaatgacgtg  1080
tggatgggga gaacaatcaa cgagacgtca cgcttagggt atgaaacctt caaagtcgtt  1140
gaaggctggt ccaaccctaa gtccaaattg cagataaata ggcaagtcat agttgacaga  1200
```

```
ggtgataggt ccggttattc tggtattttc tctgttgaag gcaaaagctg catcaatcgg   1260
tgcttttatg trgagttgat taggggaaga aaagaggaaa ctgaagtctt gtggacctca   1320
aacagtattg ttgtgttttg tggcacctca ggtacatatg gaacaggctc atggcctgat   1380
ggggcggacc tcaatctcat gcatatataa gctttcgcaa ttttagaaaa aactccttgt   1440
ttctactg                                                            1448

SEQ ID NO: 27         moltype = DNA   length = 1448
FEATURE               Location/Qualifiers
source                1..1448
                      mol_type = other DNA
                      organism = Influenza A
SEQUENCE: 27
atgaatccaa atcaaaagat aataacgatt ggctctgttt ctctcacaat ttccacaata   60
tgcttcttca tgcaaattgc catcctgata actactgtaa cattgcattt caagcaatat   120
gaattcaact cccccccaaa taccaagtg atgctgtgtg aaccaacaat aatagaaaga   180
aacataacag atagtgtata tttgaccaac accaccatag aaggaaat atgccccaaa    240
ccagcagaat acagaaattg gtcaaaaccg caatgtggca ttacaggatt tgcacctttc   300
tctaaggaca attcgattag gctttccgct ggtggggaca tctgggtgac aagagaacct   360
tatgtgtcat gcgatcttga caagtgttat caatttgccc ttggacaggg gacaacacta   420
aacaacgtgc attcaaataa cacagtacgt gataggaccc cttaccggac tctattgatg   480
aatgagttgg gtgttccttt ccatctgggg accaagcaag tgtgcatagc atggtccagc   540
tcaagttgtc acgatggaaa agcatggctg catgtttgta acgggggga tgataaaaat   600
gcaactgcta gcttcattta caatgggagg cttgtagata gtgttgtttc atggtccaac   660
gatattctca ggacccagga atcagaatgc gtttgtatca atggaacttg tacagtagta   720
atgactgatg gaaatgctac aggaaaagct gatactaaaa tactattcat cgaggagggg   780
aaaatcattc atactagcaa attgtcagga agtgctcagc atgtcgaaga gtgctcttgc   840
tatcctcgat atcctggtgt cagatgtgtc tgcagagaca actggaaagg atccaaccgg   900
cccatcatag atataaacat aaaggatcat agcattgttt ccagttatgt gtgttcagga   960
cttgttggag acacacccag aaaaagcgac agctccagca gtagccattg tttgaatcct  1020
aacaatgaag aagtggtca tggagtgaaa gctgggcct tgatgatgg aaatgacgtg    1080
tggatgggga gaacaatcaa cgagacgtca cgcttagggt atgaaaccct caaagtcgtt  1140
gaaggctggt ccaaccctaa gtccaaattg cagataaata ggcaagtcat agttgacaga  1200
ggtgataggt ccggttattc tggtattttc tctgttgaag gcaaaagctg catcaatcgg  1260
tgcttttatg tggagttgat taggggaaga aaagaggaaa ctgaagtctt gtggacctca  1320
aacagtattg ttgtgttttg tggcacctca ggtacatatg gaacaggctc atggcctgat  1380
ggggcggacc tcaatctcat gcatatataa gctttcgcaa ttttagaaaa aactccttg   1440
tttctact                                                           1448

SEQ ID NO: 28         moltype = DNA   length = 1410
FEATURE               Location/Qualifiers
source                1..1410
                      mol_type = other DNA
                      organism = Influenza A
SEQUENCE: 28
atgaatccaa atcaaaagat aataacgatt ggctctgttt ctctcacaat ttccacaata   60
tgcttcttca tgcaaattgc catcctgata actactgtaa cattgcattt caagcaatat   120
gaattcaact cccccccaaa taccaagtg atgctgtgtg aaccaacaat aatagaaaga   180
aacataacag atagtgtata tttgaccaac accaccatag aaggaaat atgccccaaa    240
ccagcagaat acagaaattg gtcaaaaccg caatgtggca ttacaggatt tgcacctttc   300
tctaaggaca attcgattag gctttccgct ggtgggaca tctgggtgac aagagaacct    360
tatgtgtcat gcgatcttga caagtgttat caatttgccc ttggacaggg aacaacacta   420
aacaacgtgc attcaaataa cacagtacgt gatagaaccc cttatcggac tctattgatg   480
aatgagttgg gtgttccttt ccatctgggg accaagcaag tgtgcatagc atggtccagc   540
tcaagctgtc acgatggaaa agcatggctg catgtttgta acgggggga tgataaaaat   600
gcaactgcta gcttcattta caatgggagg cttgtagata gtgttgtttc atggtccaac   660
gatattctca ggacccagga gtcagaatgc gtttgtatca atggaacttg tacagtagta   720
atgactgatg gaaatgctac aggaaaagct gatactaaaa tactattcat tgaggagggg   780
aaaatcgttc atactagcaa attgtcagga agtgctcagc atgtcgaaga gtgctcttgc   840
tatcctcgat atcctggtgt cagatgtgtc tgcagagaca actggaaagg atccaaccgg   900
cccatcatag atataaacat aaaggatcat agcattgttt ccaggtatgt gtgttcagga   960
cttgttggag acacacccag aaaaagcgac agctccagca gtagccattg tttgaaccct  1020
aacaatgaaa aagtgatca tggagtgaaa gctgggcct tgatgatgg aaatgacgtg    1080
tggatgggga gaacaatcaa cgagacgtcg cgcttagggt atgaaaccct caaagtcgtt  1140
gaaggctggt ccaaccctaa gtccaaattg cagataaata ggcaagtcat agttgacaga  1200
ggtgataggt ccggttattc tggtattttc tctgttgaag gcaaaagctg catcaatcgg  1260
tgcttttatg tggagttgat taggggaaga aaagaggaaa ctgaagtctt gtggacctca  1320
aacagtattg ttgtgttttg tggcacctca ggtacatatg gaacaggctc atggcctgat  1380
ggggcggacc tcaatctcat gcatatataa                                   1410

SEQ ID NO: 29         moltype = DNA   length = 1434
FEATURE               Location/Qualifiers
source                1..1434
                      mol_type = other DNA
                      organism = Influenza A
SEQUENCE: 29
atgaatccaa atcaaaagat aataacgatt ggctctgttt ctctcaccat ttccacaata   60
tgcttcttca tgcaaattgc catcctgata actactgtaa cattgcattt caagcaatat   120
gaattcaact cccccccaaa caaccaagtg atgctgtgtg aaccaacaat aatagaaaga   180
aacataacag atagtgtata tttgaccaac accaccatag agaggaaat atgccccaaa    240
```

-continued

```
ccagcagaat acagaaattg gtcaaaaccg caatgtggca ttacaggatt tgcacctttc  300
tctaaggaca attcgattag gctttccgct ggtggggaca tctgggtgac aagagaacct  360
tatgtgtcat gcgatcctga caagtgttat caatttgccc ttggacaggg aacaacaata  420
aacaacgtgc attcaaataa cacagcacgt gataggaccc ctcatcggac tctattgatg  480
aatgagttgg gtgttccttt ccatctgggg accaagcaag tgtgcatagc atggtccagc  540
tcaagttgtc acgatggaaa agcatggctg catgtttgta taacggggga tgataaaaat  600
gcaactgcta gtttcattta caatgggagg cttgtagata gtgttgtttc atggtccaaa  660
gatattctca ggacccagga gtcagaatgc gtttgtatca atggaacttg tacagtagta  720
atgactgatg gaaatgctac aggaaaagct gatactaaaa tattattcat tgaggagggg  780
aaaatcgttc atactagcaa attgtcagga agtgctcagc atgtcgaaga gtgctcttgc  840
tatcctcgat accctggtgt cagatgtgtc tgcagagaca actggaaagg atccaaccgg  900
cccatcgtag atataaacat aaaggatcat agcattgttt ccagttatgt gtgttcagga  960
cttgttggag acacacccag aaaaaccgac agctccagca gcagccattg cttgaatcct  1020
aacaatgaaa aggtggtca tggagtgaaa ggctgggcct ttgatgatgg aaatgacgtg  1080
tggatgggga gaacaatcaa cgagacgtca cgcttagggt atgaaacctt caaagtcgtt  1140
gaaggctggt ccaaccctaa gtccaaattg cagataaata ggcaagtcat agttgacaga  1200
ggtgataggt ccggttattc tggtatttc tctgttgaag gcaaaagctg catcaatcgg  1260
tgcttttatg tggagttgat taggggaaga aaagaggaaa ctgaagtctt gtggacctca  1320
aacagtattg ttgtgttttg tggcacctca ggtacatatg gaacaggctc atggcctgat  1380
ggggcggacc tcaatctcat gcatatataa gctttcgcaa ttttagaaaa aact        1434

SEQ ID NO: 30           moltype = DNA  length = 2233
FEATURE                 Location/Qualifiers
source                  1..2233
                        mol_type = other DNA
                        organism = Influenza A
SEQUENCE: 30
agcgaaagca ggtactgatc caaaatggaa gattttgtgc gacaatgctt caatccgatg  60
attgtcgagc ttgcggaaaa aacaatgaaa gagtatgggg aggacctgaa aatcgaaaca  120
aacaaatttg cagcaatatg cactcacttg gaagtatgct tcatgtattc agattttcac  180
ttcatcaatg agcaaggcga gtcaataatc gtagaacttg gtgatccaaa tgcacttttg  240
aagcacagat ttgaaataat cgagggaaga gatcgcacaa tggcctggac agtagtaaac  300
agtatttgca acactacagg ggctgagaaa ccaaagtttc taccagattt gtatgattac  360
aaggagaata gattcatcga aattggagta acaaggagag aagttcacat atactatctg  420
gaaaaggcca ataaaattaa atctgagaaa acacacatcc acattttctc gttcactggg  480
gaagaaatgg ccacaaaggc agactacact ctcgatgaag aaagcagggc taggatcaaa  540
accagactat tcaccataag acaagaaatg gccagcagag gcctctggga ttcctttcgt  600
cagtccgaga gaggagaaga gacaattgaa gaaaggtttg aaatcacagg aacaatgcgc  660
aagcttgccg accaaagtct cccgccgaac ttctccagcc ttgaaaattt tagagcctat  720
gtggatggat tcgaaccgaa cggctacatt gagggcaagc tgtctcaaat gtccaaagaa  780
gtaaatgcta gaattgaacc tttttttgaaa acaacaccac gaccacttag acttccgaat  840
gggcctccct gttctcagcg gtccaaattc ctgctgatgg atgccttaaa attaagcatt  900
gaggacccaa gtcatgaagg agagggaata ccgctatatg atgcaatcaa atgcatgaga  960
acattctttg gatggaagga acccaatgtt gttaaaccac acgaaaaggg aataaatcca  1020
aattatcttc tgtcatggaa gcaagtactg gcagaactgc aggacattga gaatgaggag  1080
aaaattccaa agactaaaaa tatgaagaaa acaagtcagc taaagtgggc acttggtgag  1140
aacatggcac cagaaaaggt agactttgac gactgtaaag atgtaggtga tttgaagcaa  1200
tatgatagtg atgaaccaga attgaggtcg cttgcaagtt ggattcagaa tgagtttaac  1260
aaggcatgcg aactgacaga ttcaagctgg atagagctcg atgagattgg agaagatgtg  1320
gctccaattg aacacattgc aagcatgaga aggaattatt tcacatcaga ggtgtctcac  1380
tgcagagcca cagaatacat aatgaaggga gtgtacatca atactgcctt gcttaatgca  1440
tcttgtgcag caatggatga tttccaatta attccaatga taagcaagtg tagaactaag  1500
gagggaaggc gaaagaccaa cttgtatggt ttcatcataa aggaagatc ccacttaagg  1560
aatgacaccg acgtggtaaa ctttgtgagc atggagtttt ctctcactga cccaagactt  1620
gaaccacata aatgggagaa gtactgtgtt cttgagatag gagatatgct tataagaagt  1680
gccataggcc aggtttcaag gcccatgttc ttgtatgtga gaacaaatgg aacctcaaaa  1740
attaaaatga aatggggaat ggagatgagg cgttgcctcc tccagtcact tcaacaaatt  1800
gagagtatga ttgaagctga gtcctctgtc aaagagaaag acatgaccaa agagttcttt  1860
gagaacaaat cagaaacatg gcccattgga gagtccccca aaggagtgga ggaaagttcc  1920
attgggaagg tctgcaggac tttattagca aagtcggtat tcaacagctt gtatgcatct  1980
ccacaactag aaggatttc agctgaatca agaaaactgc ttcttatcgt tcaggctctt  2040
agggacaacc tggaacctgg gacctttgat cttgggggc tatatgaagc aattgaggag  2100
tgcctgatta atgatccctg ggttttgctt aatgcttctt ggttcaactc cttccttaca  2160
catgcattga gttagttgtg gcagtgctac tatttgctat ccatactgtc caaaaaagta  2220
ccttgtttct act                                                     2233

SEQ ID NO: 31           moltype = DNA  length = 2341
FEATURE                 Location/Qualifiers
source                  1..2341
                        mol_type = other DNA
                        organism = Influenza A
SEQUENCE: 31
agcgaaagca ggcaaaccat ttgaatggat gtcaatccga ccttactttt cttaaaagtg  60
ccagcacaaa atgctataag cacaactttc ccttatactg gagaccctcc ttacagccat  120
gggacaggaa caggatacac catggatact gtcaacagga cacatcagta ctcagaaaag  180
ggaagatgga caacaaacac cgaaactgga gcaccgcaac tcaacccgat tgatgggcca  240
ctgccagaag acaatgaacc aagtggttat gcccaaacag attgtgtatt ggaggcgatg  300
gctttccttg aggaatccca tcctggtatt tttgaaaact cgtgtattga aacgatggag  360
gttgttcagc aaacacgagt agacaagctg acacaaggcc gacagaccta tgactggact  420
```

```
ctaaatagaa accaacctgc tgcaacagca ttggccaaca caatagaagt gttcagatca    480
aatggcctca cggccaatga gtctggaagg ctccatagact tccttaagga tgtaatggag   540
tcaatgaaca aagaagaaat ggggatcaca actcattttc agagaaagag acgggtgaga   600
gacaatatga ctaagaaaat gataacacag agaacaatgg gtaaaagaa gcagagattg    660
aacaaaagga gttatctaat tagagcattg accctgacca caatgaccaa agatgctgag   720
agagggaagc taaacggag agcaattgca accccaggga tgcaaataag ggggtttgta    780
tactttgttg agacactggc aaggagtata tgtgagaaac ttgaacaatc agggttgcca   840
gttggaggca atgagaagaa agcaaagttg gcaaatgttg taaggaagat gatgaccaat   900
tctcaggaca ccgaactttc tttcaccatc actggagata acaccaaatg gaacgaaaat   960
cagaatcctc ggatgttttt ggccatgatc acatatatga ccagaaatca gcccgaatgc  1020
ttcagaaatg ttcaagtat tgctccaata atgttctcaa acaaaatggc gagactggga   1080
aaagggtata tgtttgagag caagagtatg aaacttagaa ctcaaatacc tgcagaaatg  1140
ctagcaagca tcgatttgaa atatttcaat gattcaacaa gaaagaagat tgaaaaaatc  1200
cgaccgctct aatagaggg gactgcatca ttgagccctg gaatgatgat gggcatgttc   1260
aatatgttaa gcactgtatt aggcgtctcc atcctgaatc ttggacaaaa gagatacacc  1320
aagactactt actggtggga tggtcttcaa tcctctgacg attttgctct gattgtgaat  1380
gcacccaatc atgaagggat tcaagccgga gtcgacaggt tttatcgaac ctgtaagcta  1440
cttggaatca atatgagcaa gaaaaagtct tacataaaca acaggtac atttgaattc    1500
acaagttttt tctatcgtta tgggtttgtt gccaattta gcatggagct tcccagtttt   1560
ggggtgtctg ggatcaacga gtcagcggac atgagtattg gagttactgt catcaaaaac  1620
aatatgataa caatgatct tggtccagca acagctcaaa tggcccttca gttgttcatc  1680
aaagattaca ggtacacga ccgatgccat ataggtgaca cacaaataca acccgaaga   1740
tcatttgaaa taagaaact gtgggagcaa acccgttcca aagctggact gctggtctcc   1800
gacgaggcc caatttata caacattaga atctccaca ttcctgaagt ctgcctaaaa    1860
tgggaattga tggatgagga ttaccagggg cgtttatgca acccactgaa cccatttgtc  1920
agccataaag aaattgaatc aatgaacaat gcagtgatga tgccacacct tggtccagcc  1980
aaaaacatgg agtatgatgc tgttgcaaca cacactcct ggatcccaa aagaaatcga    2040
tccatcttga atacaagtca aagaggagta cttgaggatg aacaaatgta ccaaaggtgc  2100
tgcaatttat ttgaaaaatt cttccccagc agttcataca aagaccagt cgggatatcc  2160
agtatggtgg aggctatggt ttccagagcc cgaattgata cacggattga tttcgaatct  2220
ggaaggataa agaaagaaga gttcactgag atcatgaaga tctgttccac cattgaagag  2280
ctcagacggc aaaaatagtg aatttagctt gtccttcatg aaaaatgcc ttgtttctac    2340
t                                                                  2341

SEQ ID NO: 32           moltype = DNA  length = 2341
FEATURE                 Location/Qualifiers
source                  1..2341
                        mol_type = other DNA
                        organism = Influenza A
SEQUENCE: 32
agcgaaagca ggtcaattat attcaatatg gaaagaataa aagaactacg aaatctaatg    60
tcgcagtctc gcacccgcga gatactcaca aaaaccaccg tggaccatat ggccataatc   120
aagaagtaca catcaggaag acaggagaag aacccacgac ttaggatgaa atggatgatg   180
gcaatgaaat atccaattac agcagacaag aggataacgg aaatgattcc tgagagaaat   240
gagcaaggac aaactttatg gagtaaaatg aatgatgccg atcagaccg agtgatggta   300
tcacctctgg ctgtgacatg gtggaatagg aatggaccaa taacaaatac agttcattat   360
ccaaaaatct acaaaactta ttttgaaaga gtcgaaagc taaagcatgg aacctttggc   420
cctgtccatt ttagaaacca agtcaaaata cgtcggagag ttgacataaa tcctggtcat   480
gcagatctca gtgccaagga ggcacaggat gtaatcatgg aagttgtttt ccctaacgaa   540
gtgggagcca ggatactaac atcggaatcg caactaacga taaccaaaga gaagaaagaa   600
gaactccagg attgcaaaat ttctcctttg atggttgaca catgttgga gaaagaaatg  660
gtccgcaaaa cgagattcct cccagtggct ggtggaacaa gcagtgtgta cattgaagtg    720
ttgcatttga ctcaaggaac atgctgggaa cagatgtata ctccaggagg gaagtgagg    780
aatgatgatg ttgatcaaag cttgattatt gctgctagga catagtgag aagagctgca    840
gtatcagcag atccactagc atctttattg gagatgtgca acagcacaca gattggtgga   900
attaggatgg tagacatcct taggcagaac ccaacagaag agcaagccgt ggatatatgc   960
aaggctgcaa tgggactgag aattagctca tccttcagtt ttggtggatt cacatttaag  1020
agaacaagcg atcatcagt caagagagag gaagaggtgc ttacgggcaa tcttcaaaca  1080
ttgaagataa gagtgcatga gggatatgaa gagttccaaa tggttgggaa aagagcaaca  1140
gccatactca gaaaagcaac caggagattg attcagctga tagtgagtgg gagagacgaa  1200
cagtcgattg ccgaagcaat aattgtggcc atgtattttt cacaagagga ttgtatgata  1260
aaagcagtca gaggtgatct gaatttcgtc aatagggcga atcaacgatt gaatcctatg  1320
catcaacttt taagacattt tcagaaggat gcgaaagtgc ttttttcaaaa ttggggagtt  1380
gaacctatcg acaatgtgat gggaatgatt gggataattgc ccgatcatg ccaagcatc   1440
gagatgtcaa tgagaggagt gagaatcagc aaaatgggtg tagatgagta ctccagcacg  1500
gagagggtag tggtgagcat tgaccgtttt tgagaatcc gggaccaacg aggaaatgta  1560
ctactgtctc ccgaggaggt cagtgaaaca cagggaacag agaaactgac aataaacttac  1620
tcatcgtcaa tgatgtggga gattaatggt cctgaatcag tgttggtcaa tacctatcaa  1680
tggatcatca gaaactggga aactgttaaa attcagtggt cccagaaccc tacaatgcta  1740
tacaataaaa tggaatttga accattttcag tcttttagtac ctaaggccat tagaggccaa  1800
tacagtgggt ttgtaagaac tctgttccaa caaatggggg atgtgcttgg acatttgat   1860
accgcacaga taataaaact tcttcccttc gcagccgctc caccaaagca agtagaatg   1920
cagttctcct catttactgt gaatgtgagg ggatcaggaa tgagaatact tgtaagggc   1980
aattctccta tattcaacta taacaaggcc acgaagagca tcacagttct cggaaaggat  2040
gctggcactt taactgaaga cccagatgaa ggcacagctg gagtggagtc cgctgttctg   2100
aggggattcc tcattctggg caagaagac aagagatatg gccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc  2280
aaaagaattc ggatggccat caattagtgt cgaatagttt aaaaacgacc ttgtttctac   2340
```

```
t                                                                    2341

SEQ ID NO: 33            moltype = DNA   length = 1565
FEATURE                  Location/Qualifiers
source                   1..1565
                         mol_type = other DNA
                         organism = Influenza A
SEQUENCE: 33
agcaaaagca gggtagataa tcactcactg agtgacatca aaatcatggc gtctcaaggc   60
accaaacgat cttacgaaca gatggagact gatggagaac gccagaatgc cactgaaatc  120
agagcatccg tcggaaaaat gattggtgga attggacgat tctacatcca aatgtgcacc  180
gaactcaaac tcagtgatta tgagggacgg ttgatccaaa acagcttaac aatagagaga  240
atggtgctct ctgcttttga cgaaaggaga ataaaatacc ttgaagaaca tcccagtgcg  300
gggaaagatc ctaagaaaac tggaggacct atatacagga gagtaaacgg aaagtgatg   360
agagaactca tcctttatga caaagaagaa ataaggcgaa tctggcgcca agctaataat  420
ggtgacgatg caacggctgg tctgactcac atgatgatct ggcattccaa tttgaatgat  480
gcaacttatc agaggacaag agctcttgtt cgcaccggaa tggatcccag gatgtgctct  540
ctgatgcaag gttcaactct ccctaggagg tctggagccg caggtgctgc agtcaaagga  600
gttggaacaa tggtgatgga attggtcaga atgatcaaac gtgggatcaa tgatcggaac  660
ttctggaggg gtgagaatgg acgaaaaaca agaattgctt atgaaagaat gtgcaacatt  720
ctcaaaggga aatttcaaac tgctgcacaa aaagcaatga tggatcaagt gagagagagc  780
cggaacccag ggaatgctga gttcgaagat ctcacttttc tagcacggtc tgcactcata  840
ttgagagggt cggttgctca caagtcctgc ctgcctgcct gtgtgtatgg acctgccgta  900
gccagtgggt acgactttga agggagggga tactctctag tcggaataga ccctttcaga  960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatgaa tcaagtacac ttgaactgag aagcaggtac 1200
tgggccataa ggaccagaag tggagggaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatga aaagtgcaag accagaagat gtgtctttcc aggggcgggg agtcttcgag 1440
ctctcggacg aaaaggcagc gagcccgatc gtgccttcct tgacatgag taatgaagga 1500
tcttatttct tcggagacaa tgcagaggag tacgacaatt aaagaaaaat accccttgttt 1560
ctact                                                             1565

SEQ ID NO: 34            moltype = DNA   length = 1027
FEATURE                  Location/Qualifiers
source                   1..1027
                         mol_type = other DNA
                         organism = Influenza A
SEQUENCE: 34
agcaaaagca ggtagatatt gaaagatgag tcttctaacc gaggtcgaaa cgtacgtact   60
ctctatcatc ccgtcaggcc ccctcaaagc cgagatcgca cagagacttg aagatgtctt  120
tgcagggaag aacaccgatc ttgaggttct catggaatgg ctaaagacaa gaccaatcct  180
gtcacctctg actaagggga ttttaggatt tgtgttcacg ctcaccgtgc ccagtgagcg  240
aggactgcag cgtagacgct ttgtccaaaa tgcccttaat gggaacggtg atccaaataa  300
catggacaaa gcagttaaac tgtataggaa gctcaagagg gagataacat tccatgggga  360
caaagaaatc tcactcagtt attctgctgg tgcacttgcc agttgtatgg gcctcatata  420
caacaggatg ggggctgtga ccactgaagt ggcatttggc ctggtatgtg caacctgtga  480
acagattgct gactcccagc atcggtctca taggcaaatg gtgacaacaa ccaatcctt   540
aatcagacat gagaacagaa tggttttagc cagcactaca gctaaggcta tggagcaaat  600
ggctggatcg agtgagcaag cagcagaggc catggaggtt gctagtcagg ctagacaaat  660
ggtgcaagcg atgagaacca ttgggactca tcctagctcc agtgctggtc tgaaaaatga  720
tcttcttgaa aatttgcagg cctatcagaa acgaatgggg gtgcagatgc aacgattcaa  780
gtgatcctct cactattgcc gcaaatatca ttgggatctt gcacttgaca ttgtggattc  840
ttgatcgtct ttttttcaaa tgcatttacc gtcgctttaa atacgactg aaaggagggc  900
cttctacgga aggagtgcca aagtctatga gggaagaata tcgaaggaa cagcagagtg  960
ctgtggatgc tgacgatggt catttgtca gcatagagct ggagtaaaaa actaccttgt 1020
ttctact                                                           1027

SEQ ID NO: 35            moltype = DNA   length = 890
FEATURE                  Location/Qualifiers
source                   1..890
                         mol_type = other DNA
                         organism = Influenza A
SEQUENCE: 35
agcaaaagca gggtgacaaa aacataatgg atccaaacac tgtgtcaagc tttcaggtag   60
attgctttct ttggcatgtc cgcaaacgag ttgcagacca agaactaggc gatgccccat  120
tccttgatcg gcttcgccga gatcagaaat ccctaagagg aaggggcagt actctcggtc  180
tggacatcaa gacagccaca cgtgctggaa agcagatagt ggagcggatt ctgaaagaag  240
aatccgatga ggcacttaaa atgaccatgg cctctgtacc tgcgtcgcgt tacctaactg  300
acatgactct tgaggaaatg tcaagggact ggtccatgct catacccaag cagaaagtgg  360
caggccctct ttgtatcaga taaggaccagg cgatcatgga taagaacatc atactgaaag  420
cgaacttcag tgtgatttttt gaccggctgg agactctaat attgctaagg ctttcaccg   480
aagagggagc aattgttggc gaaatttcac cattgccttc ttccaagga catactgctg  540
aggatgtcaa aaatgcagtt ggagtcctca tcggaggact tgaatggaat gataacacag  600
ttcgagtctc tgaaactcta cagagattcg cttggagaag cagtaatgag aatgggac   660
ctccactcac tccaaaacag aaacgagaaa tggcggggaac aattaggtca gaagtttgaa  720
```

```
gaaataagat ggttgattga agaagtgaga cacaaactga agataacaga gaatagtttt   780
gagcaaataa catttatgca agccttacat ctattgcttg aagtggagca agagataaga   840
actttctcgt ttcagcttat ttagtactaa aaaacaccct tgtttctact              890

SEQ ID NO: 36           moltype = DNA  length = 1433
FEATURE                 Location/Qualifiers
source                  1..1433
                        mol_type = other DNA
                        organism = Influenza A
SEQUENCE: 36
agtttaaaat gaatccaaac caaaagataa taaccattgg ttcgatcagt atgacaattg    60
gaatggctaa cttaatatta caaattgaaa acataatctc aatatgggtt agccactcaa   120
ttcaaattgg aaatcaaagc cagattgaaa catgcaatca aagcgtcatt acttatgaaa   180
acaacacttg ggtaaatcag acatatgtta acatcagcaa caccaacttt gctgctggac   240
agtcagtggt ttccgtgaaa ttagcgggca attcctctct ctgccctgtt agtggatggg   300
ctatatacag taaagacaac agtgtaagaa tcggttccaa gggggatgtg tttgtcataa   360
gggaaccatt catatcatgc tctcccttgg aatgcagaac cttcttcttg actcaagggg   420
ccttgctaaa tgacaaacat tccaatggaa ccattaaaga caggagccca tatcgaaccc   480
taatgagctg tccattggt gaagttccct ctccatacaa ctcaagattt gagtcagtcg    540
cttggtcagc aagtgcttgt catgatgca tcaattggct aacaattgga atttctggcc    600
cagacagtgg ggcagtggct gtgttaaagt acaatgcat aataacagac actatcaaga    660
gttggaggaa caatatattg agaacacaag tctgaattg tgcatgtgta agatgttctt    720
gctttaccat aatgaccgat ggaccaagtg atggacaggc ctcatacaaa atcttcagaa    780
tagaaagggg aaagataatc aaatcagtcg aaatgaaagc ccctaattat cactatgagg   840
aatgctcctg ttaccctgat tctagtgaaa tcacatgtgt gtgcagggat aactggcatg   900
gctcgaatcg accgtgggtg tctttcaacc agaatctgga atatcagatg ggatacatat   960
gcagtgggt tttcggagac aatccacgcc ctaatgataa gacaggcagt tgtggtccaa   1020
tatcgtctaa tggagcaaat ggagtaaaag gattttcatt caaatacggc aatggtgttt   1080
ggataggag aactaaaagc attagttcaa gaaaggttt tgagatgatt tgggatccga   1140
atggatggac tgggactgac aataaattct caataaagca agatatcgta ggaataaatg   1200
agtggtcagg gtatagcggg agttttgttc agcatccaga actaacaggg ctggattgta   1260
taagaccttg cttctgggtt gaactaataa gagggcgacc cgaagagaac acaatctgga   1320
ctagcggag cagcatatcc tttttgtgg taaacagtga cactgtgggt tggtcttggc   1380
cagacggtgc tgagttgcca tttaccattg acaagtaatt tgttcaaaaa act         1433

SEQ ID NO: 37           moltype = AA  length = 469
FEATURE                 Location/Qualifiers
source                  1..469
                        mol_type = protein
                        organism = Influenza A
SEQUENCE: 37
MNPNQKIITI GSISMTIGMA NLILQIGNII SIWVSHSIQI GNQSQIETCN QSVITYENNT    60
WVNQTYVNIS NTNFAAGQSV VSVKLAGNSS LCPVSGWAIY SKDNSVRIGS KGDVFVIREP   120
FISCSPLECR TFFLTQGALL NDKHSNGTIK DRSPYRTLMS CPIGEVPSPY NSRFESVAWS   180
ASACHDGINW LTIGISGPDS GAVAVLKYNG IITDTIKSWR NNILRTQESE CACVNGSCFT   240
IMTDGPSDGQ ASYKIFRIEK GKIIKSVEMK APNYHYEECS CYPDSSEITC VCRDNWHGSN   300
RPWVSFNQNL EYQMGYICSG VFGDNPRPND KTGSCGPVSS NGAVKGFS PKYGNGVWIG    360
RTKSISSRKG FEMIWDPNGW TGTDNKFSIK QDIVGINEWS GYSGSFVQHP ELTGLDCIRP   420
CFWVELIRGR PEENTIWTSG SSISFCGVNS DTVGWSWPDG AELPFTIDK              469

SEQ ID NO: 38           moltype = DNA  length = 2341
FEATURE                 Location/Qualifiers
source                  1..2341
                        mol_type = other DNA
                        organism = Influenza A
SEQUENCE: 38
agcgaaagca ggtcaattat attcaatatg gaaagaataa agaactaag aaatctaatg     60
tcgcagtctc gcacccgcga gatactcaca aaaaccaccg tggaccatat ggccataatc   120
aagaagtaca catcaggaag acaggagaag aacccagca ttaggatgaa atggatgatg    180
gcaatgaaat atccaattac agcagacaag aggataacgg aaatgattcc tgagagaaat   240
gagcaaggac aaacttatg gagtaaaatg aatgatgccg atcagaccg agtgatggta   300
tcacctctgg ctgtgacatg gtggaatagg aatggaccaa tgacaaatac agttcattat   360
ccaaaaatct acaaaactta ttttgaaaga gtcgaaaggc taaagcatgg aacctttggc   420
cctgtccatt ttagaaacca agtcaaaata cgtcggaacg ttgacataaa tcctggtcat   480
gcagatctca gtgccaagga ggcacaggat gtaatcatgg aagttgtttt ccctaacgaa   540
gtgggagcca ggatactaac atcggaatcg caactaacga taaccaaaga gaagaaagaa    600
gaactccagg attgcaaaat ttctcctttg atggttgcat acatgttgga gagaactg     660
gtccgcaaaa cgagattcct cccagtggct ggtggaacaa gcagtgtgca cattgaagtg   720
ttgcatttga ctcaaggaac agctgggaa cagatgtata ctccaggagg ggaagtgaag   780
aatgatgatg ttgatcaaag cttgattat gctgctagga acatagtgag aagagctcaa   840
gtatcagcag cccactagc atctttattg gagatgtgcc acagcacaca gattggtgga   900
attaggatgt tagacatcct taagcagaac ccaacagaag agcaagccgt ggatatatgc   960
aaggctgcaa tgggactgag aattagctca tccttcagtt ttggtggatt cacatttaag  1020
agaacagcg gatcatcgat caagagagag gaagttggcg ttacgcagcaa tctttcaaaca  1080
ttgaagataa gagtgcatga gggatctgaa gagttcacaa tggttgggag aagagcaaca  1140
gccatactca gaaagcaac caggagttg attcagctga tagtgagtgg agagacgaa    1200
cagtcgattc cgaagcaat aattgtgcc atggtatttt cacaagagga ttgtatgata  1260
aaagcagtta gaggtgatct gaatttcgtc aatagggcga atcagcgact gaatcctatg  1320
catcaacttt taagacattt tcagaaggat gcgaaagtgc ttttttcaaaa ttgggggagtt  1380
```

```
gaacctatcg acaatgtgat gggaatgatt gggatattgc ccgacatgac tccaagcatc    1440
gagatgtcaa tgagaggagt gagaatcagc aaaatgggtg tagatgagta ctccagcacg    1500
gagagggtag tggtgagcat tgaccggttc ttgagagtca gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcac tgttggtcaa tacctatcaa    1680
tggatcatca gaaactggga aactgttaaa attcagtggt cccagaaccc tacaatgcta    1740
tacaataaaa tggaatttga accatttcag tcttttagtac ctaaggccat tagaggccaa    1800
tacagtgggt tgtaagaac tctgttccaa caaatgaggg atgtgcttgg acatttgat    1860
accgcacaga taataaaact tcttcccttc gcagccgctc caccaaagca aagtagaatg    1920
cagttctcct catttactgt gaatgtgagg ggatcaggaa tgagaatact tgtaaggggc    1980
aattctcctg tattcaacta caacaaggcc acgaagagac tcacagttct cggaaaggat    2040
gctggcactt taaccgaaga cccagatgaa ggcacagctg gagtggagtc cgctgttctg    2100
aggggattcc tcattctggg caagaagac aggagatatg ggccagcatt aagcatcaat    2160
gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                    2341

SEQ ID NO: 39          moltype = DNA   length = 2341
FEATURE                Location/Qualifiers
source                 1..2341
                       mol_type = other DNA
                       organism = Influenza A SEQUENCE: 39
agcgaaagca ggcaaaccat ttgaatggat gtcaatccga ccttactttt cttaaaagtg     60
ccagcacaaa atgctataag cacaactttc ccttataccg gagaccctcc ttacagccat    120
gggacaggaa caggatacac catggatact gtcaacagga cacatcagta ctcgaaaaag    180
ggaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga aacgatggag    360
gttgttcagc aaacacgagt agacaagctg acacaaggcc gacagaccta tgactggact    420
ttaaatagaa accagcctgc tgcaacagca ttggccaaca ataagaaagt gttcagatca    480
aatgccctca cggccaatga gtcaggaagg ctcatagact tccttaagga tgtaatggag    540
tcaatgaaaa aagaagaaat ggggatcaca actcattttc agagaaagag acgggtgaga    600
gacaatatga ctaagaaaat gataacacag agaacaatag gtaaaggaa acagagatta    660
aacaaaaggg gttatctaat tagagcattg acctgaaca caatgaccaa agatgctgag    720
agagggaagc taaacggag agcaattgca accccaggga tgcaaataag ggggtttgta    780
tactttgttg agacactggc aaggagtata tgtgagaaac ttgaacaatc agggttgcca    840
gttggaagca atgagaagaa agcaaagttg caaatgttg taaggaagat gatgaccaat    900
tctcaggaca ccgaactttc tttcaccatc actggagata acaccaaatg aacgaaaat    960
cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaggggtata tgtttgagag caagagtatg aaacttgaaa ctcaaatacc tgcagaaagc   1140
ctagcaagca ttgatttgaa atatttcaat gattcaacaa gaagaagact tgaaaaaatc   1200
cgaccgctct aatagaggg gactgcatca ttgagccctg aatgatgat gggcatgttc   1260
aatatgttaa gcactgtatt aggcgtctcc atcctgaatc ttgacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtc tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat agaggtgaca cacaaataca aacccgaaga   1740
tcatttgaaa taaagaaact gtgggagcaa accgttcca agctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatcccaa agaaatcga   2040
tccatcttga atacaagtca aagaggagta cttgaagatg aacaaatgta ccaaaggtgc   2100
tgcaatttat ttgaaaaatt cttccccagc agttcataca gaagaccagt cgggatatcc   2160
agtatggtgg aggctatggt ttccagagcc gaattgatg cacggattga tttcgaatct   2220
ggaaggataa agaagaaga gttcactgag atcatgaaga tctgttccac cattgaagag   2280
ctcagacggc aaaaatagtg aatttagctt gtccttcatg aaaaaatgcc ttgtttctac   2340
t                                                                    2341

SEQ ID NO: 40          moltype = DNA   length = 2233
FEATURE                Location/Qualifiers
source                 1..2233
                       mol_type = other DNA
                       organism = Influenza A SEQUENCE: 40
agcgaaagca ggtactgatt caaaatggaa gattttgtgc gacaatgctt caatccgatg     60
attgtcgagc ttgcggaaaa acaatgaaa gagtatgggg aggacctgaa atcgaaaca    120
aacaaatttg cagcaatatg cactcacttg gaagtatgct tcatgtattc agatttccaa    180
ttcatcaatg agcaaggcga gtcaataatc gtagaacttg gtgatccta tgcactttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggaaaata gattcatcga aattggagta acaaggagaa agttcacat atactatctg    420
gaaaaggcca ataaaattaa atctgagaaa acacacatcc acattttctc gttcactggg    480
```

-continued

```
gaagaaatgg ccacaagggc cgactacact ctcgatgaag aaagcagggc taggatcaaa     540
accaggctat tcaccataag acaagaaatg ccagcagag gcctctggga ttcctttcgt      600
cagtccgaga gaggagaaga gacaattgaa gaaaggtttg aaatcacagg aacaatgcgc     660
aagcttgccg accaaagtct cccgccgaac ttctccagcc ttgaaaattt tagagcctat     720
gtggatggat tcgaaccgaa cggctacatt gagggcaagc tgtctcaaat gtccaaagaa     780
gtaaatgcta gaattgaacc ttttttgaaa acaacaccac gaccacttag acttccgaat     840
gggcctccct gttctcagcg gtccaaattc ctgctgatgg atgccttaaa attaagcatt     900
gaggacccaa gtcatgaagg agagggaata ccgctatatg atgcaatcaa atgcatgaga     960
acattctttg gatggaagga acccaatgtt gttaaaccac agaaaagg aataaatcca      1020
aattatcttc tgtcatggaa gcaagtactg gcagaactgc aggacattga gaatgaggag    1080
aaaattccaa agactaaaaa tatgaaaaaa acaagtcagc taaagtgggc acttggtgag    1140
aacatggcac cagaaaaggt agactttgac gactgtaaag atgtaggtga tttgaagcaa    1200
tatgatagtg atgaaccaga attgaggtcg cttgcaagtt ggattcagaa tgagttcaac    1260
aaggcatgcg aactgacaga ttcaagctgg atagagcttg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt acttaatgca    1440
tcttgtgcag caatggatga tttccaatta attccaatga taagcaagtg tagaactaag    1500
gagggaaggc gaaagaccaa cttgtatggt ttcatcataa aaggaagatc ccacttaagg    1560
aatgacaccg acgtggtaaa ctttgtgagc atggagtttt ctctcactga cccaagactt    1620
gaaccacaca aatgggagaa gtactgtgtt cttgagatag agatatgct tctaagaagt    1680
gccataggcc aggtttcaag gcccatgttc ttgtatgtga ggacaaatgg aacctcaaaa    1740
attaaaatga aatgggaat ggagatgagg cgttgtctcc tccagtcact tcaacaaatt    1800
gagagtatga ttgaagctga gtcctctgtc aaagagaag acatgaccaa agagttcttt    1860
gagaacaaat cagaaacatg gccattgga gagtctccca aaggagtgga ggaaagttcc    1920
attgggaagg tctgcaggac tttattagca aagtcggtat taacagctt gtatgcatct    1980
ccacaactag aaggattttc agctgaatca agaaaactgc ttcttatcgt tcaggctctt    2040
agggacaatc tggaacctgg gacctttgat cttgggggc tatatgaagc aattgaggag    2100
tgcctaatta atgatccctg ggttttgctt aatgcttctt ggttcaactc cttccttaca    2160
catgcattga gttagttgtg gcagtgctac tatttgctat ccatactgtc caaaaagta    2220
ccttgtttct act                                                       2233

SEQ ID NO: 41           moltype = DNA   length = 1565
FEATURE                 Location/Qualifiers
source                  1..1565
                        mol_type = other DNA
                        organism = Influenza A
SEQUENCE: 41
agcaaaagca gggtagataa tcactcactg agtgacatca aaatcatggc gtcccaaggc      60
accaaacggt cttacgaaca gatggagact gatggagaac gccagaatgc cactgaaatc     120
agagcatccg tcggaaaaat gattggtgga attggacgat tctacatcca aatgtgcaca     180
gaacttaaac tcagtgatta tgagggacgt ttgatccaaa acagcttaac aatagagaga     240
atggtgctct ctgcttttga cgaaaggaga aataaatacc tggaagaaca tcccagtgcg    300
gggaaagatc ctaagaaaac tggaggacct atatacagga gagtaaacgg aaagtgatgt    360
agagaactca tccttttatga caagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatcccag gatgtgctct    540
ctgatgcaag gttcaactct ccctaggagg tctggagccg tgtctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcactttc tagcacggtc tgcactcata    840
ttgagagggt cggttgctca caagtcctgc ctgcctgcct gtgtgtatgg acctgccgta    900
gccagtgggt acgactttga agagaggga tactctctag tcggaataga cccttttcaga    960
ctgcttcaaa acagccaagt gtacagccta atcagaccaa atgagaatcc agcacacaag   1020
agtcaactgg tgtggatggc atgccattca gccgcatttg aagatctaag agtattgagc   1080
ttcatcaaag gacgaaggt ggtcccaaga gggaagcttt ccactagagg agttcaaatt   1140
gcttccaatg aaaatatgga gactatgaa tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccgtt   1320
atggcagcat tcactgggaa tacagagggg agaacatctg acatgaggac cgaaatcata   1380
aggatgatgg aaagtgcaag accagaagat gtgtctttcc aggggcggg agtcttcgag   1440
ctctcggacg aaaaggcagc gagcccgatc gtgccttcct tgacatgag taatgaagga   1500
tcttatttct tcggagacaa tgcagaggag tacgacaatt aaagaaaaat acccttgttt   1560
ctact                                                               1565

SEQ ID NO: 42           moltype = DNA   length = 1027
FEATURE                 Location/Qualifiers
source                  1..1027
                        mol_type = other DNA
                        organism = Influenza A
SEQUENCE: 42
agcaaaagca ggtagatatt gaaagatgag tcttctaacc gaggtcgaaa cgtacgttct     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga tttaggatt tgtgttcacg ctcaccgtgc ccagtgagcg    240
aggactgcag cgtagacgct ttgtccaaaa tgcccttaat gggacggg atccaaataa    300
catggacaaa gcagttaaac tgtataggaa gctcaagagg gagataacat tccatgggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
```

```
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggt gcagatgca aacggttcaa     780
gtgatcctct cgctattgcc gcaaatatca ttgggatctt gcacttgata ttgtggattc    840
ttgatcgtct tttttcaaa tgcatttacc gtcgctttaa atacgactg aaaggagggc      900
cttctacgga aggagtgcca aagtctatga gggaagaata tcgaaaggaa cagcagagtg    960
ctgtggatgc tgacgatggt catttgtca gcatagagct ggagtaaaaa actaccttgt     1020
ttctact                                                              1027

SEQ ID NO: 43            moltype = DNA  length = 890
FEATURE                  Location/Qualifiers
source                   1..890
                         mol_type = other DNA
                         organism = Influenza A
SEQUENCE: 43
agcaaaagca gggtgacaaa gacataatgg atccaaacac tgtgtcaagc tttcaggtag    60
attgctttct ttggcatgtc cgcaaacgag ttgcagacca agaactaggt gatgccccat    120
tccttgatcg gcttcgccga gatcagaaat ccctaagagg aagggcagc actcttggtc     180
tggacatcga gacagccaca cgtgctggaa agcagatagt ggagcggatt ctgaaagaag    240
aatccgatga ggcacttaaa atgaccatgg cctctgtacc tgctcgcat tacctaaccg     300
acatgactct tgaggaaatg tcaagggaat ggtccatgt catacccaag cagaaagtgg     360
caggcccttct ttgtatcaga atggaccagg cgatcatgga taaaaacatc atactgaaag  420
cgaacttcag tgtgattttt gaccggctgg agactctaat attgctaagg ctttcaccg    480
aagagggagc aattgttggc gaaatttcac cattgccttc ttccagga catactgctg     540
aggatgtcaa aaatgcagtt ggagtcctca tcggaggact tgaatggaat gataacacag   600
ttcgagtctc tgaaactcta cagagattcg cttggagaag cagtaatgag aatgggagac   660
ctccactcac tccaaaacag aaacgagaaa tggcgggaac aattaggtca gaagtttgaa    720
gaaataagat ggttgattga agaagtgaga cacaaactga aggtaacaga aatagttttt    780
gagcaaataa catttatgca agccttacat ctattgcttg aagtggagca agagataaga    840
actttctcat ttcagcttat ttaataataa aaaacaccct tgtttctact                890

SEQ ID NO: 44            moltype = AA   length = 469
FEATURE                  Location/Qualifiers
source                   1..469
                         mol_type = protein
                         organism = Influenza A
SEQUENCE: 44
MNPNQKIITI GSVSLTISTI CFFMQIAILI TTVTLHFKQY EFNSPPNNQV MLCEPTIIER    60
NITEIVYLTN TTIEKEICPK PAEYRNWSKP QCGITGFAPF SKDNSIRLSA GGDIWVTREP    120
YVSCDPDKCY QFALGQGTTL NNVHSNNTVR DRTPYRTLLM NELGVPFHLG TKQVCIAWSS    180
SSCHDGKAWL HVCITGDDKN ATASFIYNGR LVDSVVSWSK DILRTQESEC VCINGTCTVV    240
MTDGNATGKA DTKILFIEEG KIVHTSKLSG SAQHVEECSC YPRYPGVRCV CRDNWKGSNR   300
PIVDINIKDH SIVSSYVCSG LVGDTPRKND SSSSSHCLNP NNEEGGHGVK GWAFDDGNDV    360
WMGRTINETS RLGYETFKVV EGWSNPKSKL QINRQVIVDR GDRSGYSGIF SVEGKSCINR    420
CFYVELIRGR KEETEVLWTS NSIVVFCGTS GTYGTGSWPD GADLNLMHI                469

SEQ ID NO: 45            moltype = AA   length = 466
FEATURE                  Location/Qualifiers
source                   1..466
                         mol_type = protein
                         organism = Influenza B
SEQUENCE: 45
MLPSTIQTLT LFLTSGGVLL SLYVSASLSY LLYSDILLKF SRTEITAPIM PLDCANASNV    60
QAVNRSATKG VTLLLPEPEW MYPRLSCPGS TFQKALLISP HRFGETKGNS APLIIREPFI    120
ACGPKECKHF ALTHYAAQPG GYYNGTREDR NKLRHLISVK LGKIPTVENS IFHMAAWSGS    180
ACHDGREWTY IGVDGPDSNA LLKIKYGEAY TDTYHSYAKN TLRTQESACN CIGGDCYLMI    240
TDGPASGISE CRFLKIREGR IIKEIFPTGR VKHTEEECTCG FASNKTIECA CRDNSYTAKR   300
PFVKLNVETD TAEIRLMCTE TYLDTPRPND GSITGPCESN GDKGSGGIKG GFVHQRMASK   360
IGRWYSRTMS KTKRMGMGLY VKYDGDPWTD SEALALSGVM VSMEEPGWYS FGFEIKDKKC    420
DVPCIGIEMV HDGGKTTWHS AATAIYCLMG SGQLLWDTVT GVNMTL                   466

SEQ ID NO: 46            moltype = AA   length = 466
FEATURE                  Location/Qualifiers
source                   1..466
                         mol_type = protein
                         organism = Influenza B
SEQUENCE: 46
MLPSTIQTLT LFLTSGGVLL SLYVSASLSY LLYSDILLKF SPTEITAPTM PLDCANASNV    60
QAVNRSATKG VTLLLPEPEW TYPRLSCPGS TFQKALLISP HRFGETKGNS APLIIREPFI    120
ACGPKECKHF ALTHYAAQPG GYYNGTREDK NKLRHLISVK LGKIPTVENS IFHMAAWSGS    180
ACHDGREWTY IGVDGPDSNA LLKIKYGEAY TDTYHSYANN ILRTQESACN CIGGDCYLMI    240
TDGSASGISE CRFLKIREGR IIKEIFPTGR VEHTEEECTCG FASNKTIECA CRDNSYTAKR   300
PFVKLNVETD TAEIRLMCTE TYLDTPRPDD GSITGPCESN GDKGSGGIKG GFVHQRMASK   360
IGRWYSRTMS KTKRMGMGLY VKYDGDPWTD SDALALSGVM VSMEEPGWYS FGFEIKDKKC    420
DVPCIGIEMV HDGGKKTWHS AATAIYCLMG SGQLLWDTVT GVDMAL                   466

SEQ ID NO: 47            moltype = AA   length = 466
```

```
FEATURE                  Location/Qualifiers
source                   1..466
                         mol_type = protein
                         organism = Influenza B
SEQUENCE: 47
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFI 120
ACGPKECKHF ALTHYAAQPG GYYNGTRGDR NKLRHLISVK LGKIPTVENS IFHMAAWSGS 180
ACHDGKEWTY IGVDGPDNNA LLIKIKYGEAY TDTYHSYANN ILRTQESACN CIGGNCYLMI 240
TDGSASGVSE CRFLKIREGR IIKEIFPTGR VKHTEECTCG FASNKTIECA CRDNSYTAKR 300
PFVKLNVETD TAEIRLMCTE TYLDTPRPDD GSITGPCESN GDKGSGGIKG GFVHQRMASK 360
IGRWYSRTMS KTKRMGMGLY VKYDGDPWAD SDALALSGVM VSMEEPGWYS FGFEIKDKKC 420
DVPCIGIEMV HDGGKETWHS AATAIYCLMG SGQLLWDTVT GVDMAL           466

SEQ ID NO: 48            moltype = AA   length = 465
FEATURE                  Location/Qualifiers
source                   1..465
                         mol_type = protein
                         organism = Influenza B
SEQUENCE: 48
MLPSTIQTLT LFLTSGGVLL SLYVSASLSY LLYSDILLKF SPKITAPTMT LDCANASNVQ  60
AVNRSATKEM TFLLPEPEWT YPRLSCQGST FQKALLISPH RFGEARGNSA PLIIREPFIA 120
CGPKECKHFA LTHYAAQPGG YYNGTREDRN KLRHLISVKL GKIPTVENSI FHMAAWSGSA 180
CHDGREWTYI GVDGPDSNAL IKIKYGEAYT DTYHSYANNI LRTQESACNC IGGDCYLMIT 240
DGSASGISKC RFLKIREGRI IKEIFPTGRV EHTEECTCGF ASNKTIECAC RDNNYTAKRP 300
FVKLNVETDT AEIRLMCTET YLDTPRPDDG SITGPCESNG DKGRGGIKGG FVHQRMASKI 360
GRWYSRTMSK TERMGMELYV KYDGDPWTDS DALDPSGVMV SMKEPGWYSF GFEIKDKKCD 420
VPCIGIEMVH DGGKKTWHSA ATAIYCLMGS GQLLWDTVTG VDMAL             465

SEQ ID NO: 49            moltype = AA   length = 466
FEATURE                  Location/Qualifiers
source                   1..466
                         mol_type = protein
                         organism = Influenza B
SEQUENCE: 49
MLPSTIQTLT LFLTSGGVLL SLYVSASLSY LLYSDILLKF SPTKRTAPTM SLDCANVSNV  60
QAVNRSATKE MTFLLPEPEW TYPRLSCQGS TFQKALLISP HRFGEARGNS APLIIREPFI 120
ACGPKECKHF ALTHYAAQPG GYYNGTRKDR NKLRHLISVK LGKIPTVENS IFHMAAWSGS 180
ACHDGREWTY IGVDGPDSNA LIKIKYGEAY TDTYHSYANN ILRTQESACN CIGGDCYLMI 240
TDGSASGISK CRFLKIREGR IIKEIFPTGR VEHTEECTCG FASNKTIECA CRDNSYTAKR 300
PFVKLNVETD TAEIRLMCTE TYLDTPRPDD GSITGPCESN GDKGLGGIKG GFVHQRMASK 360
IGRWYSRTMS KTERMGMELY VKYDGDPWTD SEALAPSGVM VSMKEPGWYS FGFEIKDKKC 420
DVPCIGIEMV HDGGKETWHS AATAIYCLMG SGQLLWDTVT GVDMAL           466

SEQ ID NO: 50            moltype = AA   length = 466
FEATURE                  Location/Qualifiers
source                   1..466
                         mol_type = protein
                         organism = Influenza B
SEQUENCE: 50
MLPSTIQTLT LFLTSGGVLL SLYVSASLSY LLYSDILLKF SRTEVTAPIM PLDCANASNV  60
QAVNRSATKG VTPLLPEPEW TYPRLSCPGS TFQKALLISP HRFGETKGNS APLIIREPFI 120
ACGPKECKHF ALTHYAAQPG GYYNGTREDR NKLRHLISVK LGKIPTVENS IFHMAAWSGS 180
ACHDGREWTY IGVDGPDSNA LLIKIKYGEAY TDTYHSYAKN ILRTQESACN CIGGDCYLMI 240
TDGPASGISE CRFLKIREGR IIKEIFPTGR VKHTEECTCG FASNKTIECA CRDNSYTAKR 300
PFVKLNVETD TAEIRLMCTK TYLDTPRPND GSITGPCESD GDEGSGGIKG GFVHQRMASK 360
IGRWYSRTMS KTKRMGMGLY VKYDGDPWTD SEALALSGVM VSMEEPGWYS FGFEIKDKKC 420
DVPCIGIEMV HDGGKTTWHS AATAIYCLMG SGQLLWDTVT GVNMTL           466

SEQ ID NO: 51            moltype = AA   length = 54
FEATURE                  Location/Qualifiers
source                   1..54
                         mol_type = protein
                         organism = Influenza A
SEQUENCE: 51
SIQIGNQSQI ETCNQSVITY ENNTWVNQTY VNISNTNFAA GQSVVSVKLA GNSS        54

SEQ ID NO: 52            moltype = AA   length = 53
FEATURE                  Location/Qualifiers
REGION                   1..53
                         note = A synthetic sequence
source                   1..53
                         mol_type = protein
                         organism = synthetic construct
SEQUENCE: 52
IQIGNQSQIE CCNQSVITYE NNTWVNQTYV NISNTNFAAG QSVVSVKLAG NSS          53

SEQ ID NO: 53            moltype = AA   length = 53
FEATURE                  Location/Qualifiers
```

```
REGION                  1..53
                        note = A synthetic sequence
source                  1..53
                        mol_type = protein
                        organism = synthetic construct
SEQUENCE: 53
IQIGNQSQIE TCCQSVITYE NNTWVNQTYV NISNTNFAAG QSVVSVKLAG NSS          53

SEQ ID NO: 54           moltype = AA  length = 53
FEATURE                 Location/Qualifiers
REGION                  1..53
                        note = A synthetic sequence
source                  1..53
                        mol_type = protein
                        organism = synthetic construct
SEQUENCE: 54
IQIGNQSQIE CCCQSVITYE NNTWVNQTYV NISNTNFAAG QSVVSVKLAG NSS          53

SEQ ID NO: 55           moltype = AA  length = 53
FEATURE                 Location/Qualifiers
REGION                  1..53
                        note = A synthetic sequence
source                  1..53
                        mol_type = protein
                        organism = synthetic construct
SEQUENCE: 55
IQIGNQSQIC TCNQSVITYE NNTWVNQTYV NISNTNFAAG QSVVSVKLAG NSS          53

SEQ ID NO: 56           moltype = AA  length = 53
FEATURE                 Location/Qualifiers
REGION                  1..53
                        note = A synthetic sequence
source                  1..53
                        mol_type = protein
                        organism = synthetic construct
SEQUENCE: 56
IQIGNQSQIE TCNCSVITYE NNTWVNQTYV NISNTNFAAG QSVVSVKLAG NSS          53
```

What is claimed is:

1. A method of immunizing an avian or a mammal, comprising: administering to the avian or the mammal a composition having an effective amount of an isolated recombinant influenza virus comprising stabilized neuraminidase (NA) tetramers and a NA viral segment encoding a modified NA monomer that forms virions having the stabilized NA tetramers relative to a corresponding influenza virus having a parental NA viral segment encoding an unmodified NA monomer, wherein the modified NA monomer comprises a modified NA stalk that results in the stabilized NA tetramers, wherein the modified NA has a cysteine at position 48 or position 50 or both positions of 48 and 50 relative to the numbering of NA1 of SEQ ID NO:37.

2. The method of claim 1 wherein the mammal is a human.

3. The method of claim 1 wherein the composition is administered intranasally.

4. The method of claim 1 wherein the composition is administered via injection.

5. The method of claim 1 wherein the modified NA stalk further comprises a deletion, an insertion, at least one other amino acid substitution, or any combination thereof.

6. The method of claim 1 wherein the modified NA has a cysteine at position 48.

7. The method of claim 1 wherein modified NA has a cysteine at position 50.

8. The method of claim 1 wherein modified NA has a cysteine at position 48 and position 50.

9. The method of claim 1 wherein the NA stalk is modified within residues 1 to 10 or residues 10 to 20 from the C-terminus of the transmembrane domain.

10. The method of claim 1 wherein the NA is N1, N2, N3 or N5.

11. The method of claim 1 wherein the HA is H1, H3, H5 or H7.

12. The method of claim 1 further comprising administering an adjuvant.

13. The method of claim 12 wherein the adjuvant comprises immunostimulatory DNA sequences, bacterium-derived components, aluminum salt (alum) or a squalene oil-in-water emulsion.

14. The method of claim 1 wherein the composition further comprises an adjuvant.

15. The method of claim 14 wherein the adjuvant comprises immunostimulatory DNA sequences, bacterium-derived components, aluminum salt (alum) or a squalene oil-in-water emulsion.

16. The method of claim 15 wherein the squalene oil-in-water emulsion system comprises MF59 or AS03.

17. The method of claim 1 wherein the virus is chemically inactivated.

* * * * *